(12) United States Patent
McDaniel et al.

(10) Patent No.: US 11,382,674 B2
(45) Date of Patent: Jul. 12, 2022

(54) FIFTH METATARSAL REPAIR SYSTEMS AND METHODS OF USE

(71) Applicant: Arthrex, Inc., Naples, FL (US)

(72) Inventors: Stephen Riddle McDaniel, San Rafael, CA (US); Alexander Carlo Buscaglia, Chicago, IL (US); Kyle Edward Lappin, Lake Zurich, IL (US); Samuel Bruce Adams, Jr., Chapel Hill, NC (US); Brian John Burgess, Glen Ellyn, IL (US); David N. Garras, Orland Park, IL (US)

(73) Assignee: Arthrex, Inc., Naples, FL (US)

( * ) Notice: Subject to any disclaimer, the term of this patent is extended or adjusted under 35 U.S.C. 154(b) by 450 days.

(21) Appl. No.: 16/582,411

(22) Filed: Sep. 25, 2019

(65) Prior Publication Data

US 2020/0015866 A1   Jan. 16, 2020

Related U.S. Application Data

(63) Continuation of application No. 15/723,596, filed on Oct. 3, 2017, now Pat. No. 10,463,408.

(Continued)

(51) Int. Cl.
*A61B 17/72* (2006.01)
*A61B 17/17* (2006.01)
(Continued)

(52) U.S. Cl.
CPC ...... *A61B 17/7291* (2013.01); *A61B 17/1775* (2016.11); *A61B 17/7225* (2013.01); (Continued)

(58) Field of Classification Search
CPC ............ A61B 17/7291; A61B 17/1775; A61B 17/7225; A61B 17/7266; A61B 17/88; (Continued)

(56) References Cited

U.S. PATENT DOCUMENTS 3,760,802 A    9/1973  Fischer et al.
5,057,103 A *  10/1991 Davis ................... A61B 17/921
                                                    606/68

(Continued)

OTHER PUBLICATIONS

International Search Report and Written Opinion of the International Searching Authority for International Application No. PCT/US2017/054899 dated Dec. 19, 2017.

(Continued)

*Primary Examiner* — Eduardo C Robert
*Assistant Examiner* — David C Comstock
(74) *Attorney, Agent, or Firm* — Carlson, Gaskey & Olds, P.C.

(57) ABSTRACT

The present application relates to repair systems, and more particularly to fifth metatarsal repair systems and methods of use. The repair systems described herein can include a fixation device with a threaded section. The repair systems described herein can include one or more grippers designed to be deflected outward to grip the sidewalls of an intramedullary canal of the fifth metatarsal. The repair systems described herein can include an end cap. The end cap can include a fastener including thread designed to engage the threaded section of the fixation device. The end cap can include a cap designed to move relative to the fastener.

17 Claims, 49 Drawing Sheets

Related U.S. Application Data

(60) Provisional application No. 62/404,382, filed on Oct. 5, 2016.

(51) Int. Cl.
   *A61B 17/88* (2006.01)
   *A61B 17/92* (2006.01)
   *A61B 17/16* (2006.01)
   *A61B 17/80* (2006.01)

(52) U.S. Cl.
   CPC .......... *A61B 17/7266* (2013.01); *A61B 17/88* (2013.01); *A61B 17/164* (2013.01); *A61B 17/1682* (2013.01); *A61B 17/1717* (2013.01); *A61B 17/8061* (2013.01); *A61B 17/8875* (2013.01); *A61B 17/921* (2013.01)

(58) Field of Classification Search
   CPC ............... A61B 17/164; A61B 17/1682; A61B 17/1717; A61B 17/8061; A61B 17/8875; A61B 17/921
   USPC .......... 606/62, 63, 66, 67, 68, 280, 281, 282, 606/286, 287, 288, 289, 290, 291, 295, 606/297, 310, 313, 319, 320, 326, 327, 606/328, 96, 99, 102, 104, 105, 86 B
   See application file for complete search history.

(56) References Cited

U.S. PATENT DOCUMENTS

| | | | |
|---|---|---|---|
| 5,429,641 A * | 7/1995 | Gotfried | A61B 17/8888 411/383 |
| 5,899,908 A * | 5/1999 | Kuslich | A61F 2/446 606/80 |
| 7,879,036 B2 | 2/2011 | Biedermann et al. | |
| 8,939,977 B2 | 1/2015 | DiPoto et al. | |
| 9,814,499 B2 | 11/2017 | Buscaglia et al. | |
| 10,357,314 B2 * | 7/2019 | Cocaign | A61B 17/1775 |
| 2003/0233098 A1 * | 12/2003 | Markworth | A61B 17/17 606/96 |
| 2005/0246034 A1 | 11/2005 | Soubeiran | |
| 2006/0264954 A1 | 11/2006 | Sweeney, II et al. | |
| 2007/0250067 A1 * | 10/2007 | Schmieding | A61B 17/1764 606/96 |
| 2010/0256638 A1 * | 10/2010 | Tyber | A61B 17/1775 606/62 |
| 2011/0160728 A1 | 6/2011 | Blitz et al. | |
| 2011/0282346 A1 | 11/2011 | Pham et al. | |
| 2013/0116693 A1 | 5/2013 | Nelson et al. | |
| 2015/0359573 A1 | 12/2015 | Adams et al. | |
| 2016/0166292 A1 * | 6/2016 | Mighell | A61B 17/7233 606/62 |

OTHER PUBLICATIONS

International Preliminary Report on Patentability for International Application No. PCT/US2017/054899 dated Apr. 18, 2019.

* cited by examiner

FIFTH METATARSAL REPAIR SYSTEMS AND METHODS OF USE

BACKGROUND

Field

Embodiments of the present application relate to repair systems, tools, and methods for providing reinforcement of bones. More specifically, the present application relates to repair systems, tools, and methods for providing reconstruction and reinforcement of the fifth metatarsal.

Description of the Related Art

Bone fractures are a common medical condition both in the young and old segments of the population. As one example, sports and work-related accidents account for a significant number of bone fractures seen in emergency rooms among all age groups. Further, the acceptance and ubiquitous application of passive restraint systems in automobiles has created greater numbers of non-life threatening fractures. In the past, a person that might expire from a serious automobile accident now survives with multiple traumas and resultant fractures. With an increasingly aging population, osteoporotic fractures have increased. Osteoporosis and osteoarthritis are among the most common conditions to affect the musculoskeletal system, as well as frequent causes of locomotor pain and disability. The National Osteoporosis Foundation estimates that as many as 44 million Americans are affected by osteoporosis and low bone mass, leading to fractures in more than 300,000 people over the age of 65.

One current treatment of bone fractures includes surgically resetting the fractured bone. After the surgical procedure, the fractured area of the body (i.e., where the fractured bone is located) is often placed in an external cast for an extended period of time to ensure that the fractured bone heals properly. This can take several months for the bone to heal and for the patient to remove the cast before resuming normal activities.

In some instances, an intramedullary (LM) rod or nail is used to align and stabilize the fracture. In that instance, a metal rod is placed inside a canal of a bone and fixed in place, typically at both ends. See, for example, Fixion™ IM (Nail), www.disc-o-tech.com. Placement of conventional IM rods are typically a "line of sight" and require access collinear with the center line of the IM canal. Invariably, this line of sight access violates, disrupts, and causes damage to important soft tissue structures such as ligaments, tendons, cartilage, fascia, and epidermis. This approach requires incision, access to the canal, and placement of the IM nail. The nail can be subsequently removed or left in place. A conventional IM nail procedure requires a similar, but possibly larger, opening to the space, a long metallic nail being placed across the fracture, and either subsequent removal, or when the nail is not removed, a long term implant of the IM nail. The outer diameter of the IM nail must be selected for the minimum inside diameter of the space. Therefore, portions of the IM nail may not be in contact with the canal. Further, micro-motion between the bone and the IM nail may cause pain or necrosis of the bone. In still other cases, infection can occur. The LM nail may be removed after the fracture has healed. This requires a subsequent surgery with all of the complications and risks of a later intrusive procedure. In general, rigid IM rods or nails are difficult to insert, can damage the bone and require additional incisions for cross-screws to attach the rods or nails to the bone.

SUMMARY

The repair systems, tools, and methods have several features, no single one of which is solely responsible for its desirable attributes. Without limiting the scope as expressed by the claims that follow, the more prominent features of the systems and methods will now be discussed briefly. After considering this discussion, and particularly after reading the section entitled "Detailed Description" one will understand how the features of the systems and methods provide several advantages over other devices.

One of the advantages of embodiments of the repair systems described herein include that the repair systems are simple, intuitive systems. The repair systems advantageously have few parts, making the repair systems robust and cost-effective to manufacture.

The repair systems can be used in a variety of surgeries, such as minimally invasive surgery. For instance, in various embodiments, the repair systems can be used in all surgeries, and in particular embodiments, the repair systems are favorable in the repair of the fifth metatarsal, including fractures of the fifth metatarsal.

In some embodiments, a repair system is provided. The repair system can include a fixation device. The fixation device can include an elongate body configured to be inserted within a fifth metatarsal, the elongate body comprising a threaded section. The fixation device can include one or more grippers configured to be deflected outward to grip the sidewalls of a canal of the fifth metatarsal. The repair system can include an end cap. The end cap can include a fastener comprising thread configured to engage the threaded section of the fixation device. The end cap can include a cap, wherein the cap is configured to move relative to the fastener.

In some embodiments, the elongate body comprises a bend. In some embodiments, the end cap is configured for intra-operative compression. In some embodiments, the fastener head is captive within the cap. In some embodiments, the cap is configured for polyaxial movement relative to the fastener. In some embodiments, the cap is configured to rotate relative to the fastener. In some embodiments, the cap comprises a tapered external surface. In some embodiments, the cap comprises a cylindrical boss. In some embodiments, the thread of the fastener is configured to extend distally from the cap when the fastener is disposed within the cap, further comprising a projection extending distally from the cap. In some embodiments, the cap comprises one or more grooves configured to self-tap into the fifth metatarsal. In some embodiments, the thread of the fastener is configured to extend distally from the cap when the fastener is disposed within the cap, the cap further comprising one or more hooks extending proximally.

In some embodiments, a method of using a repair system is provided. The method can include the step of inserting a fixation device within a canal of a fifth metatarsal. The method can include the step of selecting an end cap comprising a cap and a fastener. The method can include the step of coupling the end cap to the fixation device by engaging the fastener with a lumen of the fixation device. The method can include the step of adjusting the position of the end cap relative to the fixation device to apply intra-operative compression to one or more segments of the fifth metatarsal.

The method can include the step of limiting a depth of a counter bore based on the end cap. In some embodiments, limiting the depth of the counter bore comprises abutting a stop of a reamer with a portion of a drill guide. The method can include the step of limiting a depth of insertion of the fixation device based on the end cap. In some embodiments, limiting the depth of insertion of the fixation device comprises abutting a sleeve of an insertion tool with the anatomy of a patient. In some embodiments, limiting the depth of insertion of the fixation device comprises pulling and rotating a sleeve of an insertion tool to select the depth of insertion. The method can include the step of actuating a gripper to secure the fixation device within the intramedullary canal of the fifth metatarsal. The method can include the step of rotating the cap relative to the fastener after coupling the end cap to the fixation device. The method can include the step of angling the cap relative to the fastener after coupling the end cap to the fixation device.

BRIEF DESCRIPTION OF THE DRAWINGS

These and other features, aspects, and advantages of the repair systems, tools, and methods disclosed herein are described below with reference to the drawings of embodiments, which are intended to illustrate and not to limit the present application. Additionally, from figure to figure, the same reference numerals have been used to designate the same components of an illustrated embodiment. The following is a brief description of each of the drawings.

DETAILED DESCRIPTION

Figure 1:
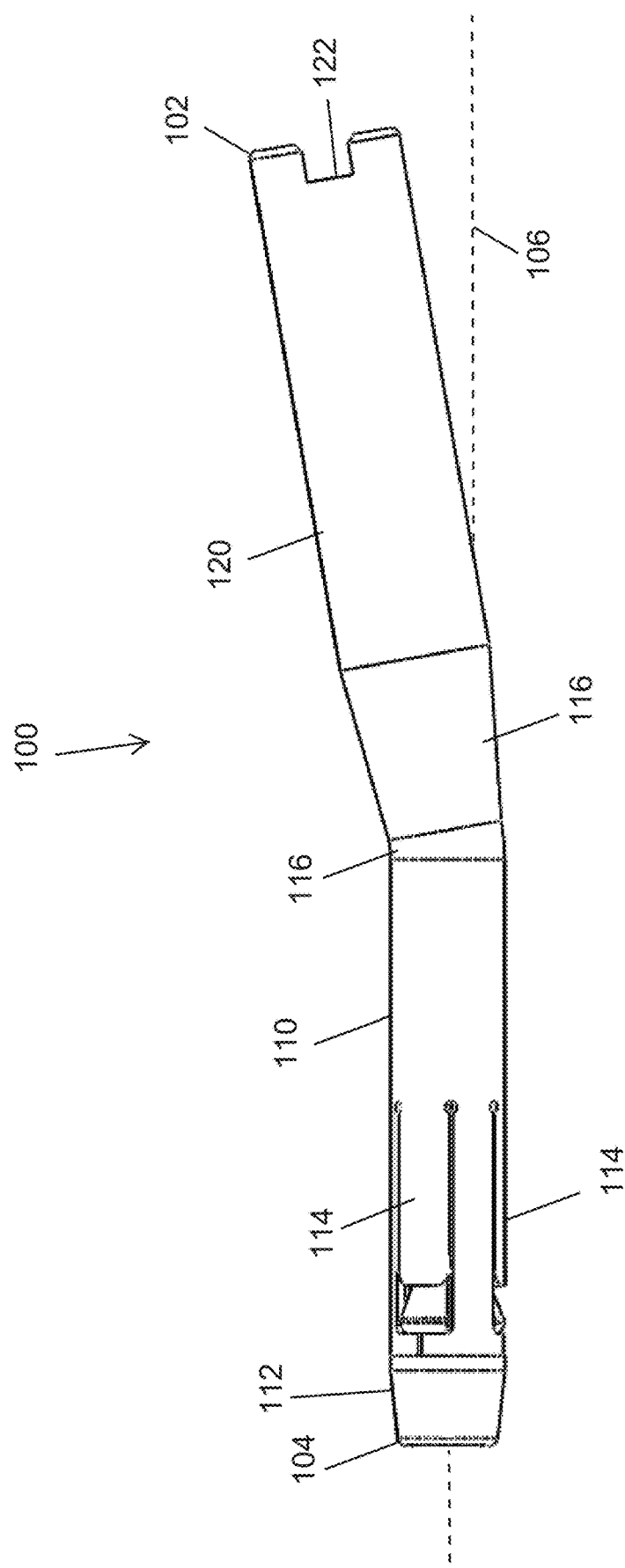
FIG. 1 is a perspective view of an embodiment of a fixation device.
Figure 2:
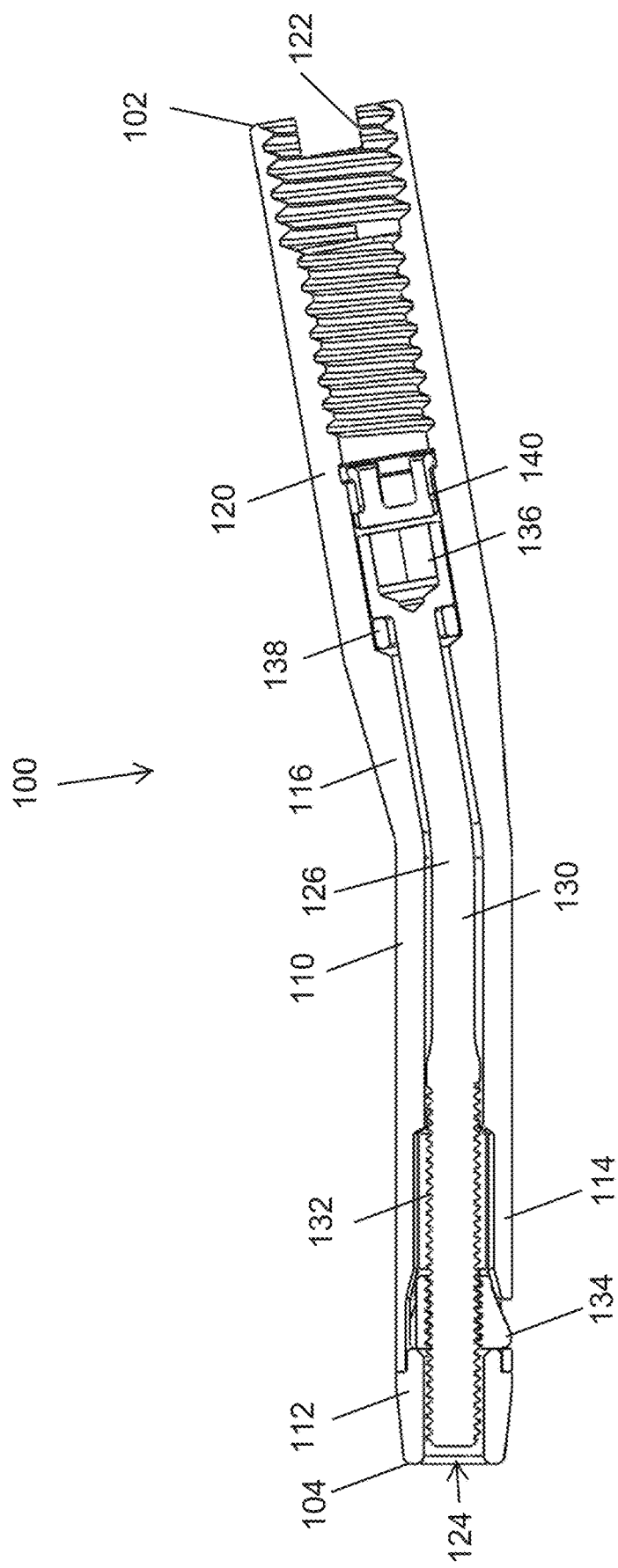
FIG. 2 is a cross-sectional view of the fixation device of FIG. 1.

FIGS. 1 and 2 are perspective views of the fixation device 100. The fixation device 100 can include a proximal end 102 (near the user) and a distal end 104 (further from the user). The proximal end 102 and the distal end 104 can refer to the position of an end of the fixation device 100 relative to the remainder of the fixation device 100 or relative to the opposing end as it appears in the drawings. The proximal end 102 can refer to the end that is manipulated by the user. The distal end 104 can refer to the end that is inserted and advanced within the bone. The use of proximal and distal can change in another context, for instance in an anatomical context in which proximal and distal are relative to the patient, or where the entry point is distal from the user.

The fixation device 100 can include a longitudinal axis 106 extending from the distal end 104 toward the proximal end 102. In the illustrated embodiment, the fixation device 100 is bent or curved. The proximal end 102 of the fixation device 100 can deviate from the longitudinal axis 106. In some embodiments, the enclosed angle between the proximal end 102 the longitudinal axis 106 is approximately 10 degrees but other configurations are contemplated (e.g., 1 degree, 2 degrees, 3, degrees, 4 degrees, 5 degrees, 6 degrees, 7 degrees, 8 degrees, 9 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 1 and 10 degrees, between 1 and 20 degrees, between 1 and 30 degrees, greater than 5 degrees, greater than 10 degrees, greater than 15 degrees, greater than 20 degrees, less than 20 degrees, less than 15 degrees, less than 10 degrees, etc.) The fixation device 100 can be considered an intramedullary nail. The fixation device 100 can be designed for the fixation of fifth metatarsal fractures. The fixation device 100 can be designed for insertion into the medullary canal of the fifth metatarsal. The fixation device 100 can be designed for insertion through a proximal entry portal created at the tip of the proximal tuberosity, as described herein.

The fixation device 100 can include a distal portion 110. The distal portion 110 can extend from the distal end 104 toward the proximal end 102. The distal portion 110 can include a tip section 112. The tip section 112 can be considered the insertion section. The tip section 112 can be located near the distal end 104. In the illustrated embodiment, the tip section 112 comprises a tapered tip. In some embodiments, the tip section 112 can be tapered inward toward the longitudinal axis 106. In some embodiments, the tip section 112 can be a cover at the distal end 104 of the fixation device 100. The tip section 112 can act as a blunt obturator. The tip section 112 can facilitates penetration of bone, such as penetration of an intramedullary canal by the fixation device 100.

The distal portion 110 can include one or more grippers 114. The one or more grippers 114 can be considered a bone engaging mechanism. The one or more grippers 114 can engage the fifth metatarsal of a patient when placed in the intramedullary canal within a post fractured bone. The one or more grippers 114 can be deployed radially outward against the wall of the intramedullary canal or other canal such as a reamed canal. On entry into the canal, the one or more grippers 114 can be flat and retracted. Upon deployment, the one or more grippers 114 can pivot radially outward from the distal portion 110 to grip the fifth metatarsal from the inside of the bone. In the illustrated embodiment, the fixation device 100 can include three grippers 114. Other configurations are contemplated (e.g., one gripper, two grippers, three grippers, four grippers, five grippers, six grippers, etc.). In the illustrated embodiment, the one or more grippers 114 are disposed circumferentially around the distal portion 110. In the illustrated embodiment, the one or more grippers 114 are equally spaced around the circumference of the distal portion 110.

The fixation device 100 can include one or more bent sections 116. The one or more bent sections 116 can angle the fixation device 100. The one or more bent sections 116 can allow the fixation device 100 to more closely match the anatomy of the fifth metatarsal. In the illustrated embodiment, the fixation device 100 can include two bent sections 116. The lateral bend of the fixation device 100 can be designed accommodate the lateral entry position on the proximal tuberosity. A traditional, straight intramedullary nail necessitates an entry point that attempts to linearize the bone. A straight intramedullary nail may require the user to select an entry point that is medial and dorsal to the tuberosity (e.g., "high and tight"). A straight intramedullary nail may require the user to select an entry point that allows the screw to be threaded into the bone canal. The lateral entry point of the proximal tuberosity can be easier to identify and access as it is palpable under the skin.

The fixation device 100 can include a hub 120. The hub 120 can be rigidly coupled to the distal portion 110 via the one or more bent sections 116. In the illustrated embodiment, the distal portion 110 and the hub 120 are not coaxial. The hub 120 can include an engagement member 122. The engagement member 122 can be designed to engage an insertion tool, or a portion of an insertion tool, as described herein.

The fixation device 100 can be generally cylindrical. The distal portion 110 can have a smaller diameter than the hub 120. The one or more bent sections 116 can transition the fixation device 100 from the smaller diameter of the distal portion 110 to the larger diameter of the hub 120.

Figure 3:
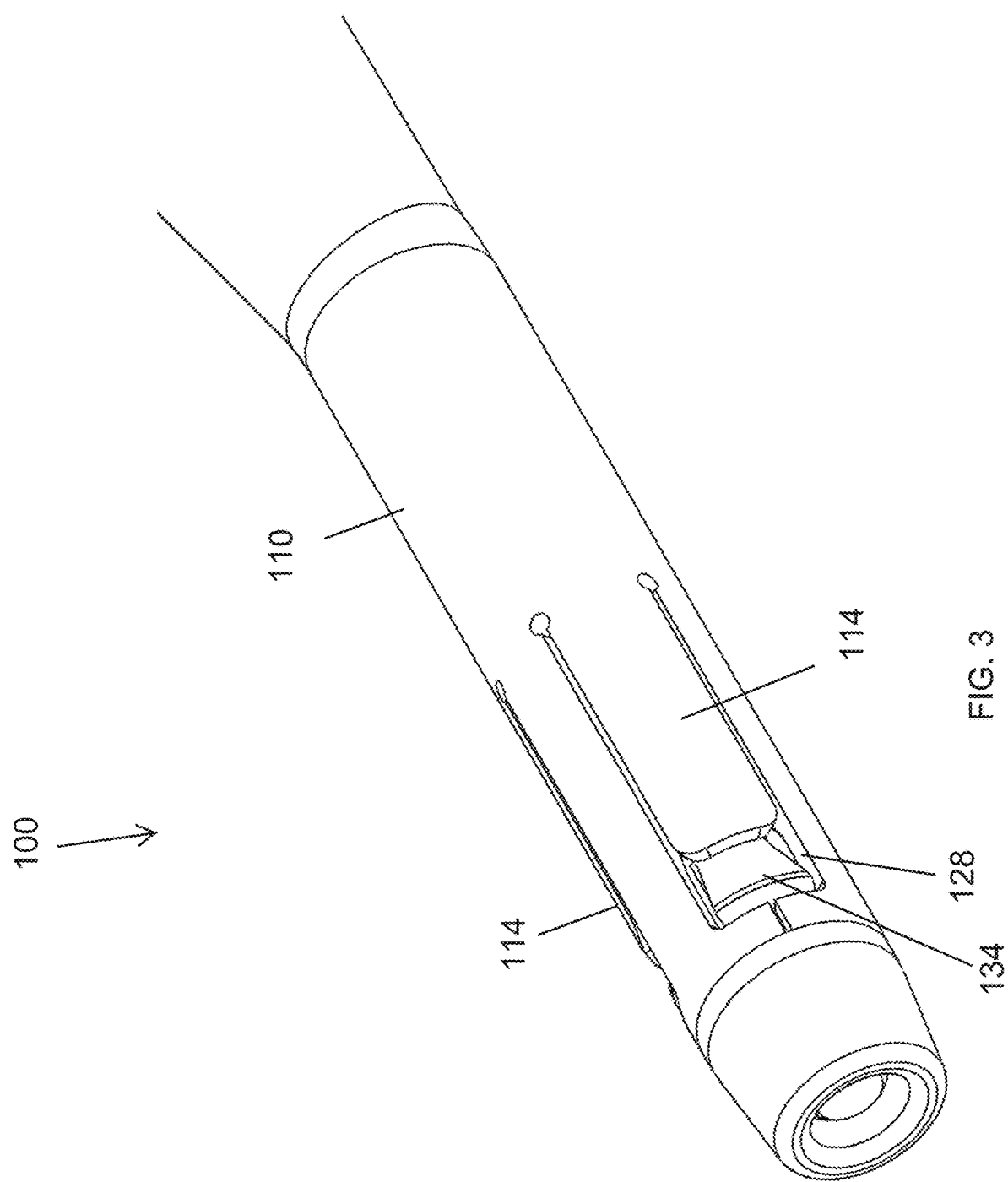
FIG. 3 is a distal view of the fixation device of FIG. 1.

FIG. 2 is a cross-sectional view of the fixation device 100. The fixation device 100 can include a lumen 124. The lumen 124 can extend from the proximal end 102 to the distal end 104. The fixation device 100 can include an actuator 126. The actuator 126 can be designed to deploy the one or more grippers 114. The actuator 126 can include an elongate member 130. The elongate member 130 can include at least one bend in order to be disposed within the one or more bent sections 116. The elongate member 130 can have a reduced diameter to accommodate the bend in the fixation device 100. The elongate member 130 can include a thread 132. The fixation device 100 can include an actuator head 134. The actuator head 134 can engage the thread 132 of the elongate member 110. The actuator 126 can include a socket 136. The socket 136 can allow the actuator 126 to be rotated. The actuator head 134 can be a wedge. The actuator head 134 can be indexed with a window 128 of the fixation device 100, as shown in FIG. 3. The actuator 126 can be rotated. Rotation of the actuator 126 can cause axial translation of the actuator head 134.

During actuation, the one or more grippers 114 are urged radially outward by a ramped surface on the actuator head 134. As an actuation driver (not shown) turns the actuator 126, the thread 132 of the elongate member 130 rotates in relation to the actuator head 134. This causes the actuator head 134 to be drawn in a proximal direction toward the proximal end 102 of the fixation device 100 as the actuator head 134 traverses the thread 132 of the elongate member 130. The ramped surface on the actuator head 134 outwardly actuates one or more grippers 114. The fixation device 100 may include a bearing surface 138. The bearing surface 138 can be a washer. The fixation device 100 may include a stop 140 to prevent translation of the actuator 126. In some embodiments, the stop 140 proximal to the actuator 126 resists back out of the actuator when collapsing the one or more grippers 114.

FIG. 3 shows the one or more grippers 114 prior to deployment. The fixation device 100 can be inserted into the bone in the configuration shown in FIG. 3. The one or more grippers 114 can be the same diameter as the diameter of the distal portion 110.

Figure 4:
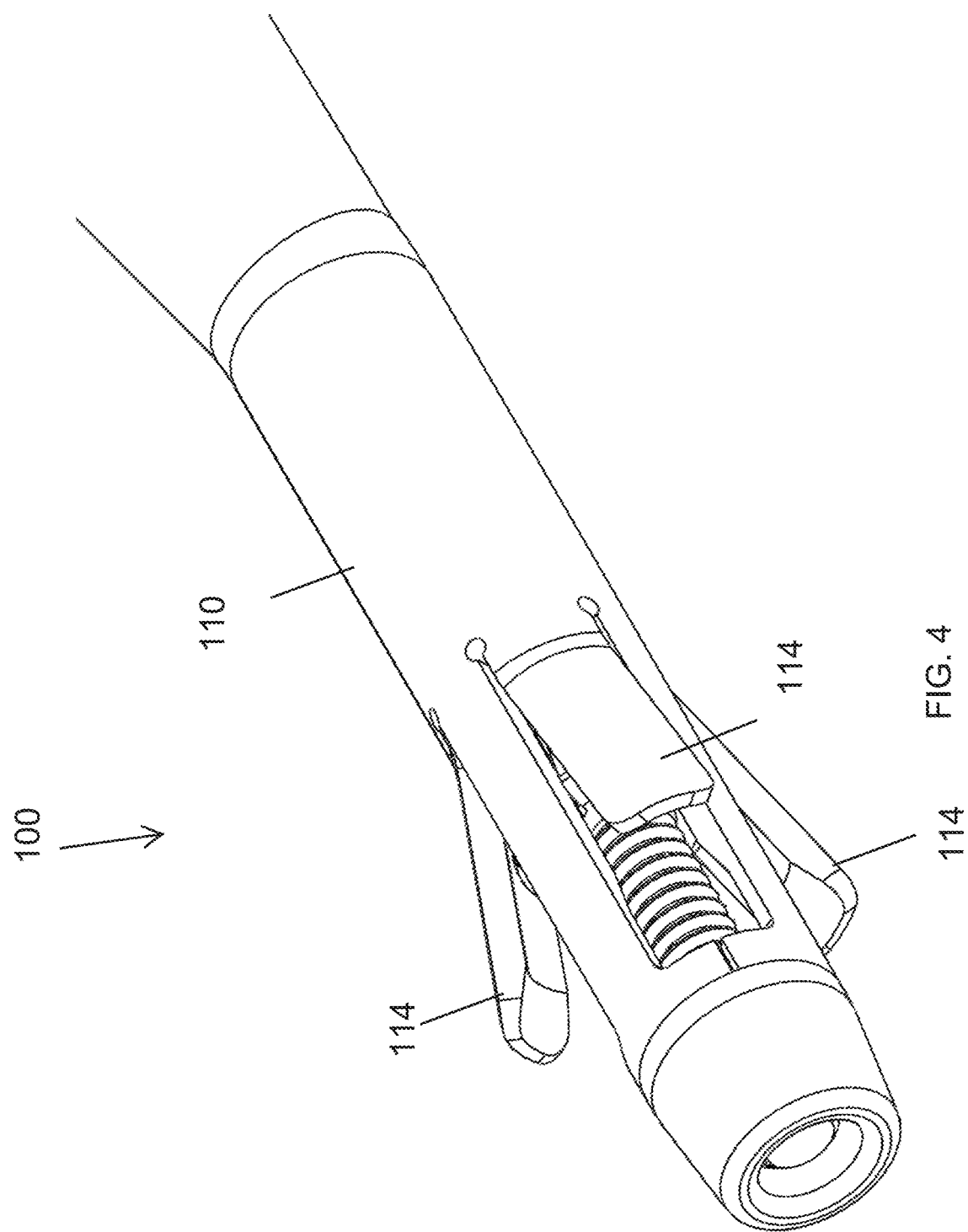
FIG. 4 is a distal view of the fixation device of FIG. 1 with one or more grippers deployed.

FIG. 4 shows the one or more grippers 114 after deployment. The fixation device 100 can grip the sides of the canal of the fifth metatarsal in the configuration shown in FIG. 4. The one or more grippers 114 can be a larger diameter than the diameter of the distal portion 110.

Figure 5:
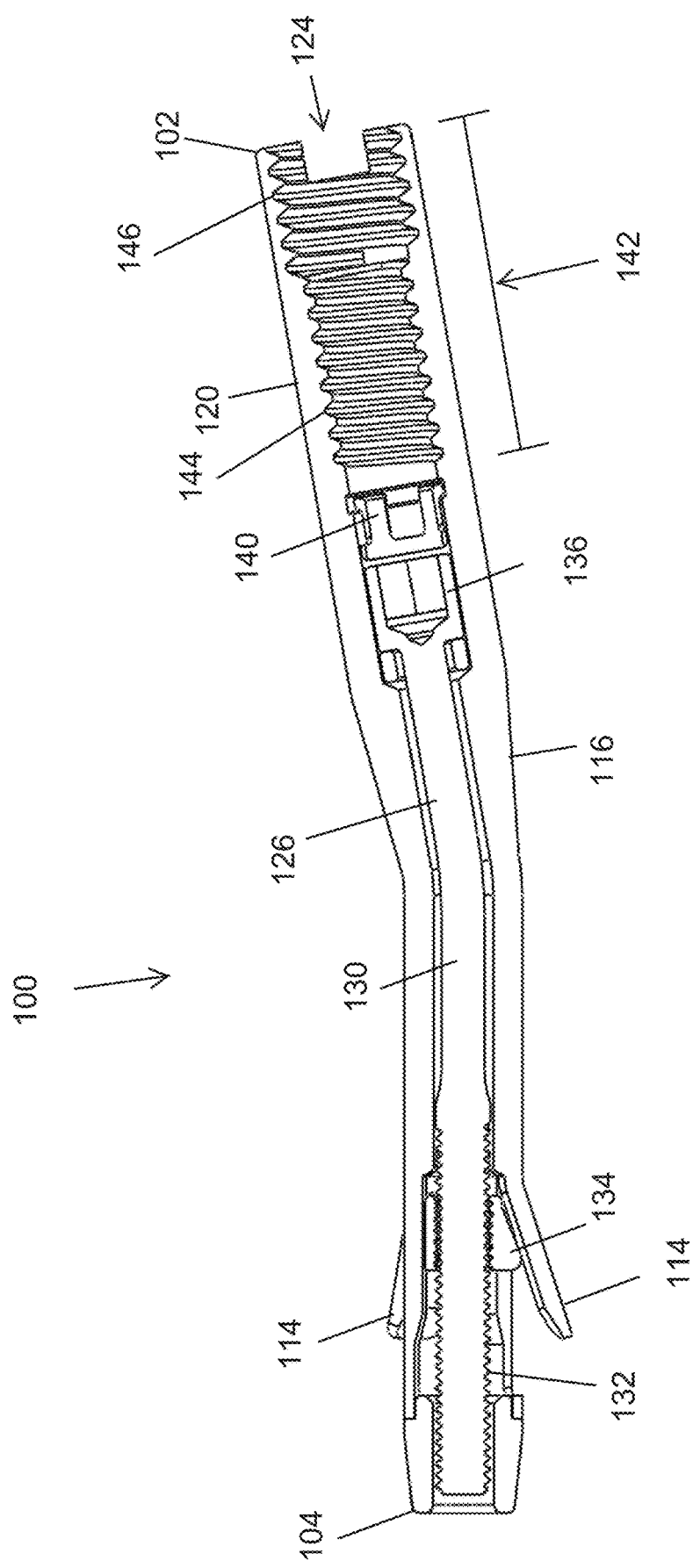
FIG. 5 is a cross-sectional view of the fixation device of FIG. 4.

FIG. 5 shows a cross-sectional view of the one or more grippers 114 after deployment. As described herein, the actuation driver can be rotated to rotate the socket 136 of the actuator 126. The actuator head 134 can be drawn in a proximal direction toward the proximal end 102 of the fixation device 100 when actuator head 134 traverses the thread 132 of the elongate member 130. The ramped surface on the actuator head 134 outwardly actuates one or more grippers 114. The stop 140 can prevent translation of the actuator 126 during rotation of the actuator 126. The one or more grippers 114 can be deployed in the intramedullary canal to lock the position of the fixation device 100.

As described herein, the fixation device 100 can include the lumen 124. The lumen 124 can extend from the proximal end 102 to the distal end 104. The lumen 124 can include a threaded portion 142. The threaded portion 142 can be positioned proximal to the stop 140. The threaded portion 142 can be positioned proximal to the actuator 126. The threaded portion 142 can be positioned proximal to the one or more bent sections 116. The threaded portion 142 can be positioned within the hub 120.

The threaded portion 142 can include a first threaded section 144. The threaded portion 142 can include a second threaded section 146. The diameter of the second threaded section 146 can be larger than the diameter of the first threaded section 144. The first threaded section 144 can be located distally to the second threaded section 146. The thread of the first threaded section 144 can be different than the thread of the second threaded section 146. The first threaded section 144 can include a thread over the entire first threaded section 144, or a portion thereof. The second threaded section 146 can include a thread over the entire second threaded section 146, or a portion thereof. The first threaded section 144 can include a right handed thread. The second threaded section 146 can include a right handed thread. The first threaded section 144 and the second threaded section 146 can have the same handed threaded or an opposite handed thread (e.g., the first threaded section 144 can be right handed and the second threaded section 146 can be left handed). The threaded portion 142 can include one or more sections between the first threaded section 144 and the second threaded section 146. The one or more section can be threaded or non-threaded.

Figure 6:
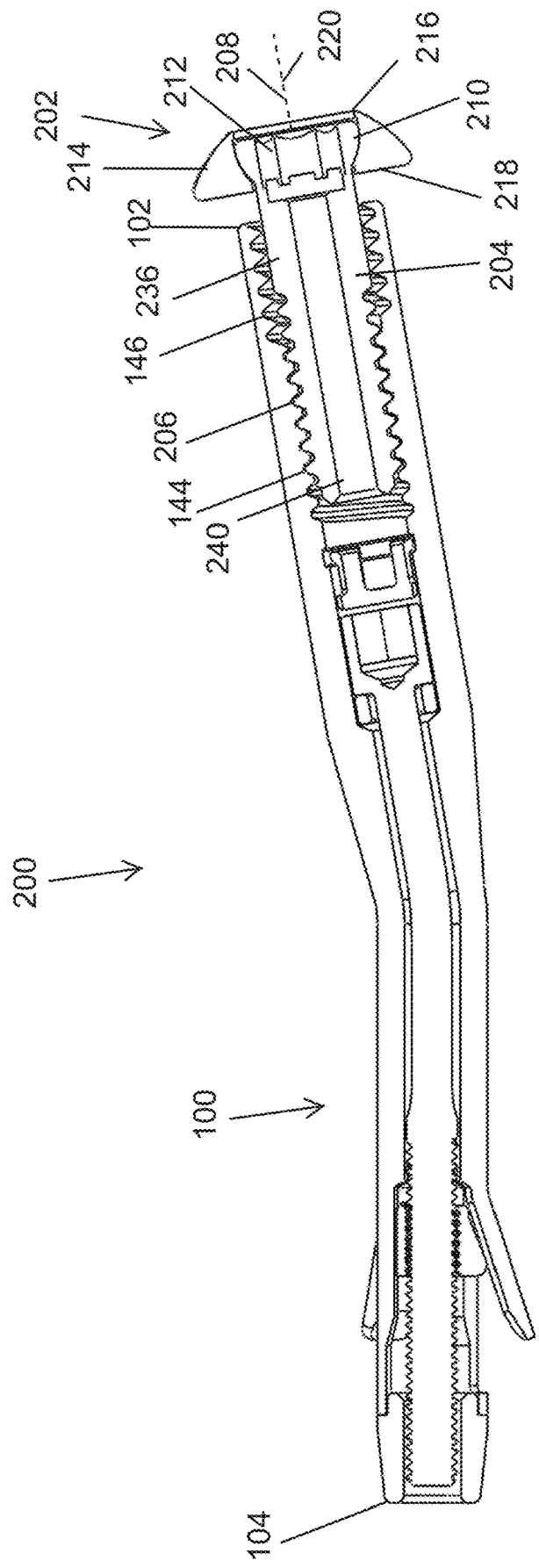
FIG. 6 is a perspective view of a repair system including the fixation device of FIG. 1 and a first embodiment of an end cap.

FIG. 6 shows a repair system 200. The repair system 200 can include the fixation device 100 and any of the end caps described herein.

The repair system 200 can be designed for insertion of the fixation device 100 into the medullary canal after the bone is adequately prepared. The fixation device 100 can be counter sunk inside the bone using an insertion tool, as described herein. After the fixation device 100 is properly positioned within the bone, the one or more grippers 114 are expanded into the canal by engaging the actuator 126, as described herein. The counter sinking allows intra-operative compression to be applied to the fracture by means of an end cap. The end caps described herein can be inserted into the hub 120 of the fixation device 100. The one or more grippers 114 can be located at a distal position of the repair system and the end caps can be located at a proximal position. The end caps described herein include a fastener and a cap. The fastener can be captive within the cap, as described herein. The fastener and the cap can have relative movement, such as translation, rotation and/or polyaxial movement. The end caps can be designed to contact the proximal fragment of the fifth metatarsal. In some embodiments, the cap does not impart rotation on the proximal fragment. The shape of the fastener head and the matching interior surface of the cap allows the cap to pivot about the fastener to accommodate moderate angulation, as described herein. Multiple end cap configurations are possible, as described herein.

Figure 7:
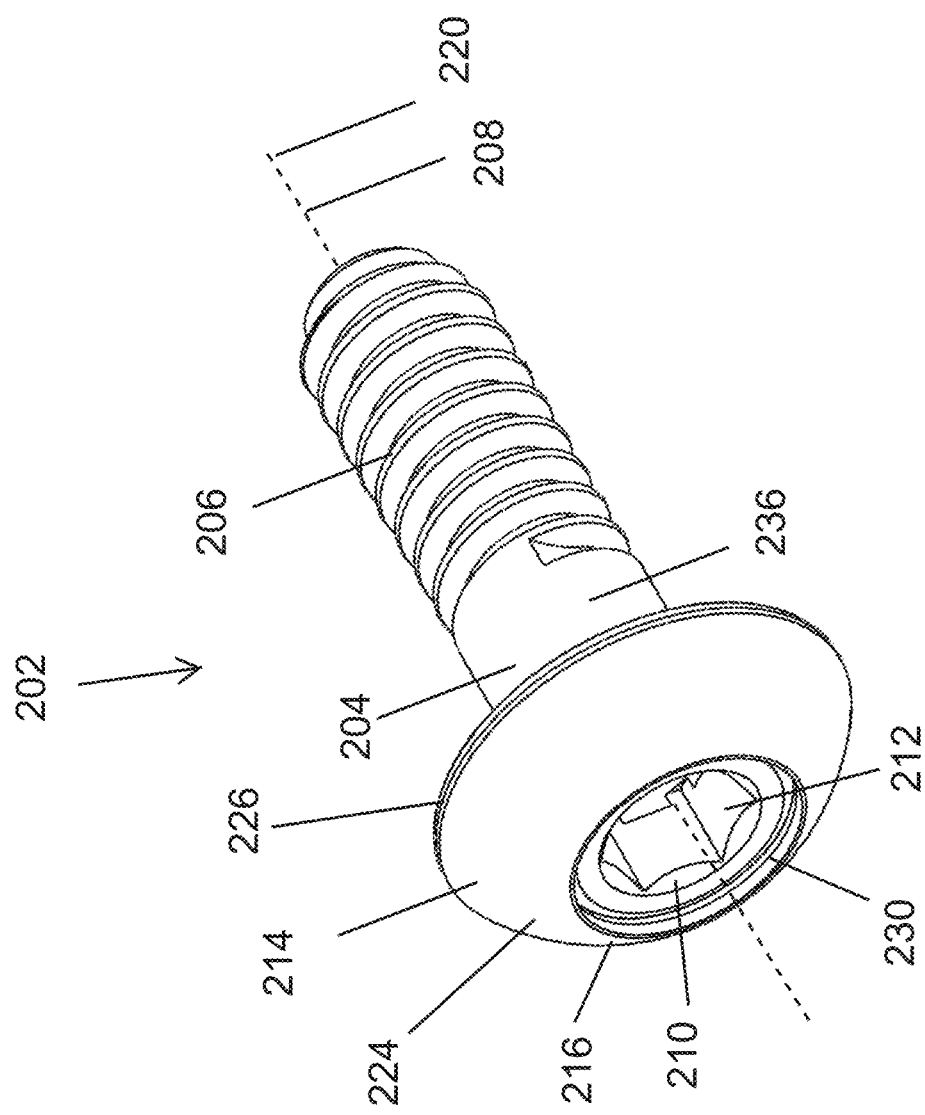
FIG. 7 is a perspective view of the end cap of FIG. 6.
Figure 8:
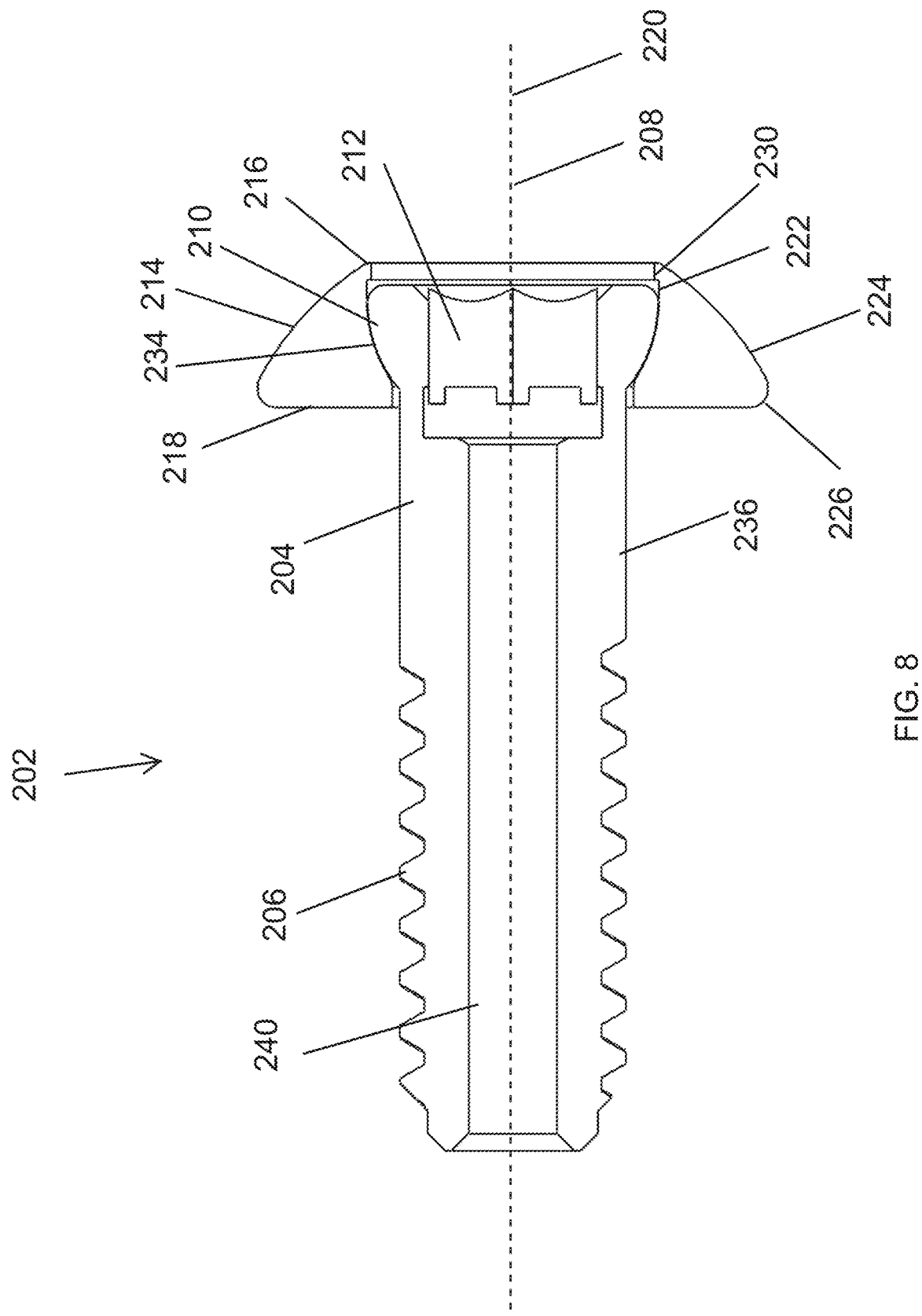
FIG. 8 is a cross-sectional view of the end cap of FIG. 6.

In the illustrated embodiment of FIG. 6, the repair system 200 includes end cap 202. FIG. 7 shows a perspective view of the end cap 202. FIG. 8 shows a cross-sectional view of the end cap 202. In the illustrated embodiment, the end caps described herein can include a fastener 204. The fastener 204 can include a thread 206. The thread 206 can engage the first threaded section 144 of the fixation device 100. The fastener 204 can include a longitudinal axis 208. The fastener 204 can include a fastener head 210. The fastener head 210 can include a socket 212. The socket 212 can be disposed within the fastener head 210. The socket 212 can allow the fastener 204 to be rotated.

The fastener 204 can be rotated to apply compression to one or more bone fragments. The fastener 204 can be rotated to shorten the repair system 200. As one example, rotation of the fastener 204 in one direction can move the fastener 204 toward the distal end 104 of the fixation device 100. As another example, rotation of the fastener 204 in the opposite direction can move the fastener 204 away from the distal end 104 of the fixation device 100.

The end cap 202 can include a cap 214. The cap 214 can include a proximal end 216 and a distal end 218. The cap 214 can include a longitudinal axis 220. In some positions of the end cap 202, the longitudinal axis 208 of the fastener 204 can be coaxial with the longitudinal axis 220 of the cap 214. In some embodiments, the cap 214 can be pivoted relative to the fastener 204. The cap 214 and the fastener 204 can have polyaxial movement therebetween such that the longitudinal axis 208 of the fastener 204 is not coaxial with the longitudinal axis 220 of the cap 214.

Referring to FIG. 8, the cap 214 can have an interior surface 222. The interior surface 222 can be curved. The interior surface 222 can be spherical or generally spherical. The interior surface 222 can be conical or generally conical. In some embodiments, the interior surface 222 can be tapered inward from the proximal end 216 of the cap 214 to the distal end 218 of the cap 214. In some embodiments, the diameter of the interior surface 222 near the proximal end 216 of the cap 214 is greater than a diameter near the distal end 218 of the cap 214.

The cap 214 can have an exterior surface 224. The exterior surface 224 of the cap 214 can be curved. The exterior surface 224 of the cap 214 can be spherical or generally spherical. The exterior surface 224 of the cap 214 can be conical or generally conical. In some embodiments, the exterior surface 224 of the cap 214 can tapered outward from the proximal end 216 of the cap 214 to the distal end 218 of the cap 214. In some embodiments, the diameter of the exterior surface 224 near the proximal end 216 of the cap 214 is less than a diameter of the exterior surface 224 near the distal end 218 of the cap 214. The exterior surface 224 of the cap 214 can include one or more curved edges 226. The curved edges 226 can be located near the distal end 218 of the cap 214. In some methods of use, the distal end 218 of the cap 214 can abut the proximal end of the fixation device 100. In some methods of use, the distal end 218 of the cap 214 can abut the anatomy of the patient. In some methods of use, the distal end 218 of the cap 214 can abut tissue or bone near the tuberosity of the fifth metatarsal.

The fastener head 210 of the fastener 204 can be inserted into the cap 214. The fastener head 210 can be inserted into the proximal end 216 of the cap 214. The thread 206 can extend from the distal end 218 of the cap 214 when the fastener head 210 of the fastener 204 is inserted within the cap 214. The fastener head 210 can have an exterior surface 234. The exterior surface 334 of the fastener head 210 can be curved. The exterior surface 334 of the fastener head 210 can be spherical or generally spherical. The exterior surface 334 of the fastener head 210 can be conical or generally conical. In some embodiments, the exterior surface 334 of the fastener head 210 can be tapered inward. The interior surface 222 of the cap 214 can match or substantially match the exterior surface 234 of the fastener head 210.

The cap 214 can include one or more features to retain the fastener head 210 within the cap 214. The cap 214 can include a lip 230. The lip 230 can form an opening with a smaller diameter than the maximum diameter of the fastener head 210. The lip 230 can prevent the fastener 204 from backing out of the cap 214. In some embodiments, the cap 214 is flexible. In some embodiments, a portion of the cap such as the proximal end 216 or the lip 230 is flexible. The flexibility can allow the fastener 204 to pass in the distal direction over the lip 230. The flexibility can allow the lip 230 to snap back after the fastener 204 is placed within the cap 214.

In some embodiments, the lip 230 can limit translation between the fastener 204 and the cap 214 when the fastener is disposed within the cap 214. In some embodiments, a degree of translation can be permitted between the fastener 204 and the cap 214 when the fastener 204 is disposed within the cap 214. The interior surface 222 of the cap 214 distal to the lip 230 can be sized to allow translation between the fastener 204 and the cap 214. In some embodiments, the translation between the fastener 204 and the cap 214 can occur along the longitudinal axis 208. In some embodiments, the translation between the fastener 204 and the cap 214 can occur along the longitudinal axis 220. In some embodiments, the longitudinal axis 208 of the fastener 204 can be coaxial with the longitudinal axis 220 of the cap 214 during translation. In some embodiments, the longitudinal axis 208 of the fastener 204 is not coaxial with the longitudinal axis 220 of the cap 214 during translation.

In some embodiments, the fastener head 210 and the cap 214 can rotate relative to each other. In some embodiments, a degree of rotation can be permitted between the fastener 204 and the cap 214 when the fastener 204 is disposed within the cap 214. In some embodiments, the fastener head 210 and the cap 214 can rotate 360 degrees relative to each other. In some embodiments, the fastener head 210 and the cap 214 can rotate less than 360 degrees relative to each other (e.g., 90 degree, 180 degrees, etc.). The interior surface 222 of the cap 214 distal to the lip 230 can be sized to allow rotation between the fastener 204 and the cap 214. In some embodiments, the rotation between the fastener 204 and the cap 214 can occur along the longitudinal axis 208. In some embodiments, the rotation between the fastener 204 and the cap 214 can occur along the longitudinal axis 220. In some embodiments, the longitudinal axis 208 of the fastener 204 can be coaxial with the longitudinal axis 220 of the cap 214 during rotation. In some embodiments, the longitudinal axis 208 of the fastener 204 is not coaxial with the longitudinal axis 220 of the cap 214 during rotation.

In some embodiments, the fastener head 210 and the cap 214 can pivot relative to each other. In some embodiments, the fastener head 210 and the cap 214 can have polyaxial movement therebetween. In some embodiments, a degree of pivoting can be permitted between the fastener 204 and the cap 214 when the fastener 204 is disposed within the cap 214. The interior surface 222 of the cap 214 distal to the lip 230 can be sized to allow polyaxial movement between the fastener 204 and the cap 214. The polyaxial movement can include any angulation between the fastener head 210 and the cap 214. As described herein, the fastener 204 can have the longitudinal axis 208 and the cap 214 can have the longitudinal axis 220. The longitudinal axis 208 of the fastener 204 can form any angle with the longitudinal axis 220 of the cap 214 during polyaxial movement. The angle can be 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, 120 degrees, 150 degrees, 180 degrees, 210 degrees, 240 degrees. 270 degrees, between 0 and 30 degrees, between 30 and 60 degrees, between 60 and 90 degrees, greater than 90 degrees, greater than 120 degrees, greater than 150 degrees, etc. The longitudinal axis 208 of the fastener 204 can be skewed relative to the longitudinal axis 220 of the cap 214.

The design of the fastener head 210 and the cap 214 can facilitate translation between the fastener head 210 and the cap 214. The design of the fastener head 210 and the cap 214 can facilitate rotation between the fastener head 210 and the cap 214. The design of the fastener head 210 and the cap 214 can facilitate polyaxial movement or pivoting between the fastener head 210 and the cap 214.

The fastener 204 can include a middle section 236. The middle section 236 can be disposed between the fastener head 210 and the thread 206. The middle section 236 can be disposed within fixation device 100 when the fixation device is implanted within the fifth metatarsal. The middle section 236 can be disposed within the threaded portion 142 of the fixation device 100 when the fastener 204 is coupled to the fixation device 100. The middle section 236 can be disposed within the second threaded section 146 of the threaded portion 142 of the fixation device 100, as described herein. The fastener 204 can include a lumen 240. The lumen 240 can allow the fastener 204 to be inserted over a guide wire, as described herein. The lumen 240 can allow the end cap 202 to be inserted over a guide wire, as described herein.

Figure 9:
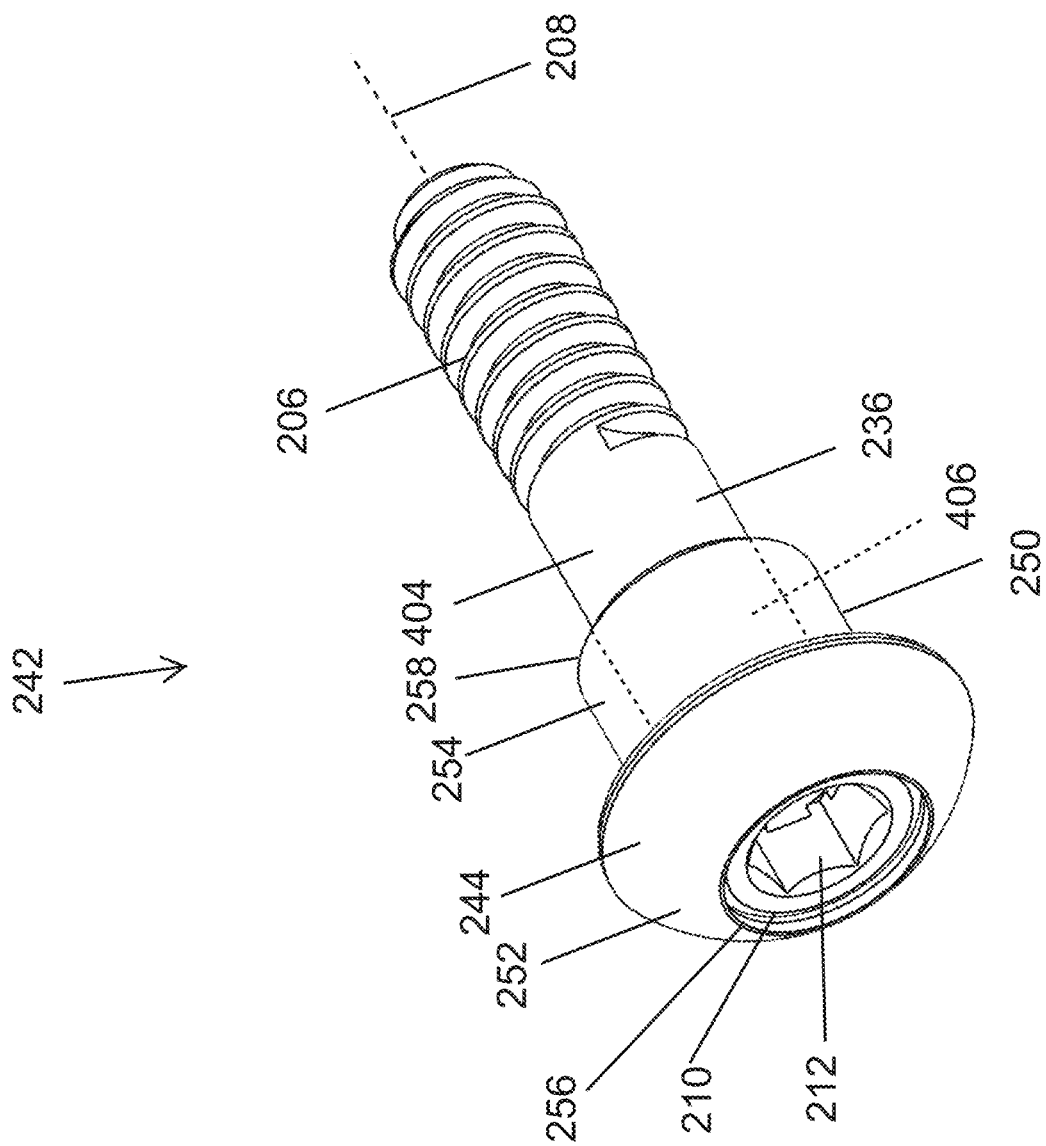
FIG. 9 is a perspective view of a second embodiment of an end cap.
Figure 10:
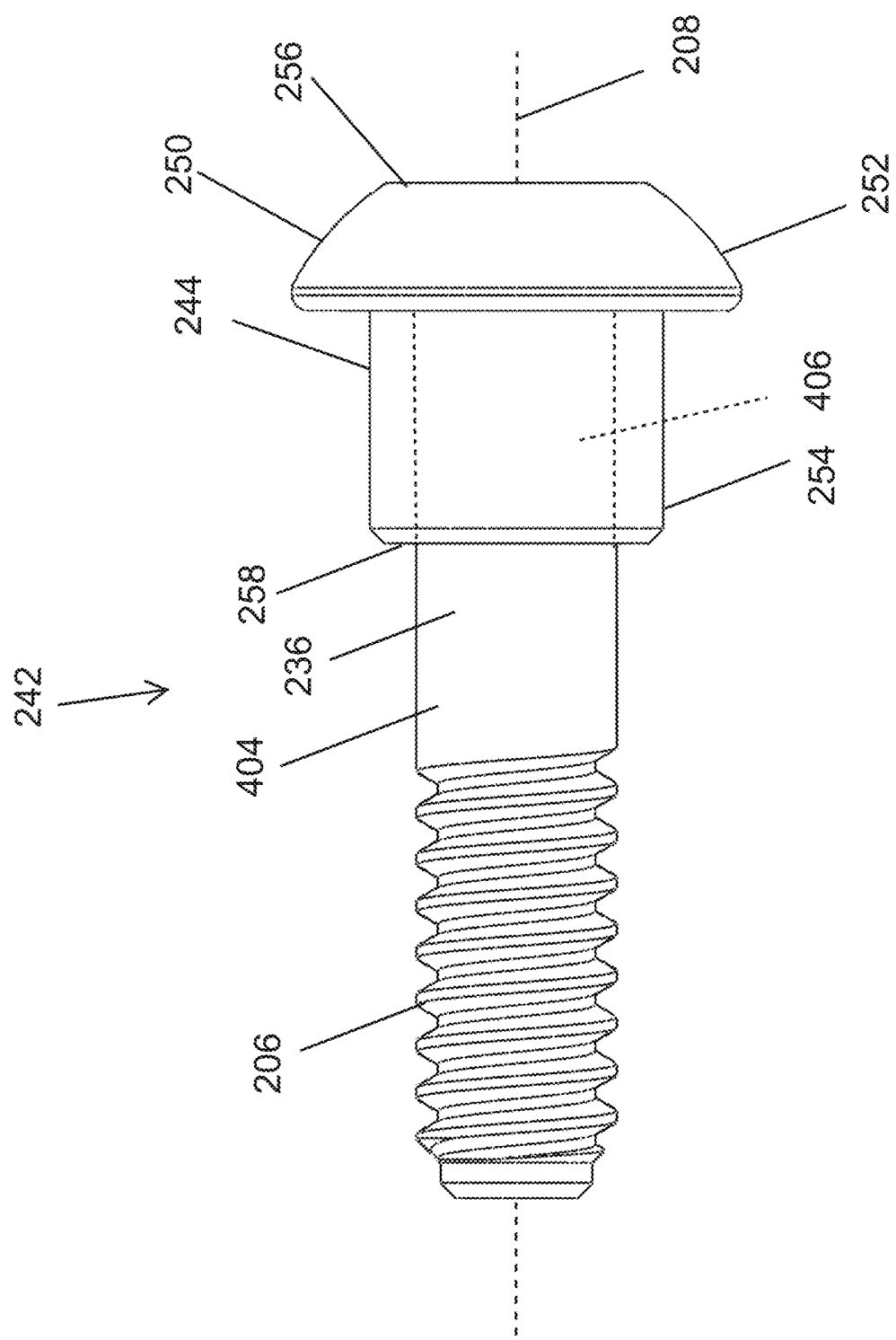
FIG. 10 is a side view of the end cap of FIG. 9.

FIGS. 9 and 10 show a second embodiment of an end cap 242. The end cap 242 can include any of the features of the end cap 202. The end cap 242 can include a long fastener 404. The long fastener 404 can include any of the features of the fastener 204 described herein. The long fastener 404 can include the thread 206. The thread 206 can engage the first threaded portion 144 of the fixation device 100, as shown in FIG. 6. The long fastener 404 can include the fastener head 210. The fastener head 210 can include the socket 212. The long fastener 404 can have the longitudinal axis 208. The long fastener 404 can include the middle section 236. The long fastener 404 can include a length extending section 406. The length extending section 406 can be disposed between the middle section 236 and the fastener head 210. The length extending section 406 can increase the length of the long fastener 404 along the longitudinal axis 208. The length extending section 406 is shown in dashed lines, since the length extending section 406 is disposed within a cap 244.

The end cap 242 can include the cap 244. The cap 244 can include any of the features of the cap 214. The cap 244 can include an interior surface 246 (not shown). The interior surface 246 can match or substantially match the interior surface 222 shown in FIG. 8. The cap 244 can include a mechanism to retain the fastener 404, such as lip 230 shown in FIG. 8. The interior surface 246 can include any of the features described herein to allow translation, rotation, and/or polyaxial movement between the fastener head 210 and the cap 244.

The cap 244 can include an exterior surface 250. The exterior surface 250 can include a first section 252 and second section 254. The cap 244 can include a proximal end 256 and a distal end 258. The first section 252 can be located proximal to the second section 254. The first section 252 of the exterior surface 250 can be curved. The first section 252 of the exterior surface 250 can be spherical or generally spherical. The first section 252 of the exterior surface 250 can be conical or generally conical. In some embodiments, the first section 252 of the exterior surface 250 can be tapered outward from the proximal end 256 of the cap 244 toward the distal end 258 of the cap 244.

The second section 254 can increase the length of the cap 244. In some embodiments, the length of the second section 254 can correspond to the length of the length extending section 406 of the long fastener 404. The second section 254 can include a cylindrical boss. The second section 254 can include any shape including cylinder, triangular prism, triangular pyramid, cube, square prism, square pyramid, rectangular prism, sphere, cone, hexagonal prism, polygonal prism, polygonal pyramid, etc. The second section 254 can extend distally from the first section 252. In some embodiments, the second section 254 limits polyaxial movement between the fastener 204 and the cap 244. In some embodiments, the second section 254 abuts the proximal end 102 of the fixation device 100.

The length extending section 406 of the long fastener 404 can be disposed within the second section 254 of the cap 244 when the fastener 404 is disposed within the cap 244. The middle section 236 of the long fastener 404 can extend from the second section 254 of the cap 244 when the fastener 404 is disposed within the cap 244. The middle section 236 of the long fastener 236 can be disposed the second threaded section 146 when the fastener 404 is coupled to the fixation device 100. The fastener head 210 can be disposed within the first section 252 when the fastener 404 is disposed within the cap 244.

Figure 11:
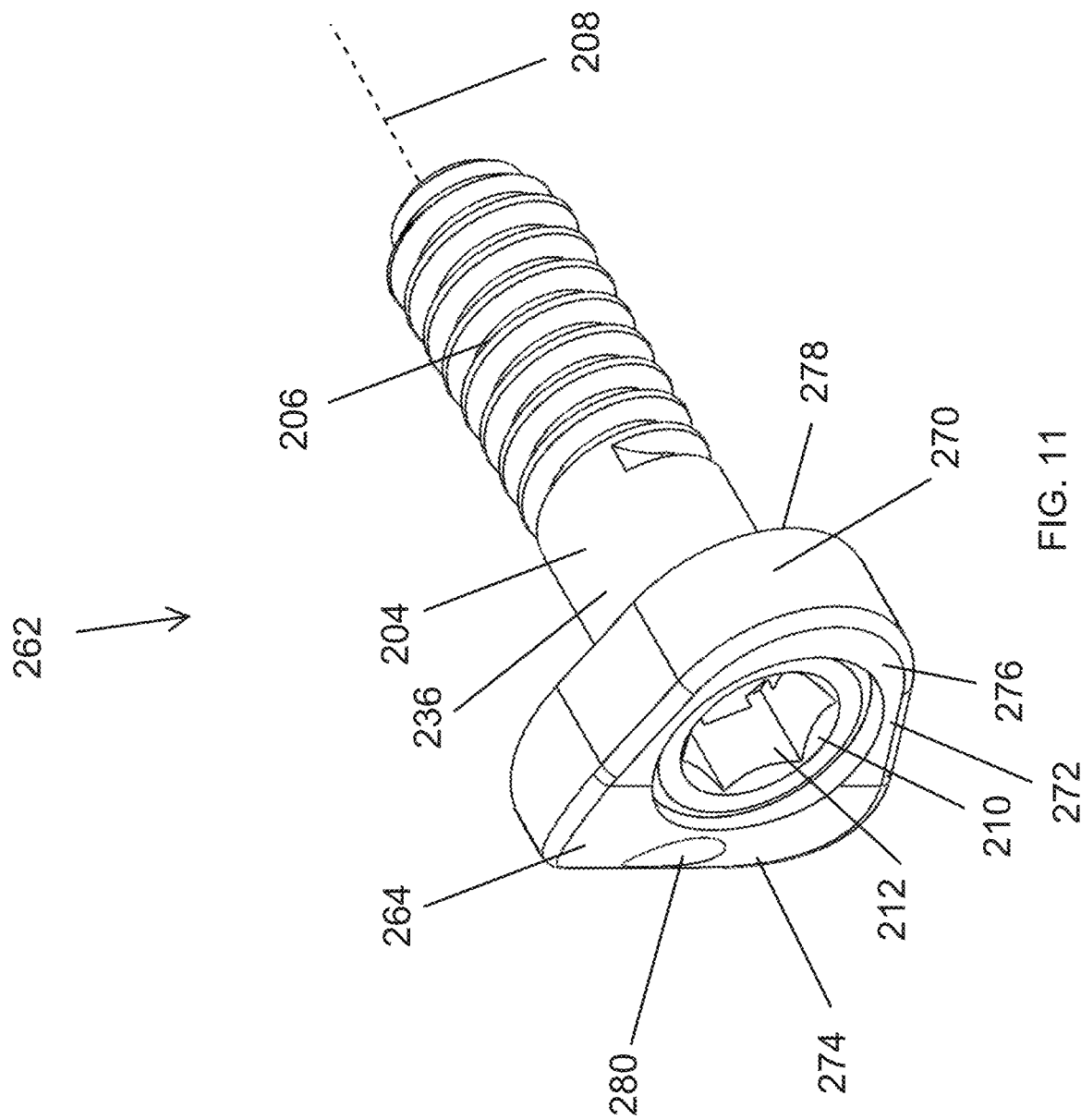
FIG. 11 is a perspective view of a third embodiment of an end cap.
Figure 12:
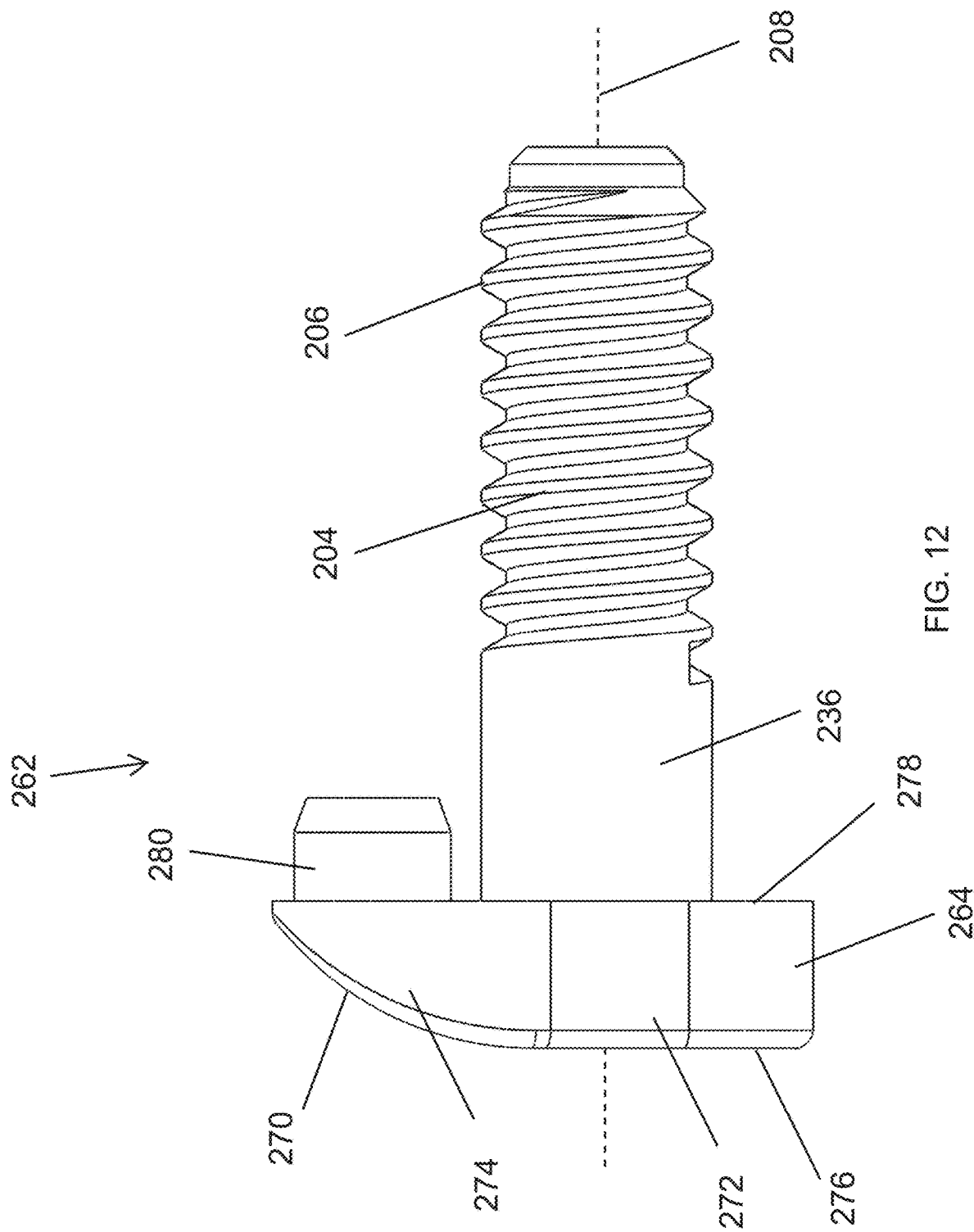
FIG. 12 is a side view of the end cap of FIG. 11.

FIGS. 11 and 12 show a third embodiment of an end cap 262. The end cap 262 can include any of the features of the end caps 202, 242. The end cap 262 can include the fastener 204. In some embodiments, the end cap 262 can include the long fastener 404. The fastener 204 can include the thread 206, the fastener head 210 with the socket 212, and middle section 236. The fastener 202 can have the longitudinal axis 208. The end cap 262 can include the cap 264. The cap 264 can include any of the features of the cap 214. The cap 264 can include an interior surface 266 (not shown). The interior surface 266 can match or substantially match the interior surface 222 shown in FIG. 8. The cap 264 can include a mechanism to retain the fastener 204, such as lip 230 shown in FIG. 8. The interior surface 266 can include any of the features described herein to allow translation, rotation, and/or polyaxial movement between the fastener head 210 and the cap 264.

The cap 264 can include an exterior surface 270. The cap 264 can include a proximal end 276 and a distal end 278. When viewed from the proximal end 276, the cap 264 can be ovoid. When viewed from the proximal end 276, the cap 264 can have a generally circular, oval, elliptical or other rounded shaped. Other configurations are contemplated. When viewed from the proximal end 276, the cap 264 can have a triangular, rectangular, square or other polygonal shape.

The cap 264 can include a first section 272 and a second section 274. The first section 272 and the second section 274 can be at the same longitudinal position along the longitudinal axis 208. The first section 272 can receive the fastener head 210. The first section 272 can include the interior surface 266. The maximum diameter of the second section 274 can be larger than the maximum diameter of the first section 272. The second section 274 can taper from the proximal end 276 of the cap 264 to the distal end 278 of the cap 264. The second section 274 can form a smooth arc from the proximal end 276 of the cap 264 to the distal end 278 of the cap 264. The second section 274 can be designed to engage an anatomical feature or landmark as described herein. The second section 274 can be designed to match or substantially match the anatomy of a patient.

The cap 264 can include a projection 280. The projection 280 can be located in the second section 274. The projection 280 can include a cylindrical projection. The projection 280 can include any shape including cylinder, triangular prism, triangular pyramid, cube, square prism, square pyramid, rectangular prism, sphere, cone, hexagonal prism, polygonal prism, polygonal pyramid, etc. The projection 280 can extend distally from the cap 262. The projection 280 can extend distally from the second section 274. The projection 280 can be designed to engage an anatomical feature or landmark.

Figure 13:
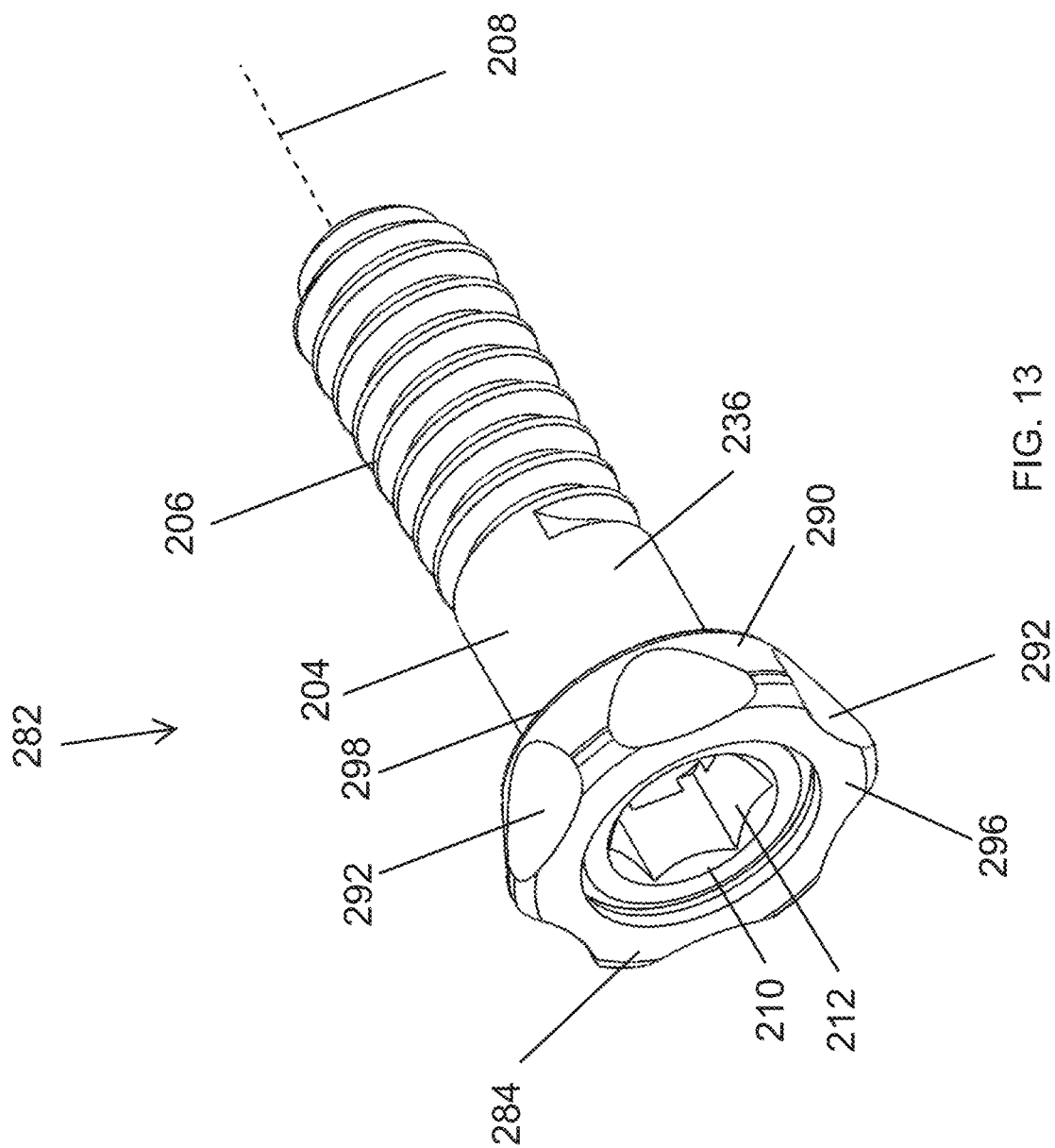
FIG. 13 is a perspective view of a fourth embodiment of an end cap.
Figure 14:
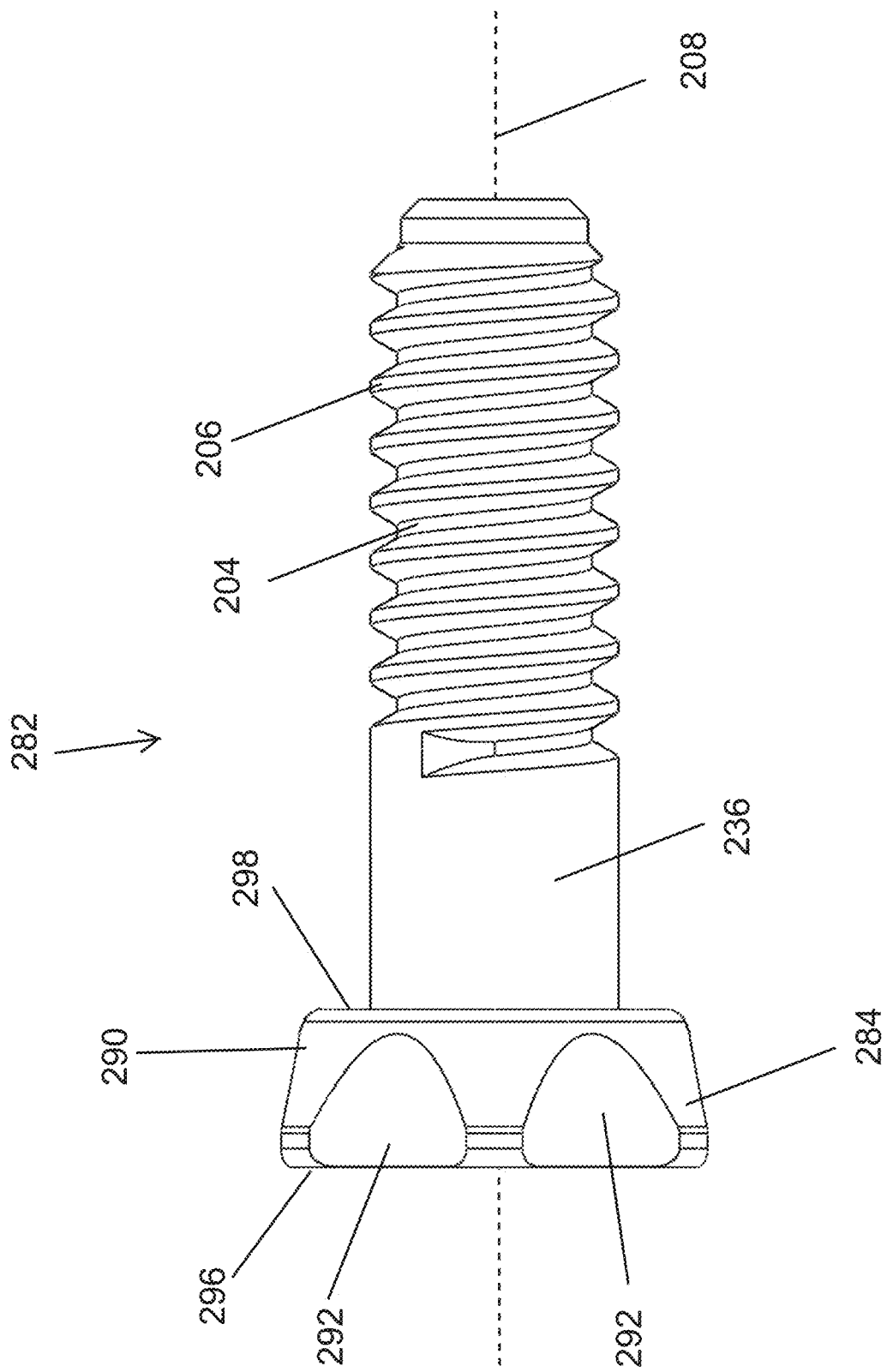
FIG. 14 is a side view of the end cap of FIG. 13.

FIGS. 13 and 14 show a fourth embodiment of an end cap 282. The end cap 282 can include any of the features of the end cap 202, 242, 262. The end cap 282 can include the fastener 204. In some embodiments, end cap 282 can include the long fastener 404. The fastener 204 can include the thread 206, the fastener head 210 with the socket 212, and the middle section 236. The fastener 204 can have the longitudinal axis 208. The end cap 282 can include the cap 284. The cap 284 can include any of the features of the cap 214. The cap 284 can include an interior surface 286 (not shown). The interior surface 286 can match or substantially match the interior surface 222 shown in FIG. 8. The cap 284 can include a mechanism to retain the fastener 204, such as lip 230 shown in FIG. 8. The interior surface 286 can include any of the features described herein to allow translation, rotation, and/or polyaxial movement between the fastener head 210 and the cap 284.

The cap 284 can include an exterior surface 290. The cap 284 can include a proximal end 296 and a distal end 298. The exterior surface 290 of the cap 284 can be curved. The exterior surface 290 of the cap 284 can be spherical or generally spherical. The exterior surface 290 of the cap 284 can be conical or generally conical. In some embodiments, the exterior surface 290 of the cap 284 can tapered inward from the proximal end 296 of the cap 284 to the distal end 298 of the cap 284. In some embodiments, the diameter of the exterior surface 290 near the proximal end 296 of the cap 284 is greater than a diameter of the exterior surface 290 near the distal end 298 of the cap 284. The cap 284 can be cylindrical or generally cylindrical.

The exterior surface 290 of the cap 284 can include one or more grooves 292. In the illustrated embodiment, the cap 284 can include six grooves, but other configurations are contemplated (e.g., one groove, two grooves, three grooves, four grooves, five grooves, seven grooves, eight grooves, nine grooves, ten grooves, a plurality of grooves, etc.). In the illustrated embodiment, each groove 292 is the same. The groove 292 can extend from the proximal end 286 or near the proximal end 296. The groove 292 can be triangular, square, or other polygonal shape. The groove 292 can be tapered from the proximal end 296 to the distal end 298. The grooves 292 can include one or more sharpened edges. The one or more grooves 292 can allow the cap to self-countersink. The one or more grooves 292 can function as a cutting surface to drive the cap 284 into bone. The cap 284 can be considered a headless cap. The cap 284 can include one or more features that allow the cap 284 to advance into the bone.

Figure 15:
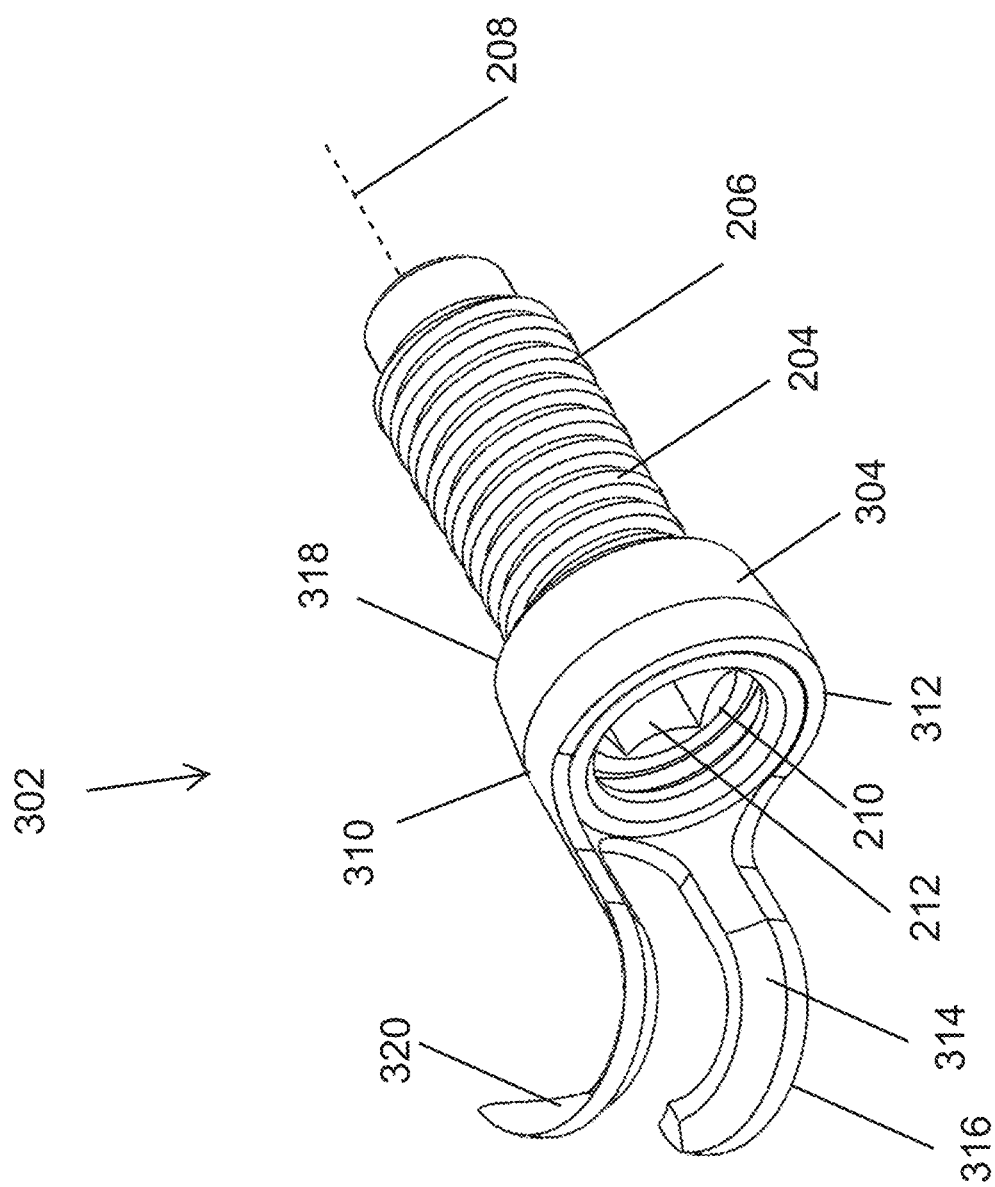
FIG. 15 is a perspective view of a fifth embodiment of an end cap.
Figure 16:
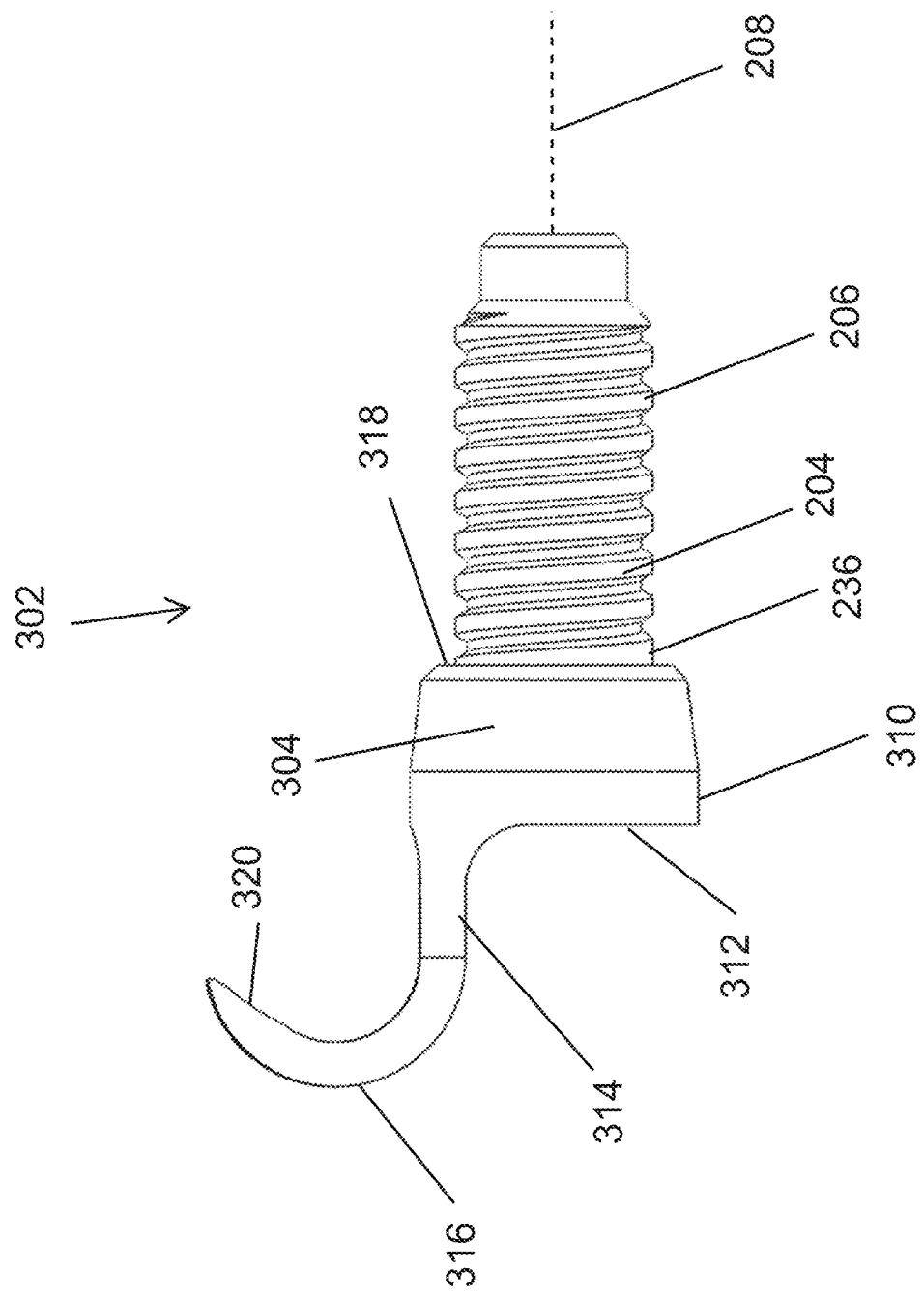
FIG. 16 is a side view of the end cap of FIG. 15.

FIGS. 15 and 16 show a fifth embodiment of an end cap 302. The end cap 302 can include any of the features of the end cap 202, 242, 262, 282. The end cap 302 can include the fastener 204. In some embodiments, end cap 302 can include the long fastener 404. The fastener 204 can include the thread 206, the fastener head 210 with the socket 212, and the middle section 236. The middle section can be disposed within the end cap 302. The fastener 202 can have the longitudinal axis 208. The end cap 302 can include the cap 304. The cap 304 can include any of the features of the cap 214. The cap 304 can include an interior surface 306 (not shown). The interior surface 306 can match or substantially match the interior surface 222 shown in FIG. 8. The cap 304 can include a mechanism to retain the fastener 204, such as lip 230 shown in FIG. 8. The interior surface 266 can include any of the features described herein to allow translation, rotation, and/or polyaxial movement between the fastener head 210 and the cap 304. The middle section 236, or a portion thereof, can be disposed within the cap 304.

The cap 304 can include an exterior surface 310. The cap 304 can include a first section 312 and a second section 314. The cap 304 can include a proximal end 316 and a distal end 318. The first section 312 can receive the fastener head 210. The first section 312 can include the interior surface 306. The first section 312 can be cylindrical or generally cylindrical. The first section 312 can be curved. The first section 312 can be spherical or generally spherical. The first section 312 can be conical or generally conical. In some embodiments, the first section 312 can taper inward toward the distal end 318 of the cap 304.

The second section 314 can include one or more hooks 320. The second section 314 can extend proximally from the first section 312. Each hook 320 can extend proximally toward an apex and then curve distally from the apex. The hook 320 can be formed of a strip. The hook 320 can include a compound bend. The hook 320 can form a first curve in the proximal distal direction. The hook 320 can form a second curve by flaring outward or tapering inward. The hook 320 can include one or more sharpened edges. The hook can include a pointed tip. The hook 320 can be designed to engage an anatomical feature or landmark. The hooks 320 can increase purchase of the end cap 304 in the head of the bone.

The repair systems described herein can have the following attributes. In some embodiments, the fixation device 100 includes a 5 mm×18 mm hub 120. The fixation device 100 can include three distal sizes: 3 mm, 3.8 mm, 4.5 mm. The fixation device 100 can include a 10 degree bend. The bend can be 1 degree, 2 degrees, 3, degrees, 4 degrees, 5 degrees, 6 degrees, 7 degrees, 8 degrees, 9 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 1 and 10 degrees, between 1 and 20 degrees, between 1 and 30 degrees, greater than 5 degrees, greater than 10 degrees, greater than 15 degrees, greater than 20 degrees, less than 20 degrees, less than 15 degrees, less than 10 degrees, etc. The overall length of the fixation device 100 and/or the repair system 200 can be between 40 mm and 60 mm. The length can be adjusted by varying the distal portion 110.

Any of the end caps described herein can include a length extending section. FIGS. 9 and 10 show an example of a length extending section. The second section 254 can be considered a length extending section. As one example, the second section 254 can include a cylindrical boss. The length extending section can have a greater diameter than the thread 206 of the fastener 204 and the long fastener 404. As described herein, the thread 206 of the fastener 204 and the long fastener 404 can be designed to be inserted within the fixation device 100. The thread 206 can be designed to engage the threaded portion 142 of the fixation device 100. The thread 206 can be designed to engage the first threaded section 144 of the threaded portion 142 of the fixation device 100.

As described herein, the middle section 236 of the fastener 204 and the long fastener 404 can be designed to be inserted within the fixation device 100. The middle section 236 can be designed to be disposed within the threaded portion 142 of the of the fixation device 100 when the fastener 204 is coupled to the fixation device 100. The middle section 236 can be designed to be disposed within the second threaded section 146 of the of the fixation device 100. The middle section 236 can be designed to be disposed within the second threaded section 146 of the threaded portion 142.

Any of the end caps described herein can include the fastener 204 or the long fastener 404. The long fastener 404 can include any of the features of the fastener 204, described herein. The long fastener 404 can include the length extending section 406. The length extending section 406 can be disposed between the middle section 236 and the fastener head 210. The length extending section 406 can increase the length of the long fastener 404 along the longitudinal axis 208. The fastener 204 can be considered a standard fastener.

FIGS. 17-22 show an embodiment of an insertion tool 410. The insertion tool 410 can be designed to couple with the fixation device 100. The insertion tool 410 can be designed to insert the fixation device 100 to the proper depth within bone. The insertion tool 410 can be designed to insert the fixation device 100 to the proper depth based on the corresponding end cap. The insertion tool 410 can be designed to insert the fixation device 100 to the proper depth based on the corresponding cap design or fastener design.

Figure 17:
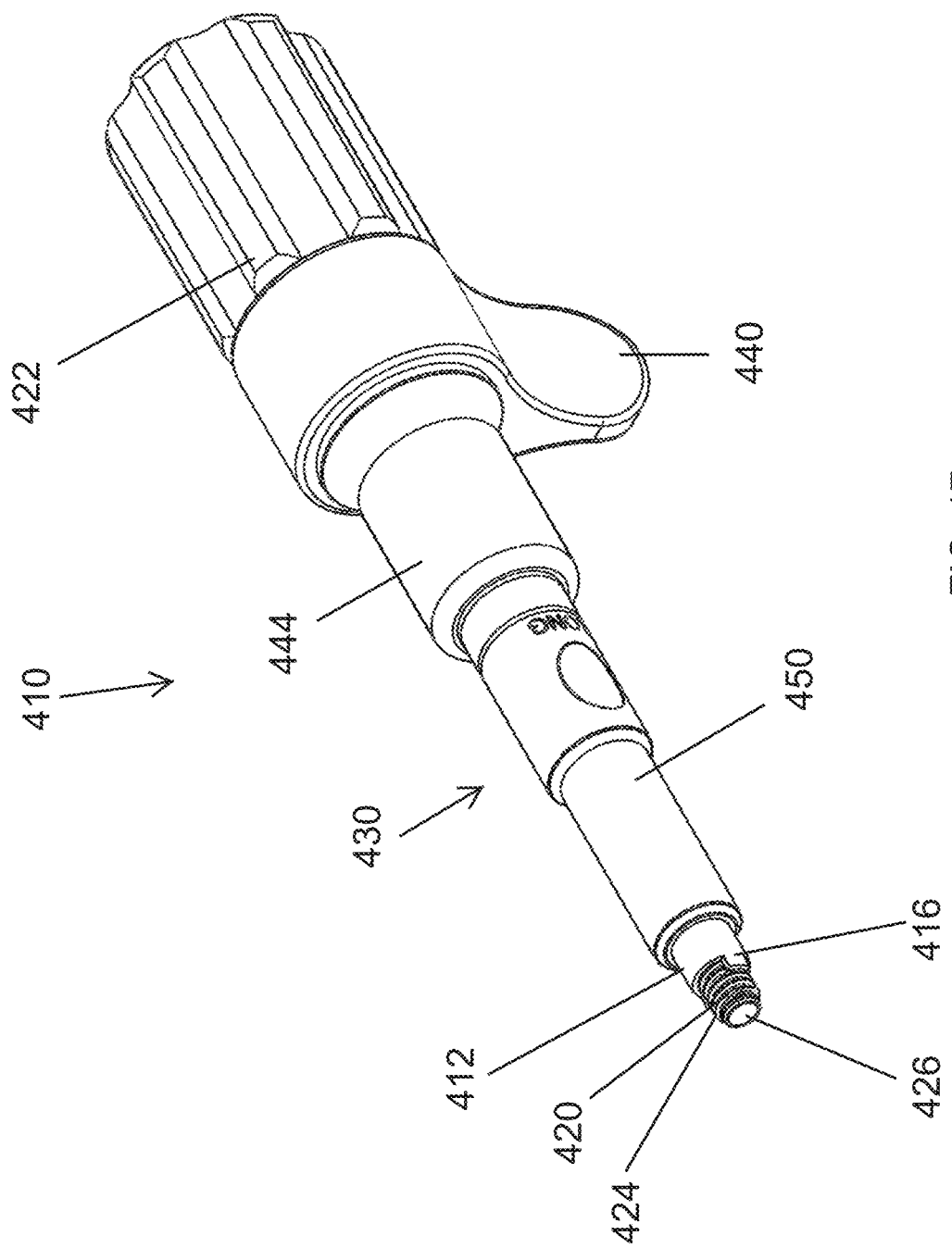
FIG. 17 is a perspective view of an insertion tool.
Figure 18:
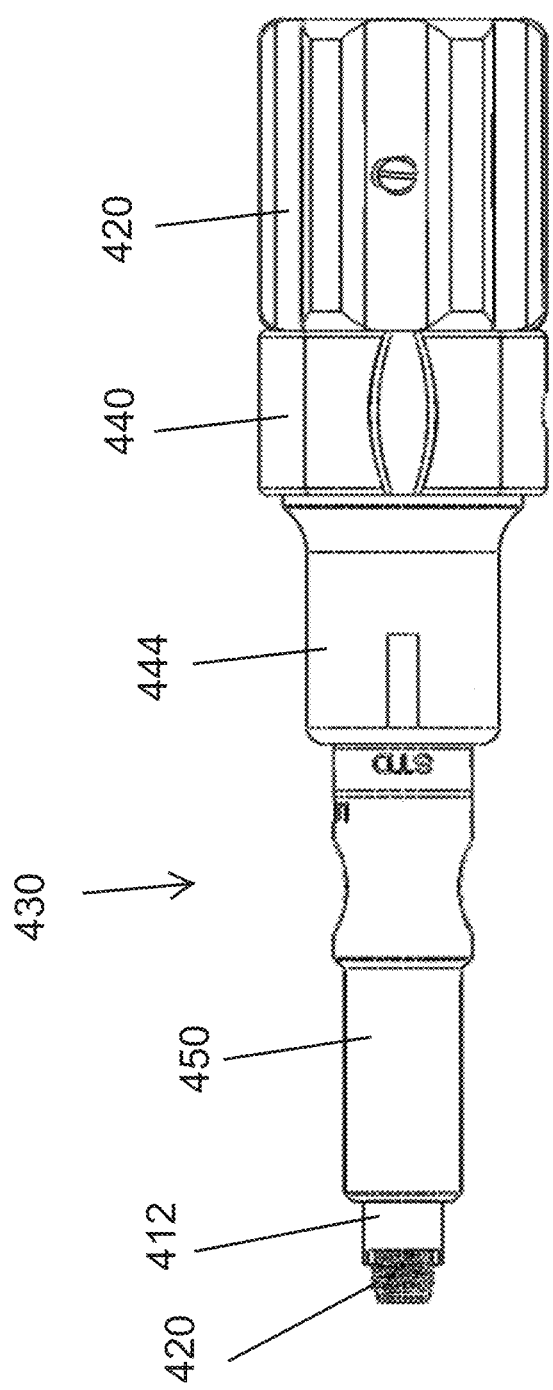
FIG. 18 is a side view of the insertion tool of FIG. 17.
Figure 19:
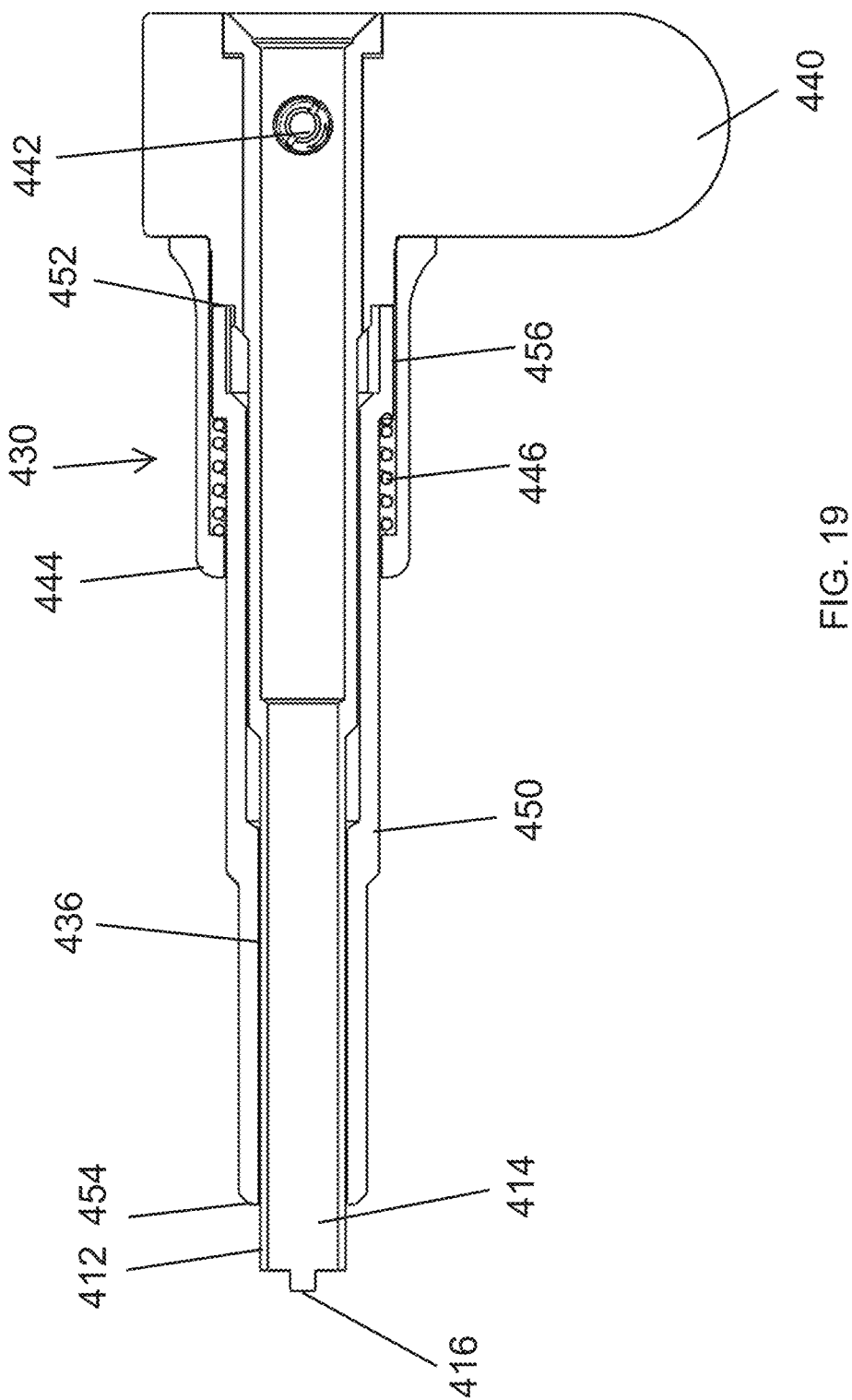
FIG. 19 is a cross-sectional view of components of the insertion tool of FIG. 17.

Referring to FIGS. 17-19, the insertion tool 410 can include an elongate member 412. The elongate member 412 can include a lumen 414, as shown in FIG. 19. The elongate member 412 can include a corresponding engagement member 416. The corresponding engagement member 416 of the insertion tool 410 can be complementary in shape to the engagement member 122 of the fixation device 100. The engagement member 122 and the corresponding engagement member 416 can be an anti-rotation feature between the fixation device 100 and the insertion tool 410. The engagement member 122 can include one or more slots. The corresponding engagement member 416 can be one or more flanges. In the illustrated embodiment, the corresponding engagement member 416 includes a pair of flanges. The corresponding engagement member 416 of the insertion tool 410 can be designed to engage the engagement member 122 of the fixation device 100 to couple the insertion tool 410 to the fixation device 100. The engagement member 122 of the fixation device 100 can be located at a proximal end 102 of the fixation device 100, as shown in FIG. 1.

The insertion tool 410 can include a shaft 420. The shaft 420 can be sized to be disposed within the lumen 414 of the elongate member 412. The shaft 420 can include a handle 422. The handle 422 can rotate the shaft 420 within the lumen 414 of the elongate member 412. The shaft 420 can include a thread 424. The thread 424 can be designed to engage the second threaded section 146 of the fixation device 100, as shown in FIG. 5. The second threaded section 146 can be located near the proximal end 102 of the fixation device 100. In some methods of use, the elongate member 412 engages the fixation device 100 before the shaft 420 engages the fixation device 100. In some methods, the thread 424 of the shaft 420 engages the second threaded section 146 of the fixation device 100 after the corresponding engagement feature 416 of the elongate member 412 engages the engagement member 122 of the fixation device 100. The shaft 420 can be cannulated. The shaft 420 can include the lumen 426.

The insertion tool 410 can include a sleeve 430. The sleeve 430 can include a lumen 436. The elongate member 412 can be disposed within the lumen 436 of the sleeve 430.

The sleeve 430 can include a handle 440. In the illustrated embodiment, the handle 440 can extend from the side surface of the sleeve 430. In some embodiments, the elongate member 412 is fixed relative to the handle 440 of the sleeve 430. Referring to FIG. 19, the insertion tool 410 can include a fastener 442 designed to couple the elongate member 412 and handle 440 of the sleeve 430. The sleeve 430 can include a cover 444. The cover 444 can extend distally from the handle 440. The cover 444 can enclose, or partially enclose, one or more internal components configured to adjust the length of the sleeve 430. The cover 444 can enclose a spring 446.

The sleeve 430 can include a slider 450. The slider 450 can be designed to be pulled by the user. The slider 450 can be designed to translate in the proximal-distal direction. The slider 450 can be designed to rotate with respect to the handle 440. The slider 450 can be designed to translate relative to the elongate member 412. The slider 450 can be designed to rotate with respect to the elongate member 412. The slider 450 can include a proximal end 452 and a distal end 454.

The slider 450 can include one or more flanges 456. The flange 456 can be located at or near the proximal end 452 of the slider 450. In the illustrated embodiment, the slider 450 includes a pair of flanges 456. The distal end 454 of the slider 450 can include a curved or blunt edge. The distal end 454 can be designed to abut bone, as described herein.

Figure 20:
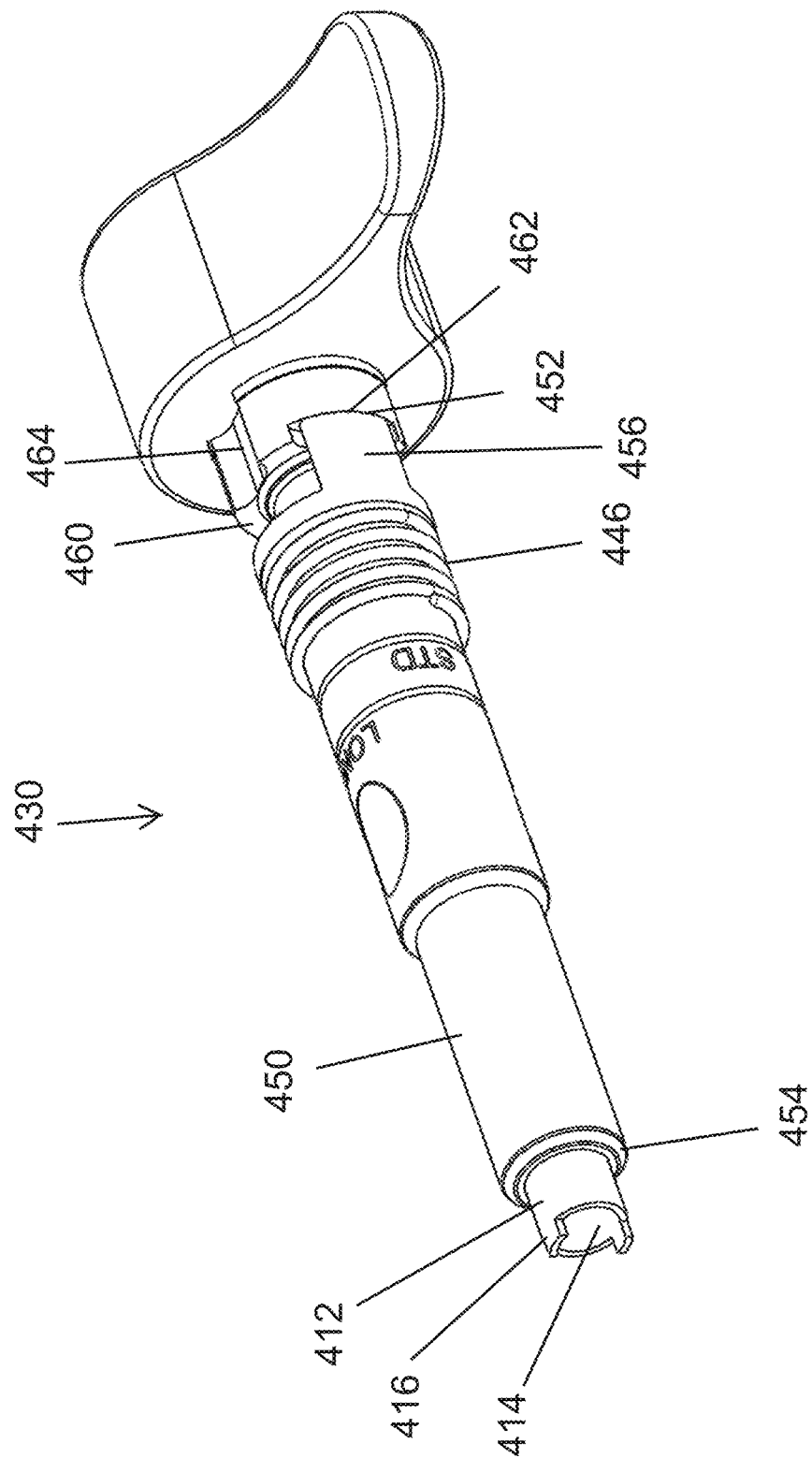
FIG. 20 is a perspective view of components of the insertion tool of FIG. 19 in a standard position.
Figure 21:
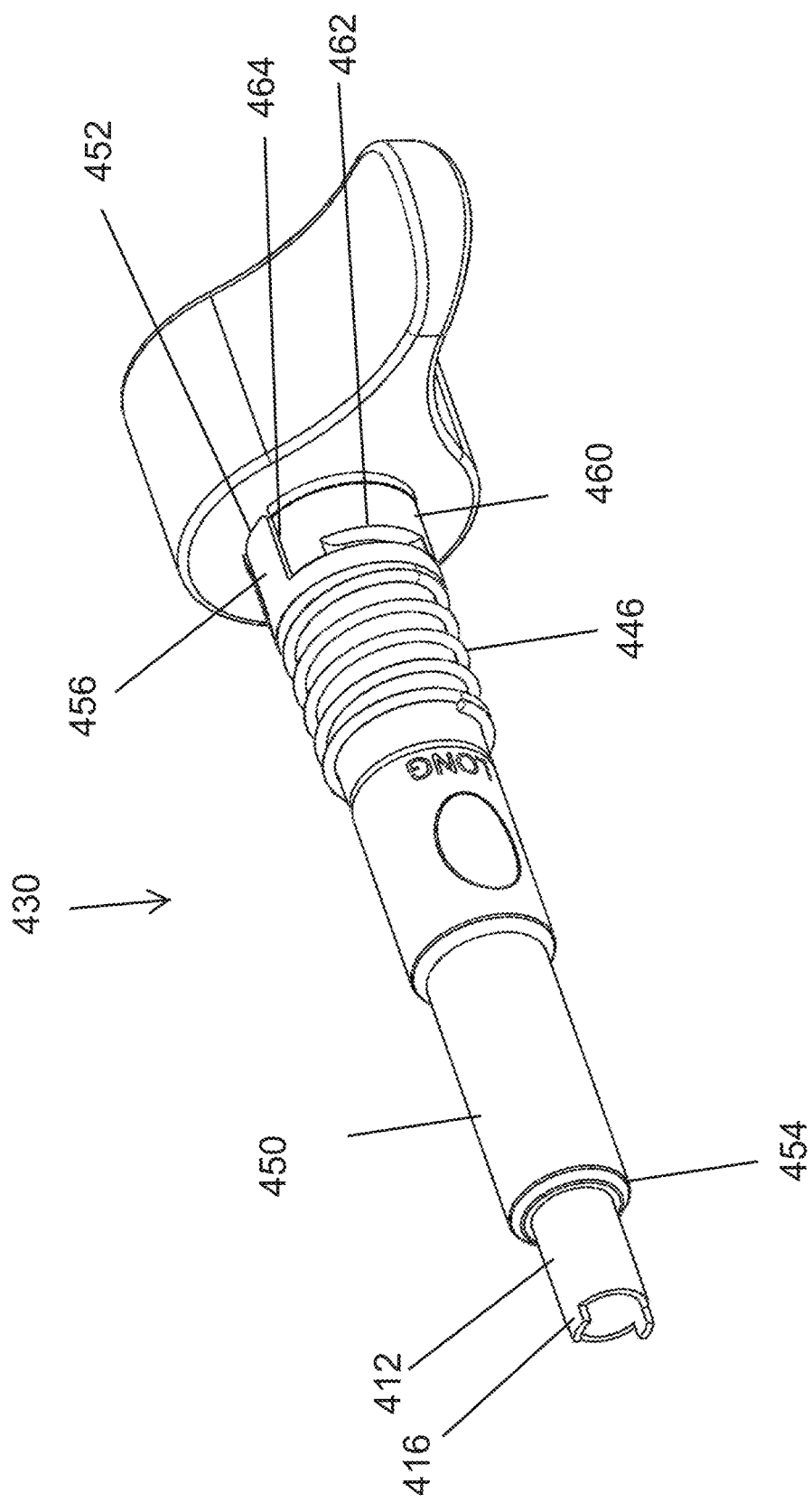
FIG. 21 is a perspective view of components of the insertion tool of FIG. 19 in a long position.

Referring to FIG. 20, the cover 444 has been removed from the sleeve 430. The sleeve 430 can include a block 460. The block 460 can be designed to interact with the proximal end 452 of the slider 450. The block 460 can include one or more grooves 462. The one or more flanges 456 can be disposed in the one or more grooves 462 when the insertion device 410 is in a standard position, as shown in FIG. 20. A single flange 456 can be disposed in a single groove 462 in the standard position. The pair of grooves 462 can be diametrically opposed. The block 460 can include one or more slots 464. The one or more flanges 456 can be disposed in the one or more slots 464 when the insertion device 410 is in a long position, as shown in FIG. 21. A single flange 456 can be disposed in a single slot 464 in the long position. The pair of slots 464 can be diametrically opposed. The spring 446 can bias the flange 456 toward the block 460.

Each groove 462 extends from the distal end of the block 460 to a distance DS. Each slot extends from the distal end of the block 460 to a distance DL. The different between DS and DL can correspond to the length extending section. The different between DS and DL can correspond to the length extending section of a cap. The different between DS and DL can correspond to the length extending section of a fastener. The different between DS and DL can correspond to the difference in length between the fastener 204 and the long fastener 404.

The user can adjust the slider 450 between the standard position and the long position. The method can include one or more of the following steps to move from the standard position to the long position. The user can overcome the biasing force of the spring 446. The user can pull the slider 450 distally. The user can translate the flange 456 relative to the groove 462. The user can translate the flange 456 distally to remove the flange 456 from the groove 462. In some embodiments, the user can rotate the slider 450. The user can rotate the slider 450 approximately ninety degrees. The user can rotate the slider 450 approximately a quarter turn. In some embodiments, the user can rotate the handle 440. The user can rotate the handle 440 approximately ninety degrees. The user can rotate the handle 440 approximately a quartet turn. The user can release the slider 450. The biasing force of the spring 464 can position the flange 456 within the slot 464. The user can adjust the slider 450 between the long position and the standard position by reversing one or more of the previous steps.

The distal end 454 of the slider 450 can change positions between the standard position and the long position. The distal end 454 of the slider 450 can be positioned further away from the corresponding engagement feature 416 in the long position. The slider 450 can expose a greater length of the elongate member 412 in the long position. In the standard position, the distance of the exposed elongate member 412 is ES. In the long position, the distance of the exposed elongate member 412 is EL. The different between ES and EL can correspond to the length extending section of a cap. The different between ES and EL can correspond to the length extending section of a fastener. The different between ES and EL can correspond to the difference in length between the fastener 204 and the long fastener 404. In the standard position, the proximal end 102 of the fixation device 100 can be a distance away from the distal end 454 of the slider 450. In the long position, the proximal end 102 of the fixation device 100 can be further away from the distal end 454 of the slider 450.

Figure 22:
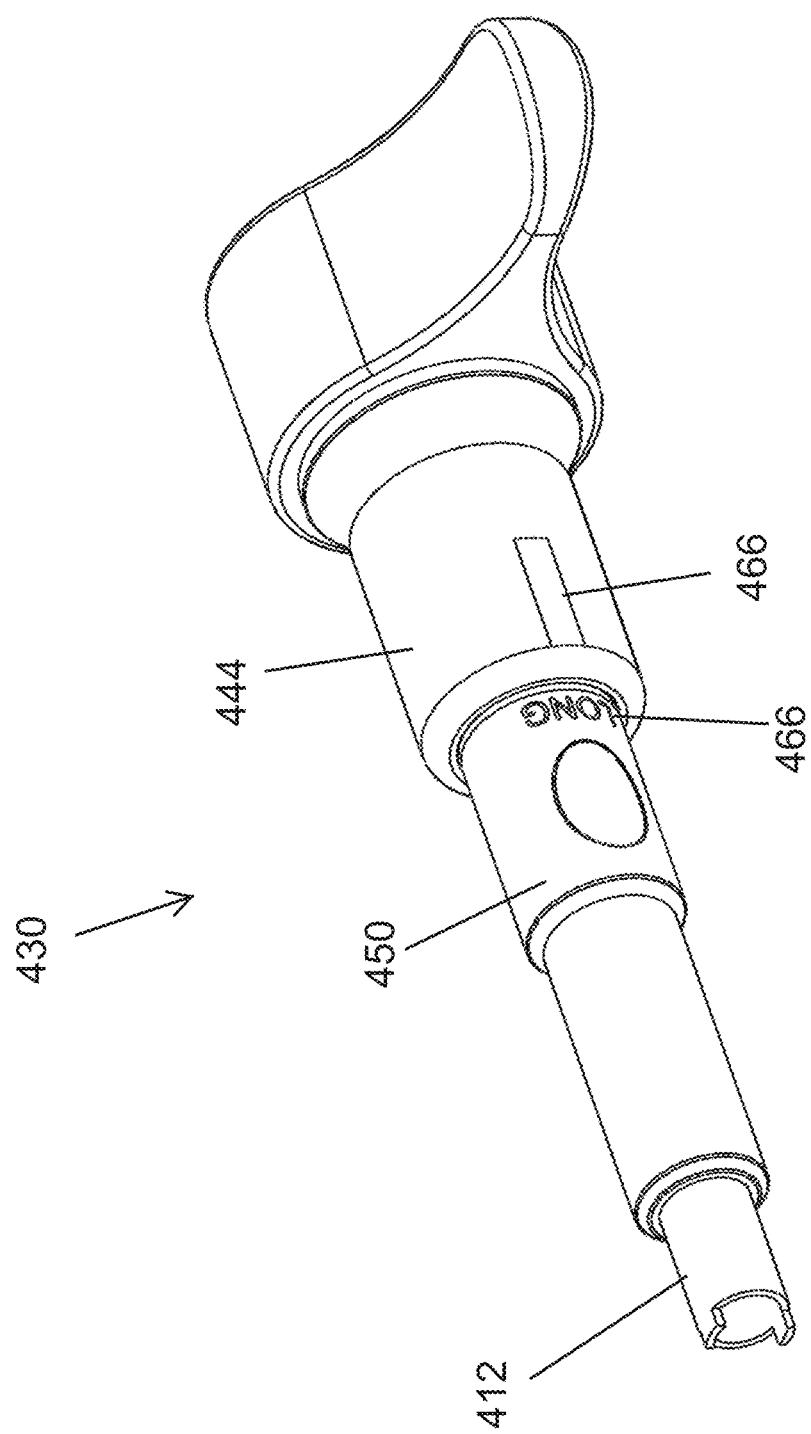
FIG. 22 is a perspective view of components of the insertion tool of FIG. 19 in the long position.
Figure 23:
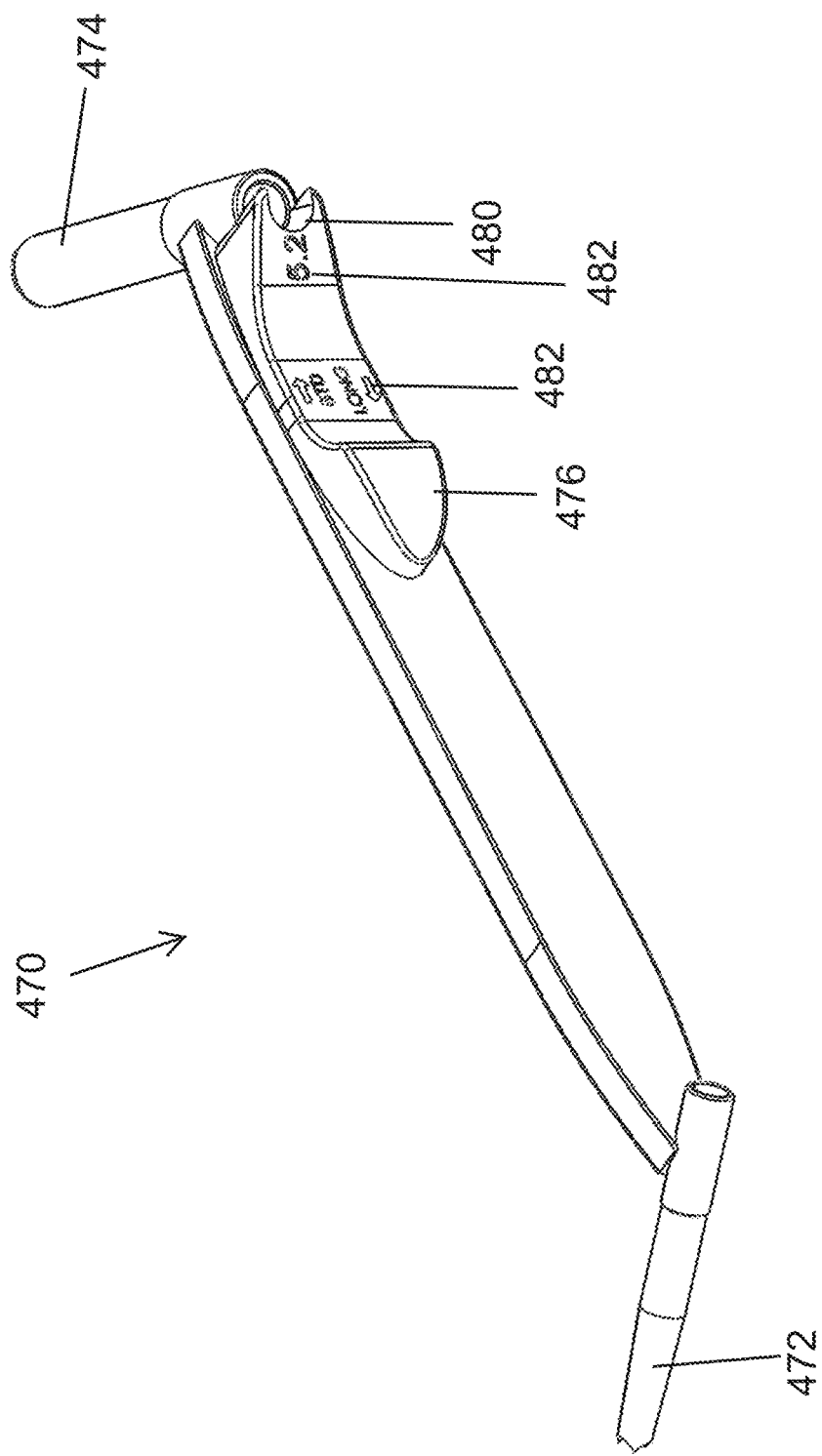
FIG. 23 is a perspective view of a drill guide.
Figure 24:
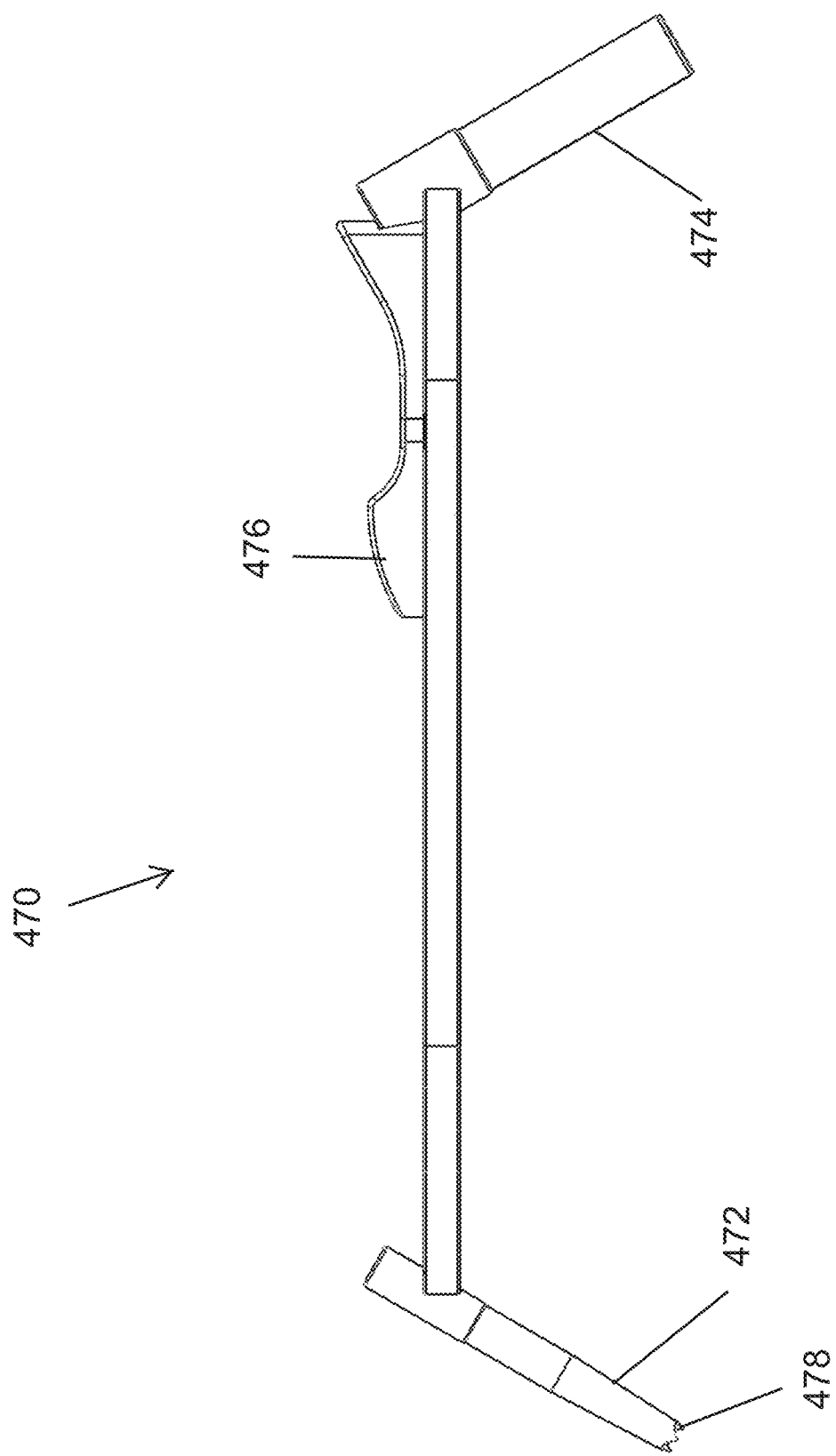
FIG. 24 is a side view of the drill guide of FIG. 23 in a standard position.
Figure 25:
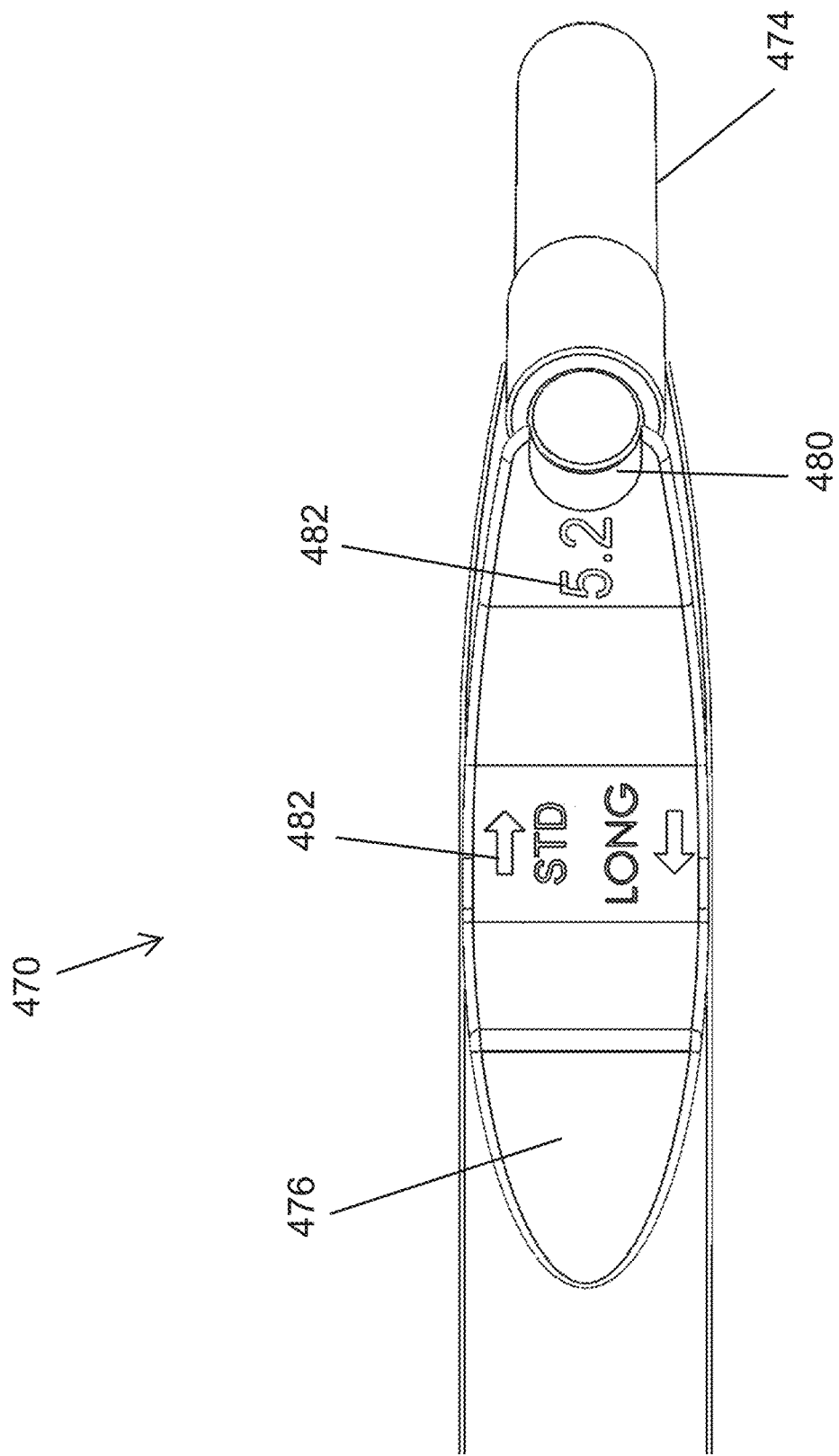
FIG. 25 is a top view of the drill guide of FIG. 23 in the standard position.

Referring to FIG. 22, the sleeve 430 can include one or more markings 466 to indicate whether the sleeve 430 is in the standard position or the long position. The marking 466 can include a symbol, a line, a letter, a word, a color, a protrusion, detent, or any other indicator. In the illustrated embodiment, the cover 444 includes a line. In the illustrated embodiment, the slider 450 includes letters or words (e.g., abbreviation STD, word LONG). The line on the cover 444 can align with the abbreviation STD on the slider 450 in the standard position. The line on the cover 444 can align with the word LONG on the slider 450 in the long position, see FIG. 22. In some embodiments, the elongate member 412 can include one or more markings (not shown).

FIGS. 23-31 show an embodiment of a drill guide 470. The drill guide 470 can include a first cannula 472. The first cannula 472 can be sized to accept a K-wire, as described herein. The first cannula 472 can be angled relative to the drill guide 470. The first cannula 472 can be angled to facilitate placement of the K-wire.

The drill guide 470 can include a second cannula 474. The second cannula 474 can be sized to accept a reamer, as described herein. The second cannula 474 can be sized to accept a 5.2 mm reamer. The second cannula 474 can be angled relative to the drill guide 470. The second cannula 474 can be angled to facilitate placement of the reamer. The first cannula 472 can be located on one side of the drill guide 470 and the second cannula 474 can be located on the opposite side of the drill guide 470. The through axis of the first cannula 472 and the through axis of the second cannula 474 can for an enclosed angle. The enclosed angle can be 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 0 and 30 degrees, between 30 and 60 degrees, between 60 and 90 degrees, greater than 90 degrees, greater than 120 degrees, greater than 150 degrees, etc. The through axis of the first cannula 472 and the through axis of the second cannula 474 can be skewed.

The drill guide 470 can include a slider 476. The slider 476 can change positions between the standard position and the long position. The slider 476 can be positioned closer to the second cannula 474 in the standard position. The slider 476 can be positioned further away from the second cannula 474 in the long position.

FIGS. 23-26 show the slider 470 in the standard position. The slider 476 can include an opening 480. The opening 480 can be curved. The opening 480 can be semi-circular. The slider 470 can include one or more markings 482 to indicate whether the slider 470 is in the standard position or the long position. The marking 482 can include a symbol, a line, a letter, a word, a color, a protrusion, detent, or any other indicator. In the illustrated embodiment, the slider 470 includes an arrow to indicate the direction of movement for slider 470 to be moved to the standard position. In the illustrated embodiment, the slider 470 includes an arrow to indicate the direction of movement for slider 470 to be moved to the long position. The markings 482 can include the abbreviation STD for the standard position and the word LONG for the long position. The markings 482 can include the size of the reamer associated with the second cannula 474.

Figure 26:
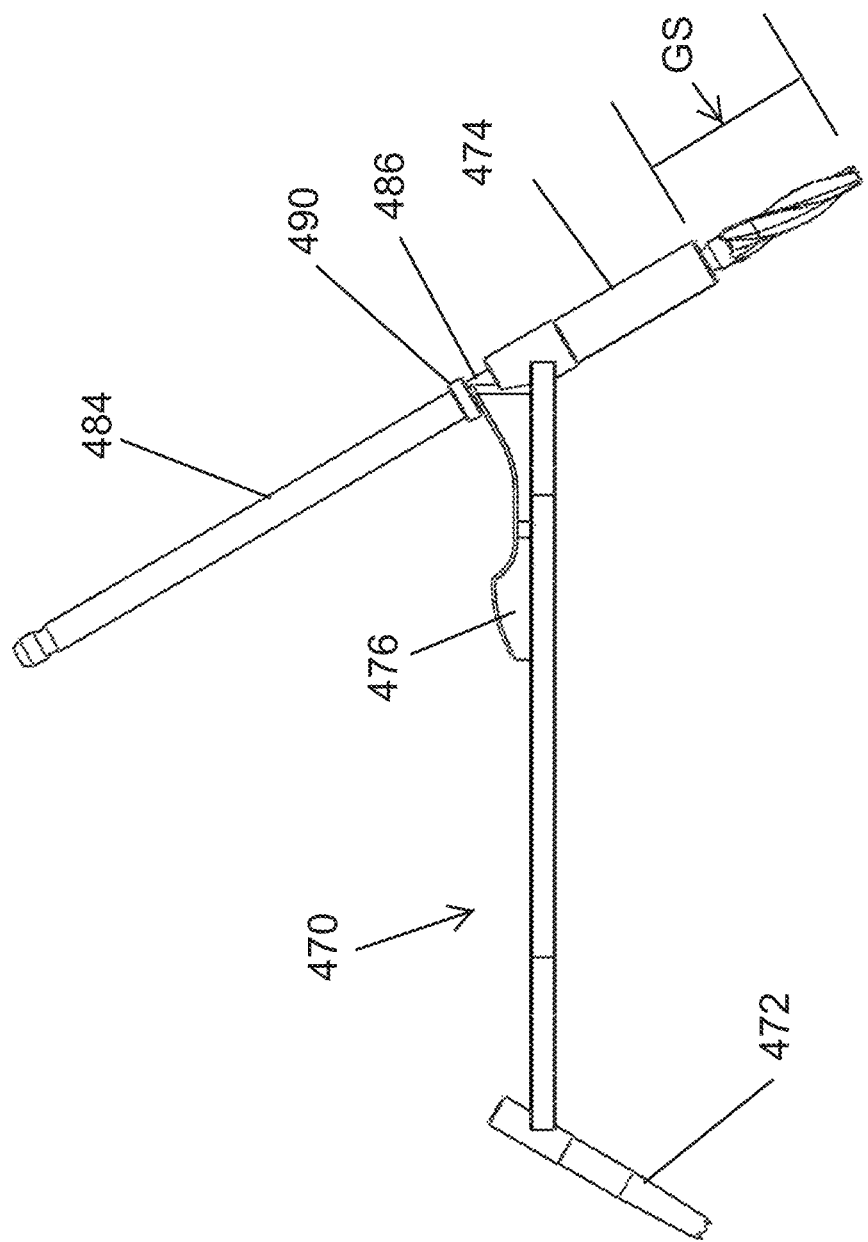
FIG. 26 is a side view of the drill guide of FIG. 23 in the standard position with a reamer.

FIG. 26 shows a reamer 484. The reamer 484 can include a shaft 486. The shaft 486 can be sized to fit within the opening 480 of the slider 476. The opening 480 can accommodate the shaft 486 of the reamer 484, or a portion thereof, when the reamer 484 is disposed within the second cannula 474. The reamer 484 can include a stop 490. The stop 490 can be designed to abut the slider 476. The stop 490 can limit movement of the shaft 486 of the reamer 484 through the opening 480 of the slider 476.

Figure 27:
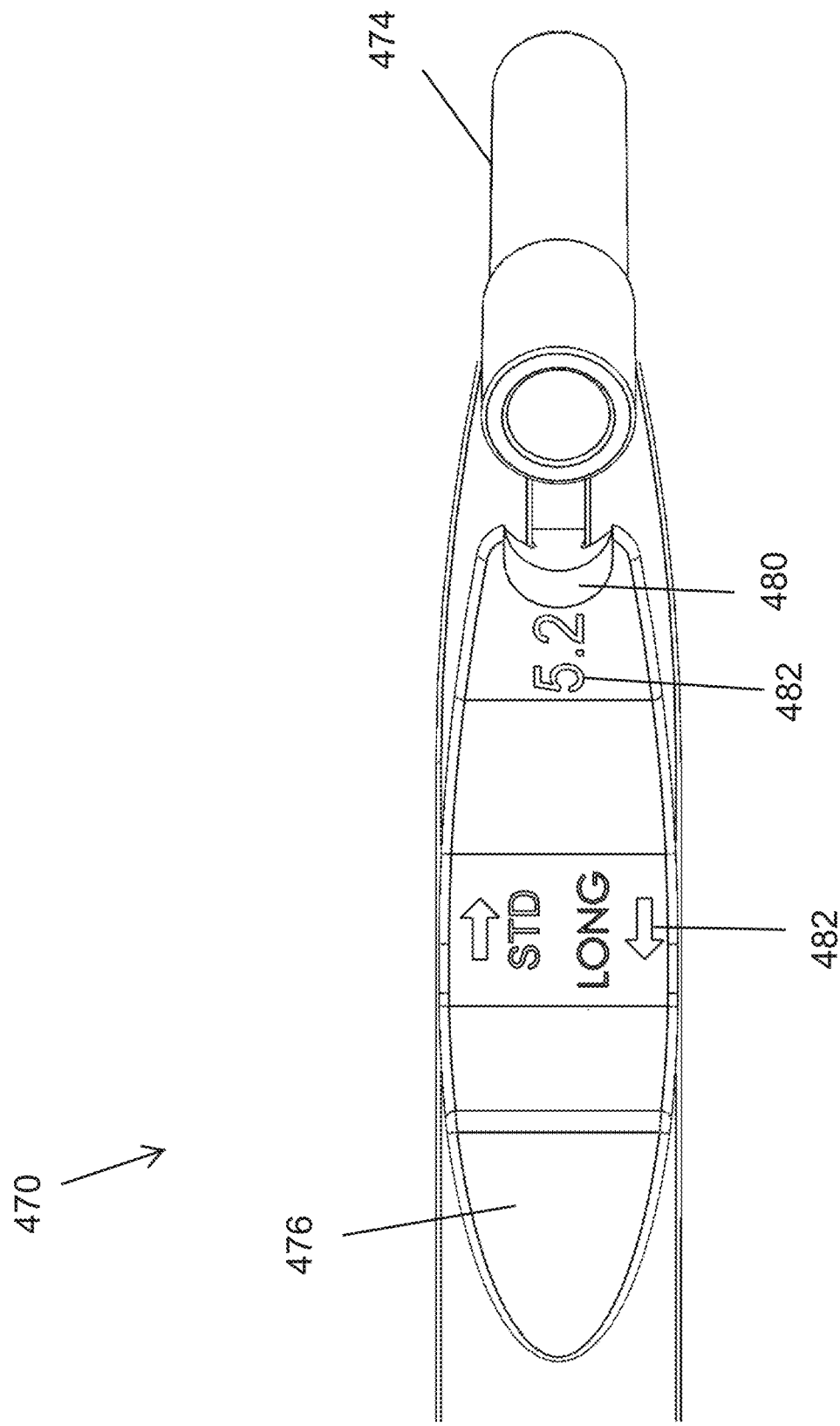
FIG. 27 is a top view of the drill guide of FIG. 23 in a long position.
Figure 28:
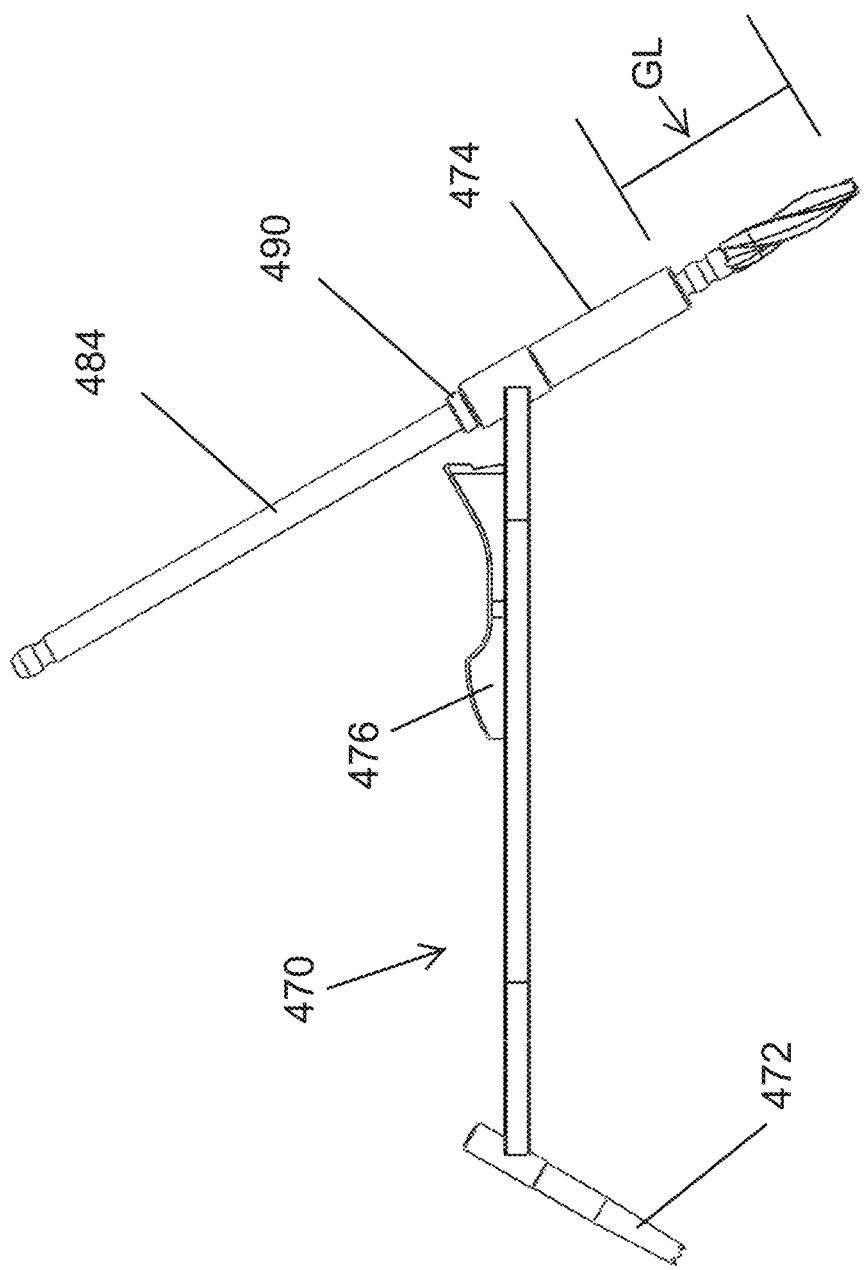
FIG. 28 is a side view of the drill guide of FIG. 23 in the long position.

FIG. 27-28 show the location of the slider 476 in the long position. The reamer 484 can include the stop 490. In the long position, the stop 490 can abut the second cannula 474. The stop 490 does not abut the slider 476. The slider 476 can be positioned away from the reamer 484 when the reamer 484 is positioned within the second cannula 474.

The position of the reamer 484 beyond the second cannula 474 in the standard position is labeled GS. The position of the reamer 484 beyond the second cannula 474 in the long position is labeled GL. The different between GS and GL can correspond to the length extending section of a cap. The different between GS and GL can correspond to the length extending section of a fastener. The different between GS and GL can correspond to the difference in length between the fastener 204 and the long fastener 404. The position of the reamer 484 beyond the second cannula 474 can correspond to a countersink distance. The countersink in the long position can be greater than the countersink in the standard position.

Figure 29:
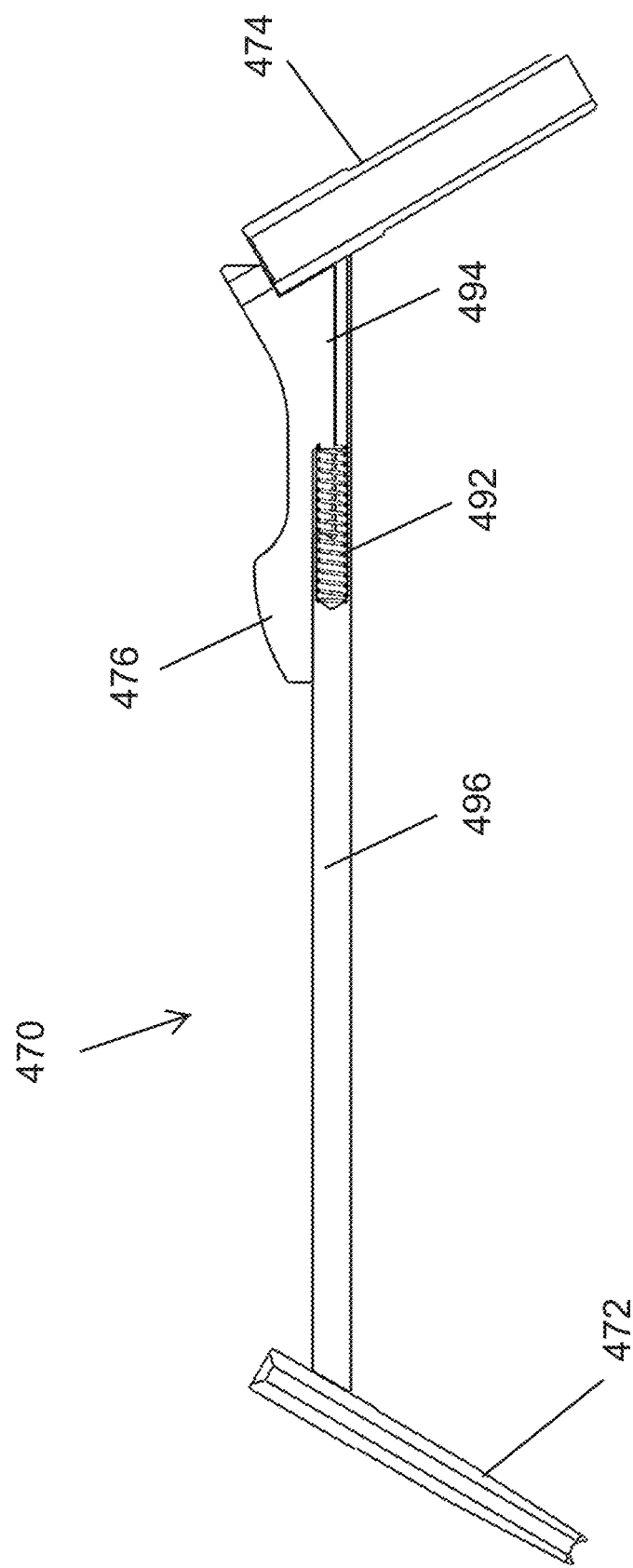
FIG. 29 is a cross-sectional view of the drill guide of FIG. 23 in the standard position.
Figure 30:
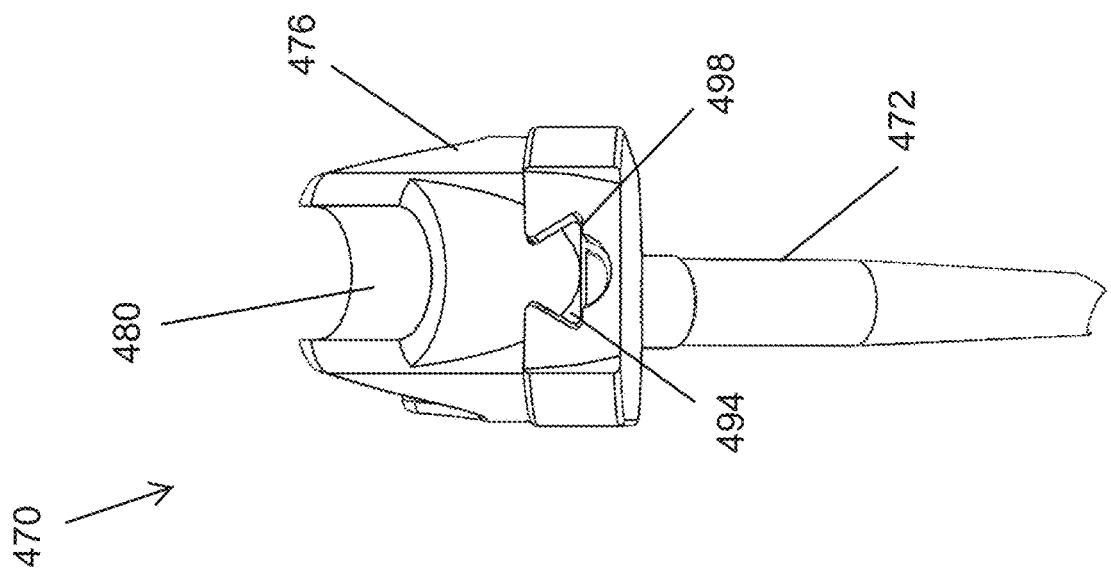
FIG. 30 is another view of the drill guide of FIG. 23.
Figure 31:
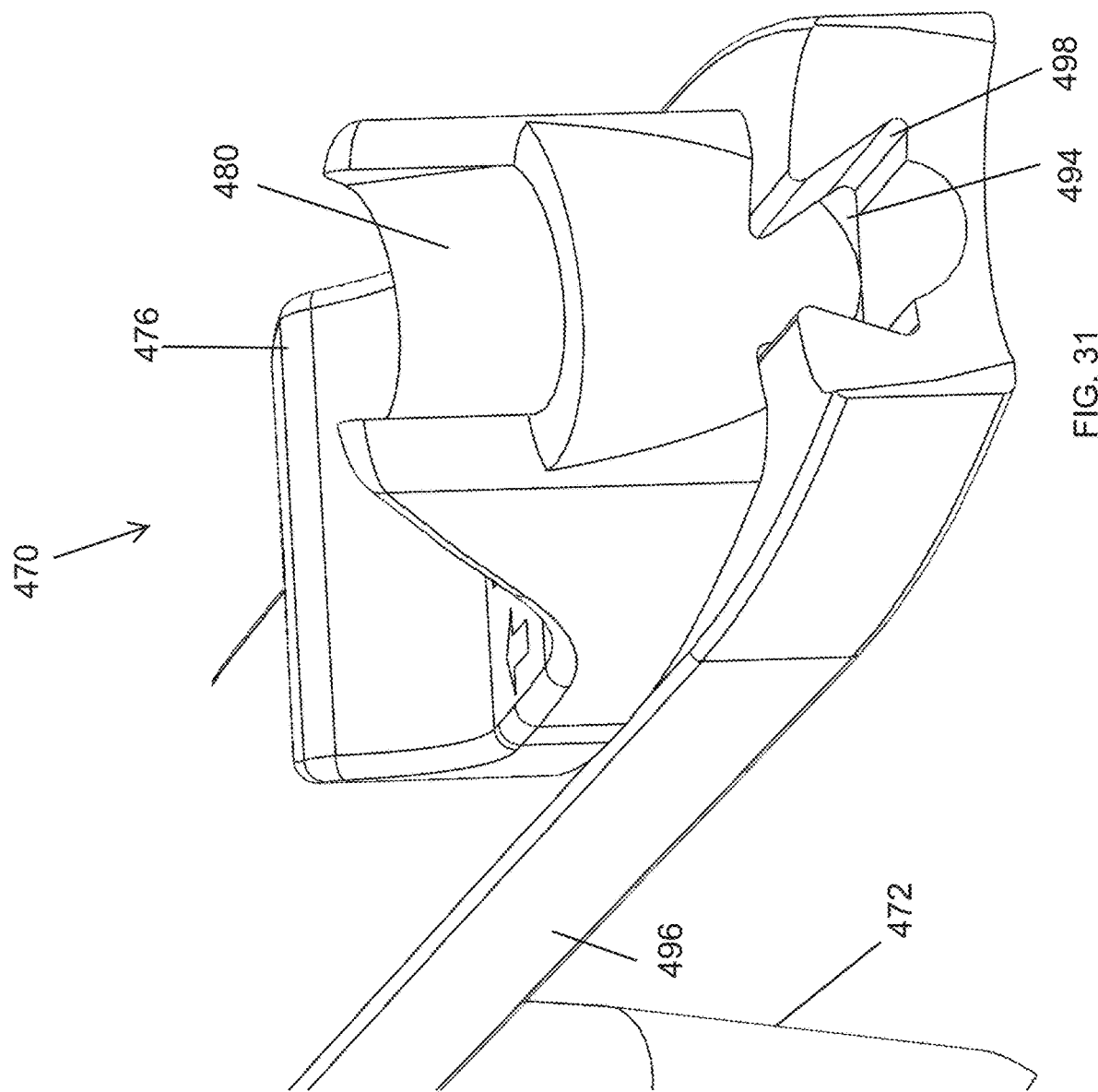
FIG. 31 is a perspective view of the drill guide of FIG. 23.

FIGS. 29-31 show views of the drill guide 470. The drill guide 470 can include a spring 492. The spring 492 can bias the slider 476 toward the standard position. The slider 476 can include a mating feature 494. The mating feature 494 can be a tongue. The mating feature 494 can be a tapered projection. The drill guide 470 can include an arm 496. The arm 496 can couple first cannula 472 and the second cannula 474. The arm 496 can include a corresponding mating feature 498. The corresponding mating feature 498 can be a groove. The corresponding mating feature 498 can be a tapered recess. The mating feature 494 and the corresponding mating feature 498 can form a dovetail joint. The mating feature 494 and the corresponding mating feature 498 can interlock. The mating feature 494 and the corresponding mating feature 498 can allow the slider 476 to slide relative to the arm 496. The mating feature 494 and the corresponding mating feature 498 can prevent disengagement between the slider 476 and the arm 496.

FIGS. 32-44 show various method steps related to the fifth metatarsal. FIGS. 32-39B generally show method steps related to installing repair systems. FIGS. 40-44 generally show method steps related to removing repair systems. A surgical method can include one or more of the following steps. One or more of the following steps can be performed in any order. While the following method steps relate to the fifth metatarsal, one or more the method steps can apply to any bone of the human body.

The fifth metatarsal is a bone of the foot located on the outside edge of the foot. The fifth metatarsal has a tuberosity or styloid process. The fifth metatarsal can include an intramedullary canal. A Jones fracture is a type of injury to the base of the metatarsal. A pseudo-Jones fracture is a type of injury to the tuberosity. The fifth metatarsal can experience other injuries including stress fractures. The figures can generally show a fracture F. The fracture F can include one or more bone fragments.

Figure 32:
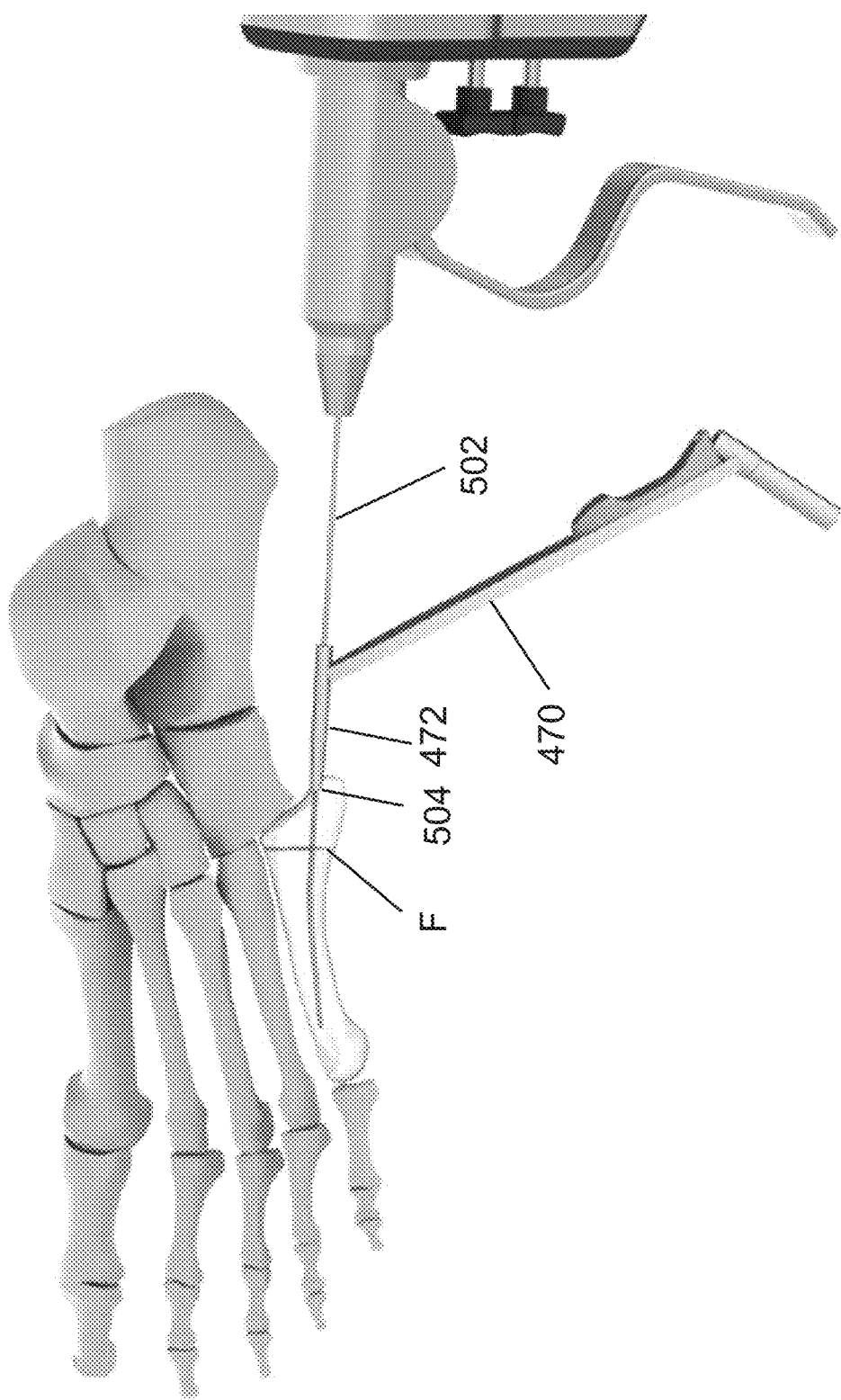
FIG. 32 illustrates a method step for establishing an entry point in a method to install a repair system.

FIG. 32 shows a method step of establishing an entry point. The user can establish an entry point using a K-wire 502. In some methods of use, a 1.6 mm K-wire is used. The K-wire can be positioned at the tip of the fifth metatarsal tuberosity. The K-wire 502 can form a canal in the fifth metatarsal. The K-wire 502 can be advanced into the intramedullary canal of the fifth metatarsal. FIG. 32 shows the first cannula 472 of the drill guide 470. The K-wire 502 can be inserted into the first cannula 472 of the drill guide 470. The first cannula 472 can include a distal surface 478 configured to abut bone. Referring back to FIG. 24, the distal surface 478 can include one or more projections to increase grip of the bone. The first cannula 472 can define the trajectory of the K-wire 502, when the distal surface 504 abuts bone. FIG. 32 shows a fracture F. The K-wire can be positioned across the fracture F. The first cannula 472 can include a distal surface 478 configured to abut bone.

Figure 33A:
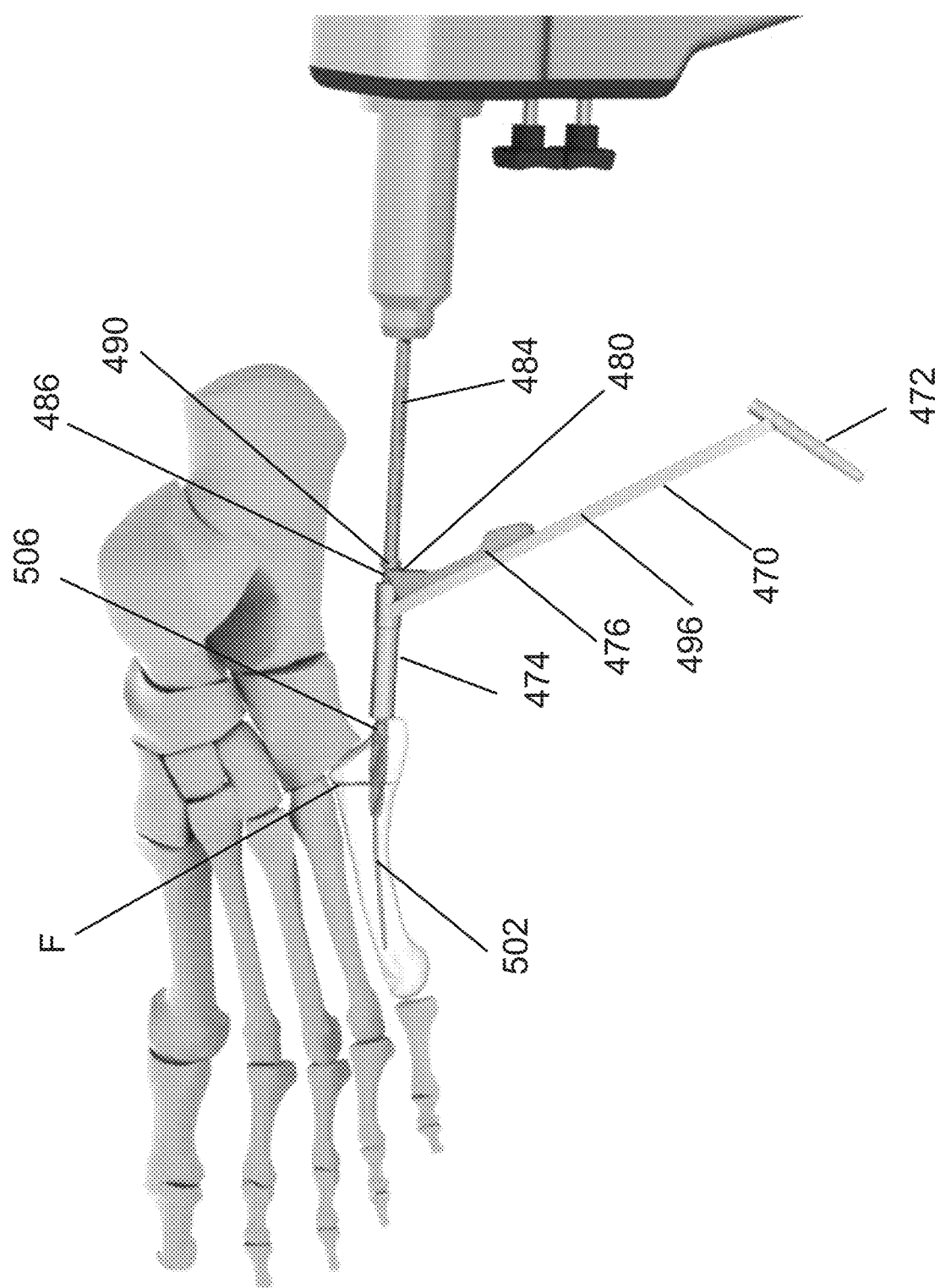
FIGS. 33A-33B illustrates method steps of using a reamer in a method to install a repair system.
Figure 33B:
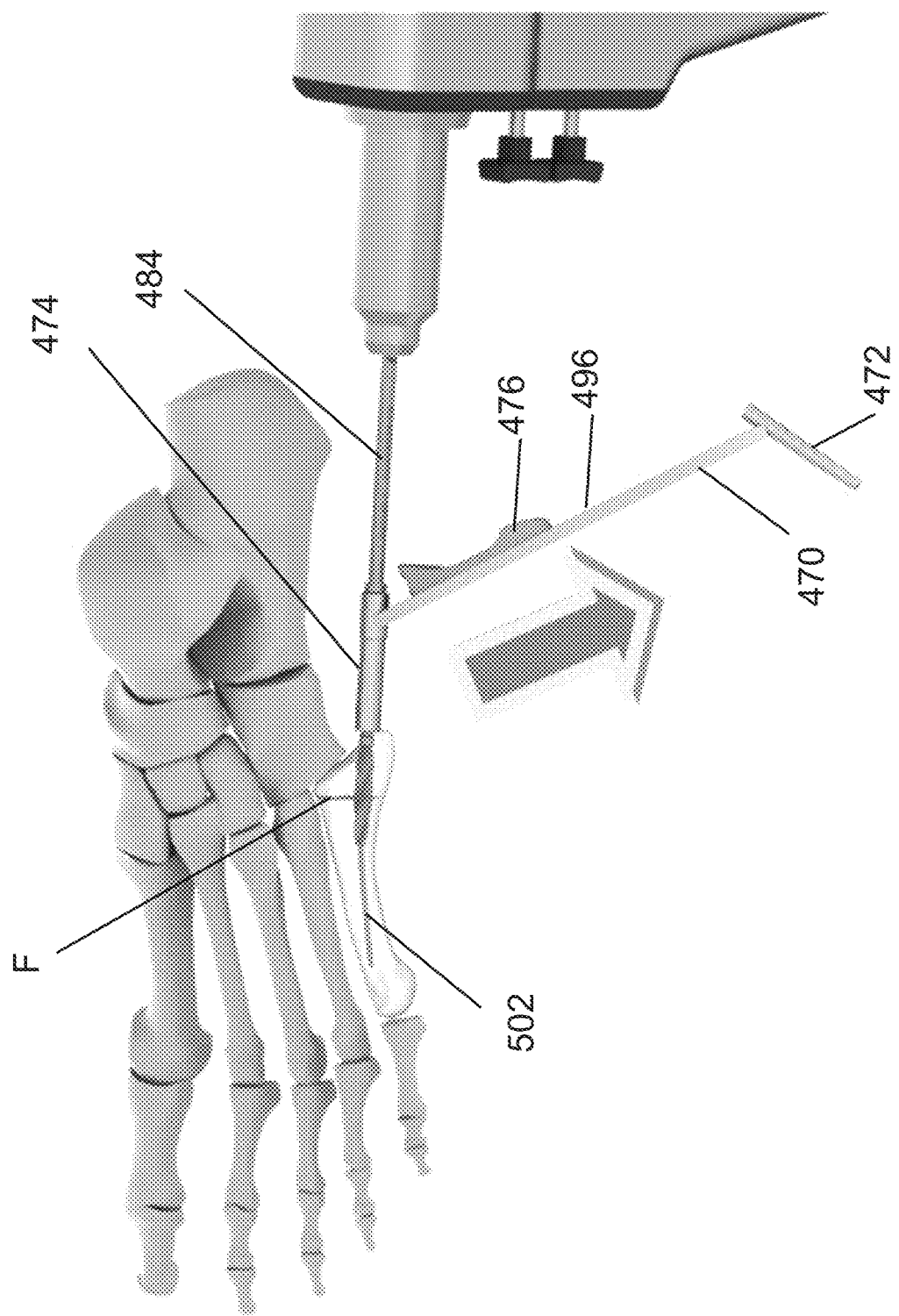

FIGS. 33A-33B show method steps related to using the reamer 484. The user can use the reamer 484 to ream the fifth metatarsal. The user can use the reamer 484 to ream the tissue surrounding the fifth metatarsal. In some methods of use, a 5.2 mm reamer is used. The reamer 484 can form a canal in the fifth metatarsal. The reamer 484 can be advanced into the intramedullary canal of the fifth metatarsal. The reamer 484 can form a counter bore which is greater in diameter than the intramedullary canal of the fifth metatarsal.

The user can rotate the drill guide 470 from the position shown in FIG. 32. The user can position the second cannula 474 over the K-wire 502. The second cannula 474 can include a distal surface 506 configured to abut bone. The second cannula 474 can define the trajectory of the reamer 484, when the distal surface 506 abuts bone. The user can position the reamer 484 over the K-wire 502. The reamer 484 can be cannulated. The user can translate the reamer 484 along the K-wire 502. The user can translate the shaft 486 of the reamer 484 through the opening 480 of the slider 476. The user can ream the proximal entry portal. The reamer 484 can be positioned across the fracture F.

FIG. 33A shows a method step wherein the slider 476 is in the standard position. The user can slide the slider 476 along the arm 496 until the slider 476 is in the standard position. In some methods of use, the spring 492 shown in FIG. 29 biases the slider 476 toward the standard position.

The stop 490 of the reamer 484 abuts the opening 480 in the slider 476. The reamer 484 penetrates a distance GS when the stop 490 of the reamer 484 abuts the slider 476. FIG. 33A shows a method step where the user reams a first depth GS corresponding to the standard position.

FIG. 33B shows a method step wherein the slider 476 is in the long position. The user can slide the slider 476 along the arm 496 until the slider 476 is in the long position. In some methods of use, the spring 492 biases the slider 476 toward the standard position as described with respect to FIG. 29. The user can overcome the biasing force of the spring 492 to position the slider 476 in the long position. The slider 476 can be moved away from the second cannula 474. The slider 476 can be moved away from the reamer 484. The stop 490 of the reamer 484 can abut the second cannula 474. FIG. 33B shows a method step where the user drills a second depth GL corresponding to the long position. As described herein, the countersink depth GL can be greater than the countersink depth GS. The reamer 484 can penetrate a distance GL when the stop 490 of the reamer 484 abuts the second cannula 474. The differences between GS and GL can be 4 mm. The user can incrementally ream until the stop 490 of the reamer 484 abuts a structure thereby limiting the depth of penetration.

Figure 34A:
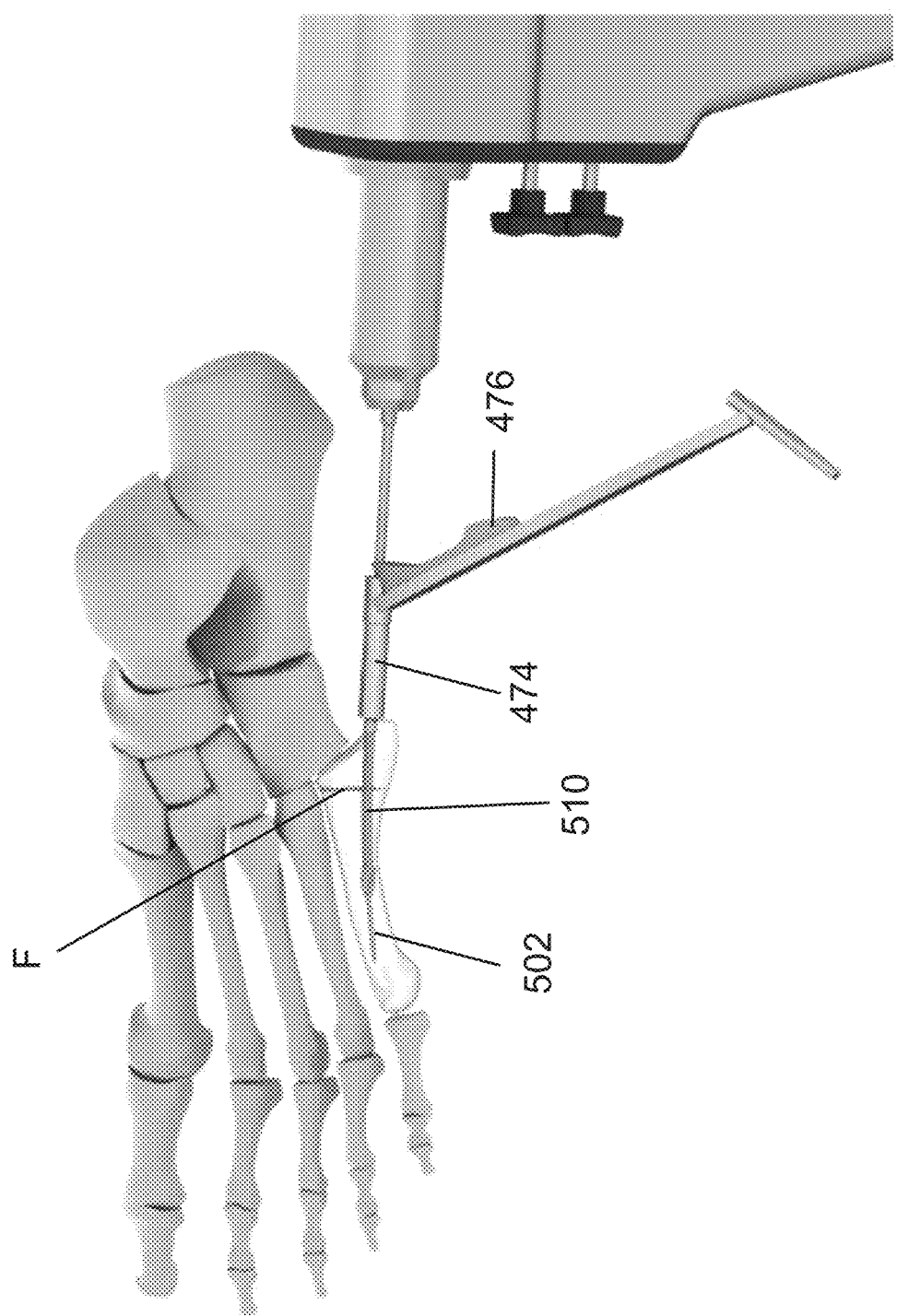
FIGS. 34A-B illustrates method steps of reaming to a distal portion in a method to install a repair system.
Figure 34B:
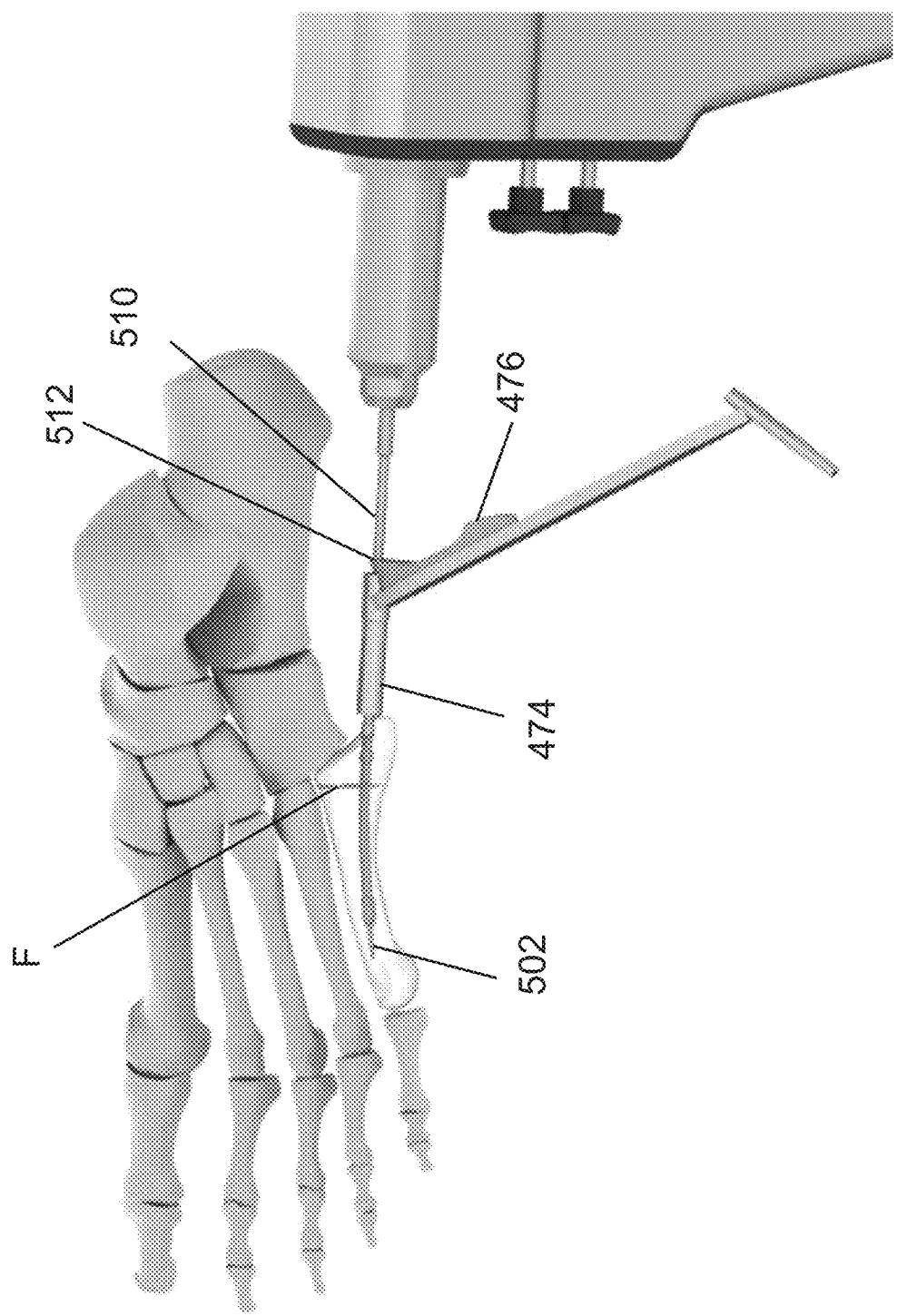

FIGS. 34A-34B show method steps related to incrementally reaming. The user can remove the reamer 484 from the second cannula 474. The user can position a second reamer 510 over the K-wire 502. The user can translate the second reamer 510 along the K-wire 502. The user can translate a shaft 514 of the second reamer 510 through the opening 480 of the slider 476. The second reamer 510 can translated within the second cannula 474 of the insertion tool 410. The second reamer 510 can be positioned in the second cannula 474 after the reamer 484 is removed from the second cannula 474.

The second reamer 510 can form a canal in the fifth metatarsal. The second reamer 510 can be advanced into the intramedullary canal of the fifth metatarsal. The second reamer 510 can form a bore which is greater in diameter than the intramedullary canal of the fifth metatarsal. The second reamer 510 can incrementally ream the intramedullary canal. As described herein, the reamer 484 can ream a proximal portion or countersink portion. The second reamer 510 can ream a distal canal. The second reamer 510 can incrementally ream a distance corresponding to the length of the fixation device 100 from the proximal end 102 to the distal end 104. The diameter of the fixation device 100 can be slightly smaller than the final reamer diameter. The final reamer diameter can be 0.2 mm greater than the diameter of the fixation device 100. The final reamer diameter can be 0.2 mm greater than the diameter of the distal portion 110 of the fixation device 100. The final reamer diameter can be 0.2 mm greater than the diameter of the hub 120 of the fixation device 100. The user can ream to the proper depth. The second reamer 510 can be positioned across the fracture F.

In some embodiments, the second reamer 510 can include a stop 512. In some embodiments, the stop 512 of the second reamer 510 can be designed to abut the slider 476 in the standard position. In some embodiments, the stop 512 of the second reamer 510 can be designed to abut the second cannula 474 in the long position. The user can select between the standard position and the long position by moving the slider 476 along the arm 496. The user can incrementally ream until the stop 512 of the second reamer 510 abuts a structure thereby limiting the depth of penetration. FIGS. 34A-34B show method steps wherein the slider 476 is in the standard position. In some methods, the user moves the slider 476 away from the second cannula 474. The user incrementally reams until the stop 512 of the reamer abuts the second cannula in the long position.

Figure 35A:
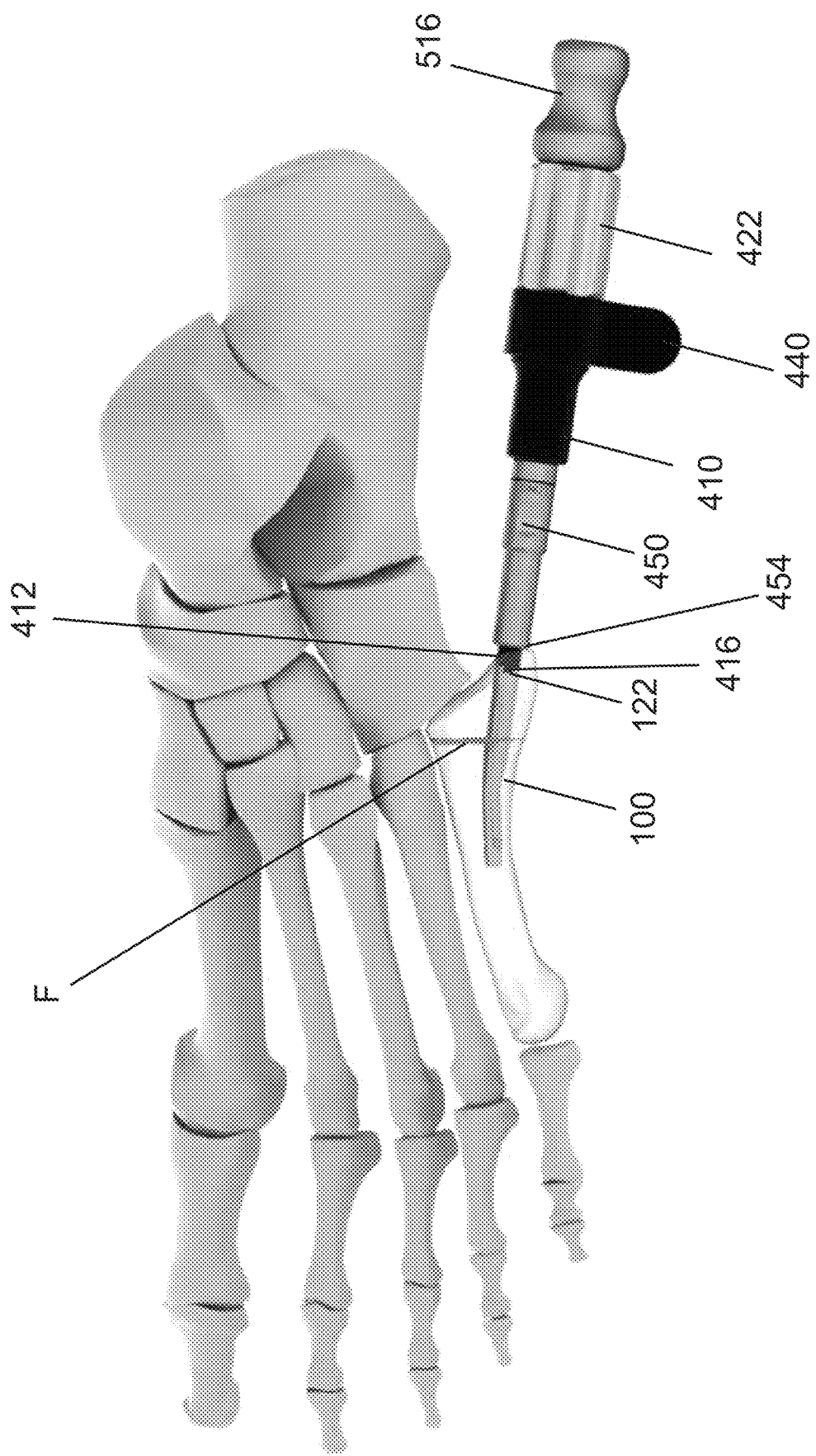
FIGS. 35A-B illustrates method steps of inserting the fixation device in a method to install a repair system.
Figure 35B:
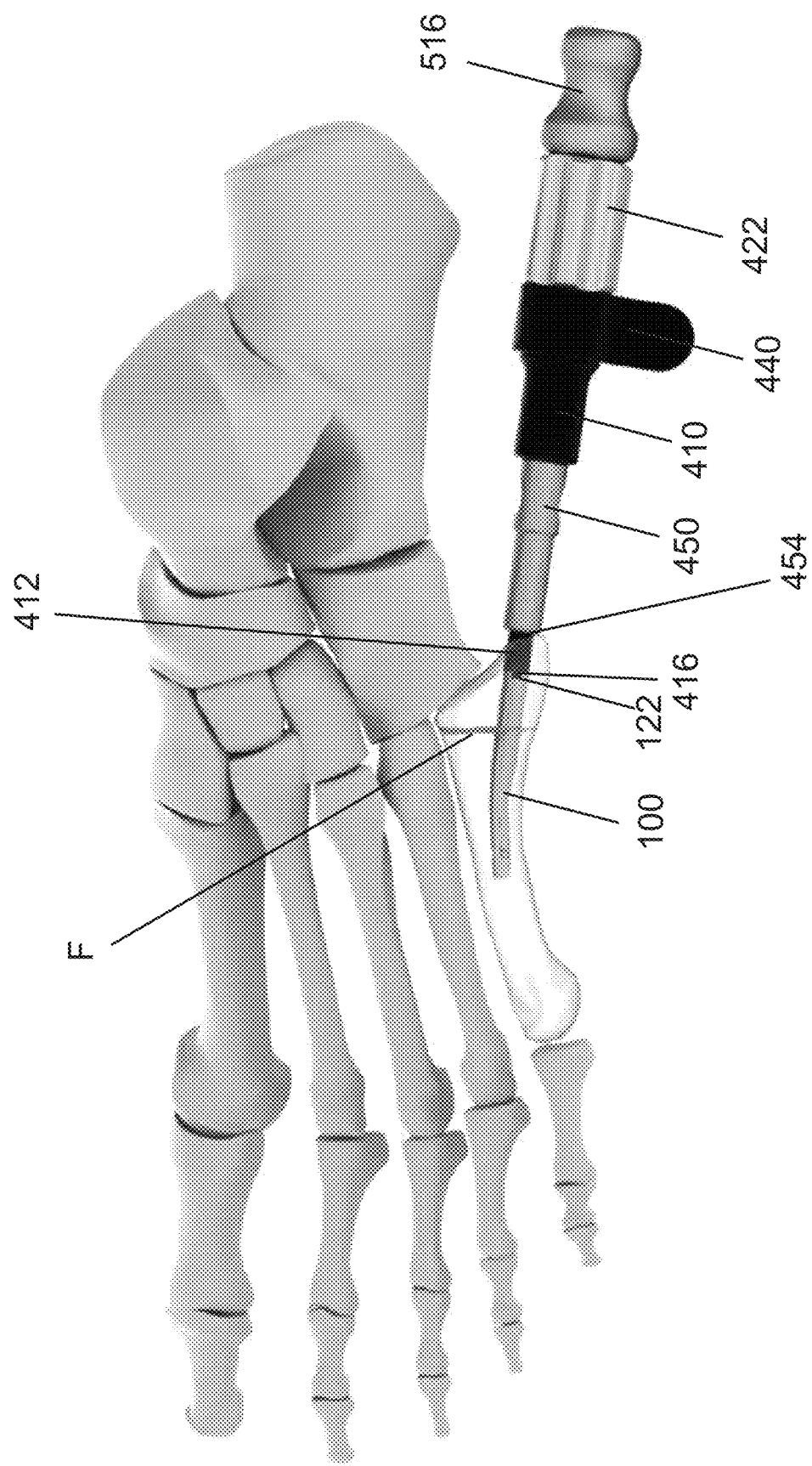

FIGS. 35A-35B show method steps related to inserting the fixation device 100. The user can remove the drill guide 470. The user can assemble the insertion tool 410. The user can couple the fixation device 100 to the insertion tool 410. The user can align the corresponding engagement member 416 of the elongate member 412 with the engagement member 122 of the fixation device 100. The engagement member 122 and the corresponding engagement member 416 can limit rotation between the insertion tool 410 and the fixation device 100. Referring back to FIGS. 17 and 19, the user can insert the shaft 420 into the lumen 414 of the elongate member 412. The thread 424 of the shaft 420 can extend distally from the elongate member 412. The thread 424 can engage the second threaded section 146 of the fixation device 100 to couple the insertion tool 410 to the fixation device 100.

The user can adjust the insertion tool 410 between the standard position and the long position. The user can grasp the slider 450. Referring back to FIG. 20, the user can pull the slider 450 distally such that the flange 456 translates distally. The user can pull the slider 450 distally such that the flange 456 translates distally to disengage the groove 462. The user can rotate the slider 450. The user can rotate the slider 450 to align the flange 456 with the slot 464. The user can push the slider 450 proximally. In some embodiments, the user releases the slider 450 and the spring 446 biases the flange 456 into the slot 464. The user can pull the slider 450 distally such that the flange 456 translates distally to disengage the slot 464. The user can rotate the slider 450 to align the flange 456 with the groove 462. In some embodiments, the user releases the slider 450 and the spring 446 biases the flange 456 into the groove 462.

The distal end 454 of the slider 450 can be designed to engage the edge of the fifth metatarsal. The distal end 454 of the slide 450 can be designed to limit insertion of the fixation device 100. FIG. 34A shows the position of the fixation device 100 when the flange 456 engages the groove 462. FIG. 34A shows the position of the fixation device 100 when the slider 450 is in the standard position. FIG. 34B shows the position of the fixation device 100 when the flange 456 engages the slot 464. FIG. 34B shows the position of the fixation device 100 when the slider 450 is in the long position. The fixation device 100 can be positioned across the fracture F.

Referring back to FIGS. 33A-33B, the user can select between the standard position and the long position for the proximal reaming by moving the slider 476. In some methods of use, the proximal reaming was performed to the standard position. The user can set the insertion tool 410 to the corresponding standard position. The user can select the position by pulling and rotating a portion of the insertion tool 410 to the standard position. The fixation device 100 can be inserted until the insertion tool 410 abuts bone FIG. 35A shows the final position of the fixation device 100 in the standard position.

In some methods of use, the proximal reaming was performed to the long position. The user can set the insertion tool 410 to the corresponding long position. The user can select the position by pulling and rotating a portion of the insertion tool 410 to the long position. The fixation device 100 can be inserted until the insertion tool 410 abuts bone. FIG. 35B shows the final position of the fixation device 100 in the long position.

FIGS. 35A-35B show an embodiment of an impact cap 516. The impact cap 516 can include a cap and a shaft (not shown). The user can strike the impact cap 516 to seat the fixation device 100. In some embodiments, one or more light blows to the impact cap 516 can seat the fixation device 100. In some methods, the shaft of the impact cap 516 can be inserted through the handle 422 and the handle 440. In some methods, the shaft of the impact cap 516 can be inserted through the lumen 426 of the shaft 420, as shown in FIG. 17.

Figure 36:
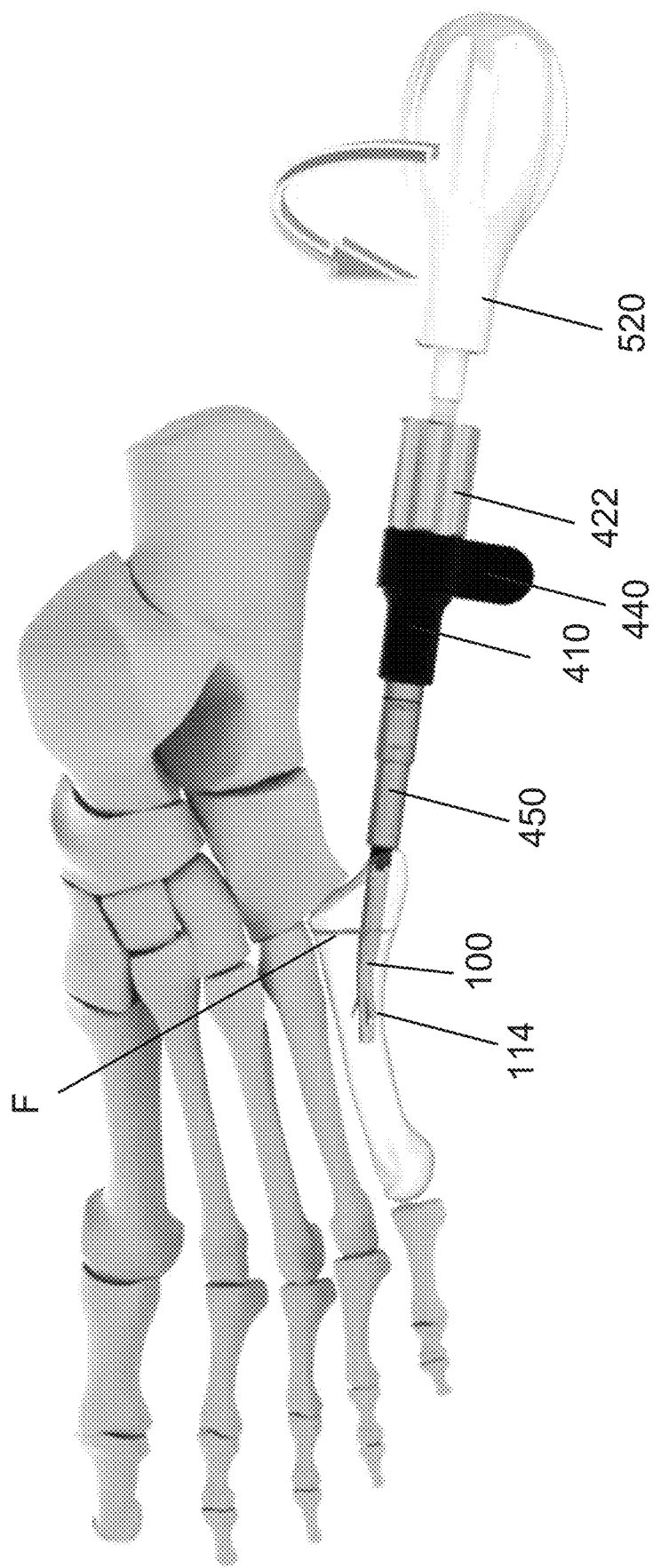
FIG. 36 illustrates a method step of deploying one or more grippers in a method to install a repair system.

FIG. 36 shows method steps related to deploying one or more grippers 114 of the fixation device 100. The method can include using an actuation driver 520. The actuation driver 520 can be inserted into the fixation device 100 once the fixation device 100 has reached its final position (e.g., the long position or the standard position). The final position of the fixation device 100 in FIG. 36 is the standard position. The actuation driver 510 can deploy the grippers 114 when the fixation device 100 is in the long position.

Referring back to FIG. 5, the actuation driver 520 can engage the socket 136 of the actuator 126. The actuation driver 520 can rotate the elongate member 130 of the actuator 126. As the actuation driver 520 is rotated, the actuator 126 can rotate within the fixation device 100. As the actuation driver 520 is rotated, the actuator head 134 can translate toward the proximal end 102 of the fixation device 100. The actuator head 134 can deploy the one or more grippers 114 by translating toward the proximal end 102 of the fixation device 100.

In some methods, the actuation driver 520 produces an indicator to the user that the one or more grippers 114 have been deployed. In some methods, the actuation driver 520 produces an audial indicator, such as a click. In some methods, the indicator is tactile, such as the actuation driver 520 abuts a stop which prevents further rotation. In some methods, the indicator is visual. The user can rotate the actuation driver 420 based on one or more markings. As one example, the markings can indicate the position of the actuation driver 520 relative to the handle 422 when the one or more grippers 114 are deployed.

In some methods, the shaft of the actuation driver 520 can be inserted through the handle 422 and the handle 440. In some methods, the shaft of the actuation driver 520 can be inserted through the lumen 426 of the shaft 420, as shown in FIG. 17. In some methods, the actuation driver 520 is removed once the grippers 114 are deployed. In some embodiments, the one or more grippers 114 can be deployed distal to the fracture F.

Figure 37:
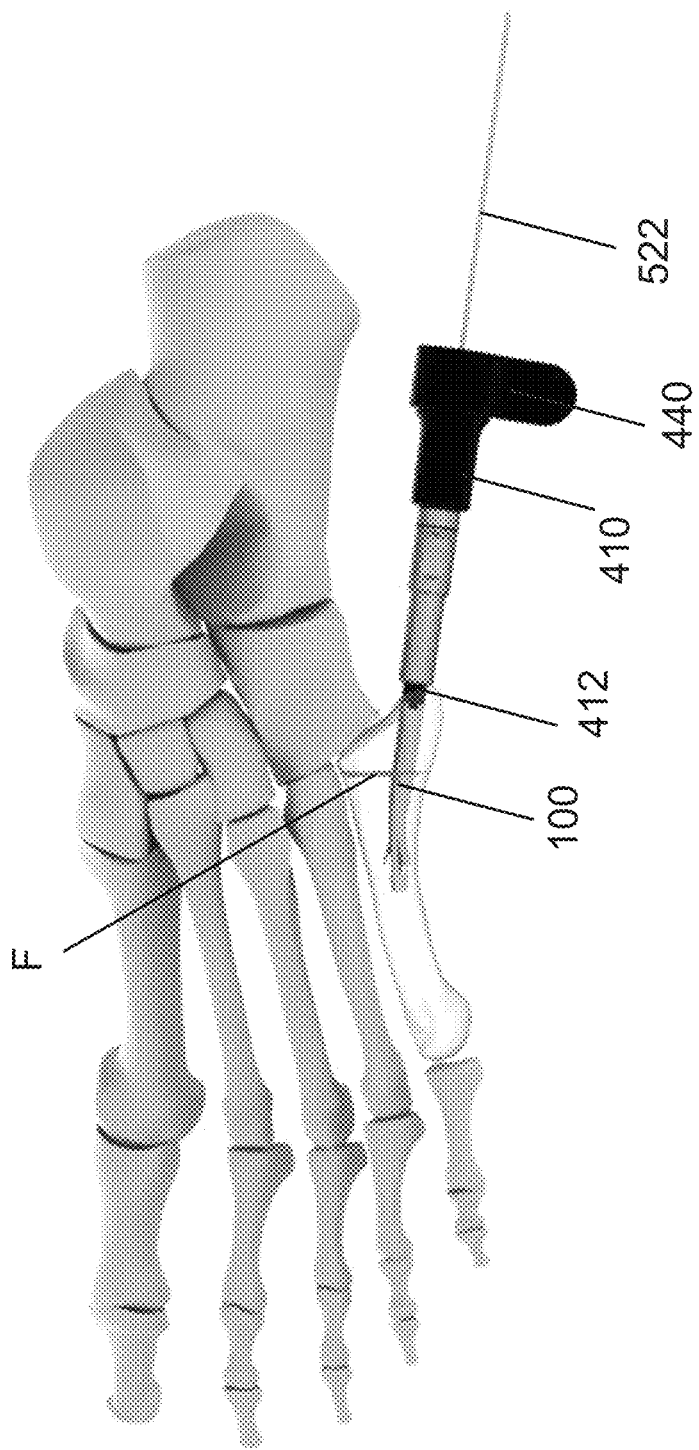
FIG. 37 illustrates a method step of inserting a guide wire in a method to install a repair system.

FIG. 37 shows a method step related to inserting a K-wire 522. In some methods, the K-wire 522 is a 1.25 mm K-wire. In some methods, the shaft 420 can be removed. In some methods, the K-wire 522 can be inserted through the handle 440 of the insertion tool 410. In some methods, the K-wire 522 can be inserted through the lumen 414 of the elongate member 412, as shown in FIG. 19. The K-wire 522 can be inserted into the fixation device 100.

Figure 38A:
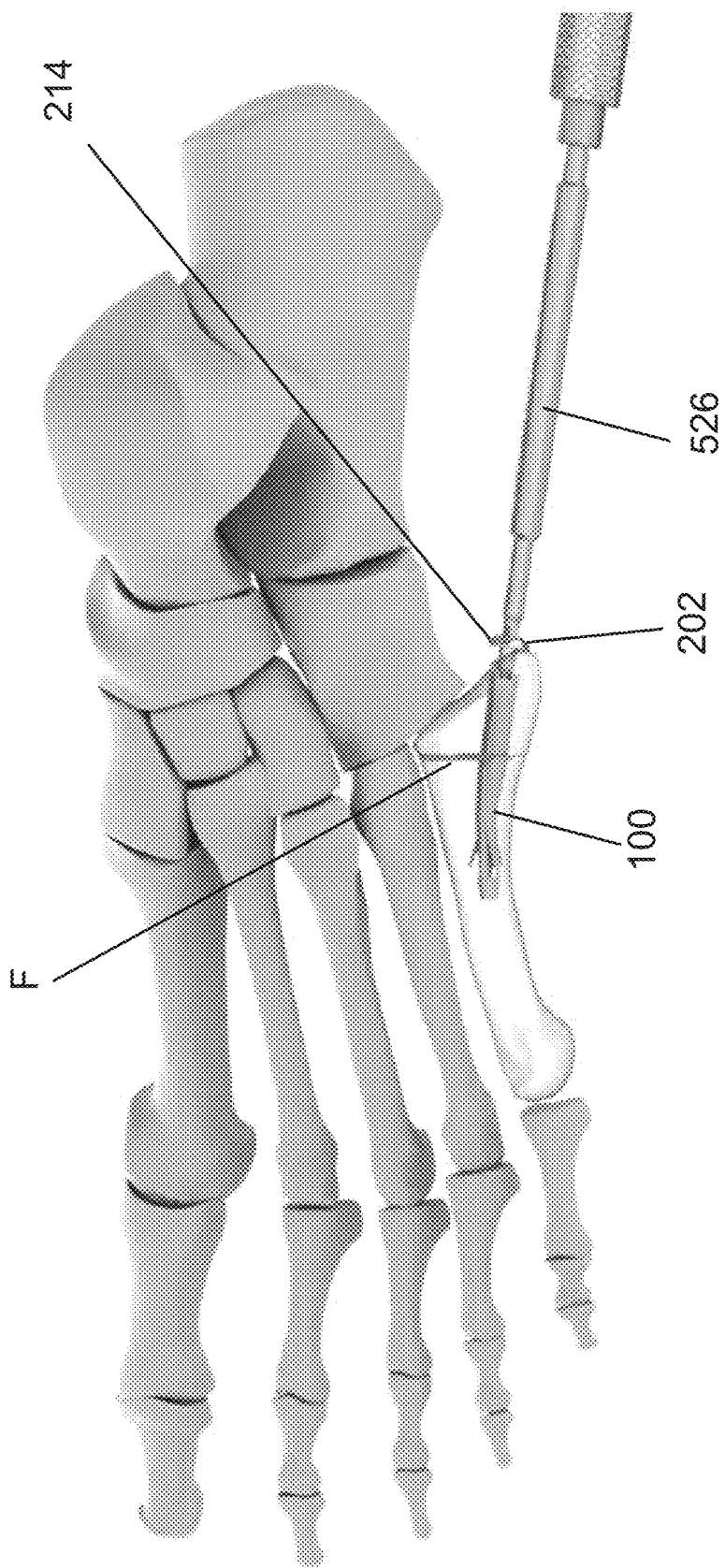
FIG. 38A-38B illustrates method steps of inserting an end cap in a method to install a repair system.
Figure 38B:
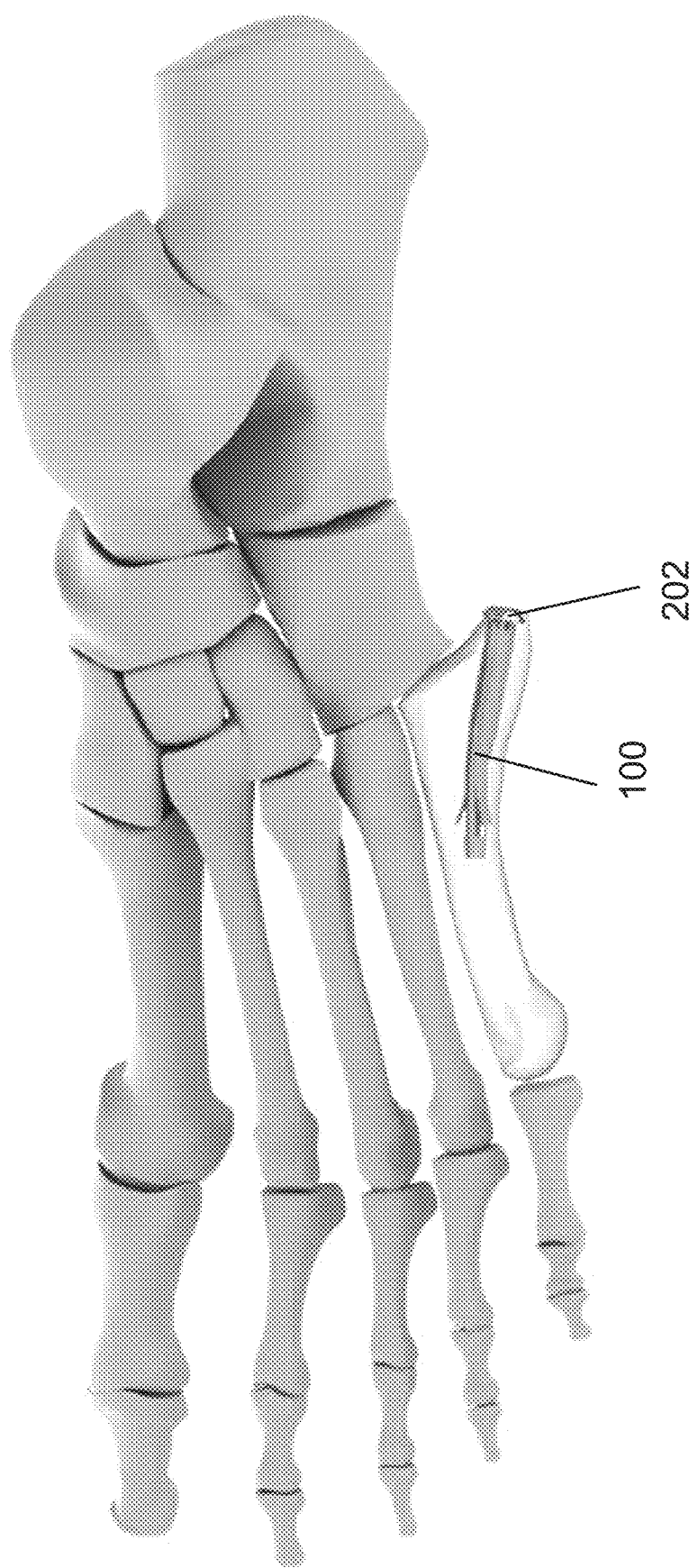

FIGS. 38A-38B show a method steps related to inserting an end cap 202. FIGS. 38A-38B shows the fixation device 100 in the standard position. In some methods of use, the fixation 100 is in the long position. The end caps 242, 262, 282, 302 can be inserted in a similar manner. In some methods, the elongate member 412 is removed. In some methods the K-wire 522 protrudes proximally from the fixation device 100. As described herein, the end cap 202 can be cannulated. The fastener 204 can be cannulated. As described herein, the fastener 404 can be cannulated and can be inserted in a similar manner as fastener 204. The end cap 202 can be coupled to a driver 526. The driver 526 can be cannulated. The driver 526 can be translated along the K-wire 522. The driver 526 and the end cap 202 can be translated along the K-wire 522 toward the fixation device 100.

The fastener 204 can engage the fixation device 100. Referring back to FIG. 6, the thread 206 of the fastener 204 can engage the first threaded section 144 of the fixation device 100 when the driver 526 is rotated. The driver 526 can engage the socket 212 of the fastener head 210 to transmit torque.

The end cap 202 can include the cap 214. In some methods, the cap 214 can be translated relative to the fastener head 210. In some methods, the cap 214 can be rotated relative to the fastener head 210. In some methods, the cap 214 can have polyaxial movement relative to the fastener head 210. The cap 214 can include the exterior surface 224 designed to abut the anatomy of the patient. The cap 214 can include the curved edges 226 designed to abut the surrounding tissue.

The end cap 202 can reduce the fracture as shown in FIG. 38B. As the driver 526 is rotated, the end cap 202 can apply a force on the bone fragment of the fifth metatarsal. The compressive force can bring two or more bone fragments of the fifth metatarsal together. FIG. 38B shows the installed the fixation device 100 and the end cap 202. In some embodiments, the end cap 202 can be deployed proximal to the fracture F.

Figure 39A:
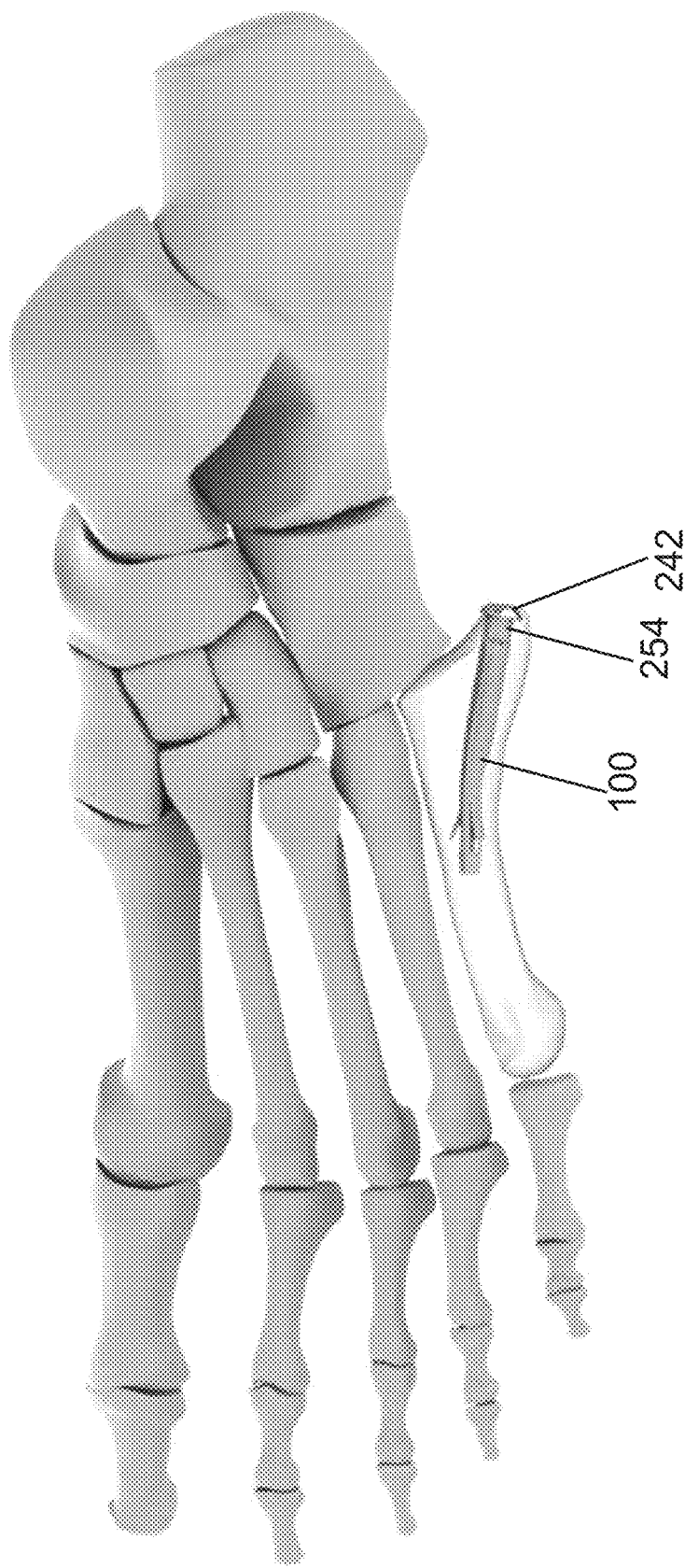
FIG. 39A-39B illustrates method steps of inserting different end caps in a method to install a repair system.
Figure 39B:
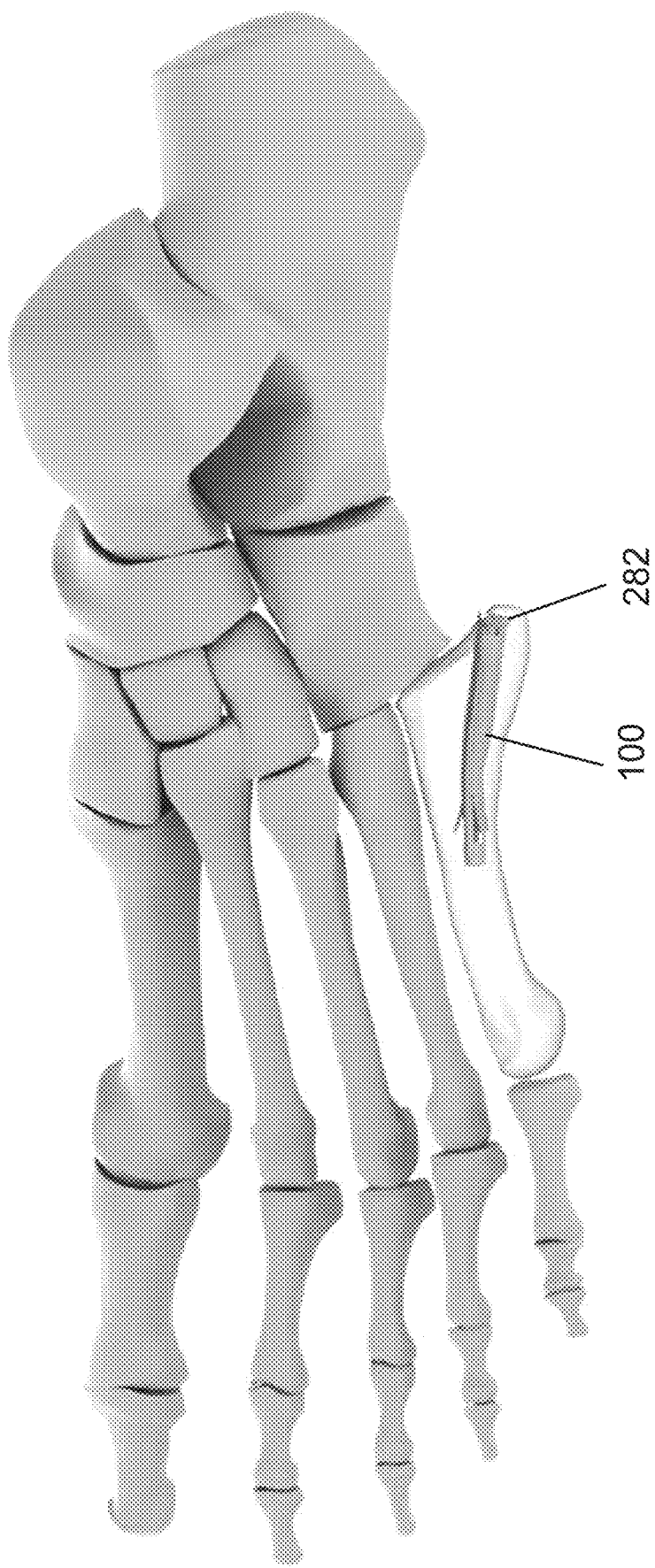

FIGS. 39A-39B show various repair systems 200 inserted into the fifth metatarsal. FIG. 39A shows the fixation device 100 and the end cap 242. In some methods, the user selects end cap 242 or another end cap with the length extending section. Any of the end caps described herein can include a length extending section. Referring back to FIGS. 9 and 10, the end cap 242 includes the second section 254. The second section 254 can include a cylindrical boss. The cylindrical boss can be sized to fit within the countersink created by the reamer 484 in the long position. The second section 254 can be sized to fit with the fifth metatarsal. The second section 254 can increase the length of the cap 244.

In some methods of use, the user selects the long fastener 404. The long fastener 404 can include the length extending section 406. In some embodiments, the length of the second section 254 of the cap 244 can correspond to the length of the length extending section 406 of the long fastener 404. The length extending section 406 of the long fastener 404 can be disposed within the second section 254 of the cap 244 when the fastener 404 is disposed within the cap 444.

In some methods of use, the user can select the long position. The long position can include increasing the depth of the countersink of the reamer 484. The long position can include moving the slider 476 of the of the drill guide 470 to the long position. The long position can include abutting the stop 490 of the reamer 484 with the second cannula 474. The long position can include adjusting the insertion tool 410. The long position can include pulling the slider 450. The long position can include rotating the slider 450. The long position can expose a longer length of the elongate member 412 of the insertion tool 410. In some methods of use, the user can select the standard position. The standard position can relate to a shorter countersink produced by the reamer 484.

FIG. 39B shows the fixation device 100 and the end cap 282. In some methods, the cap 284 self-countersinks into the bone. The driver 524 can rotate the fastener 202. As the fastener 202 is rotated, the cap 284 can drive itself into the bone of the fifth metatarsal. The cap 284 can include one or more grooves 292. The grooves 292 can be self-tapping thereby driving the cap 284 into the bone.

FIGS. 40-44 generally show method steps related to removing repair systems described herein. A surgical method can include one or more of the following steps. One or more of the following steps can be performed in any order.

Figure 40:
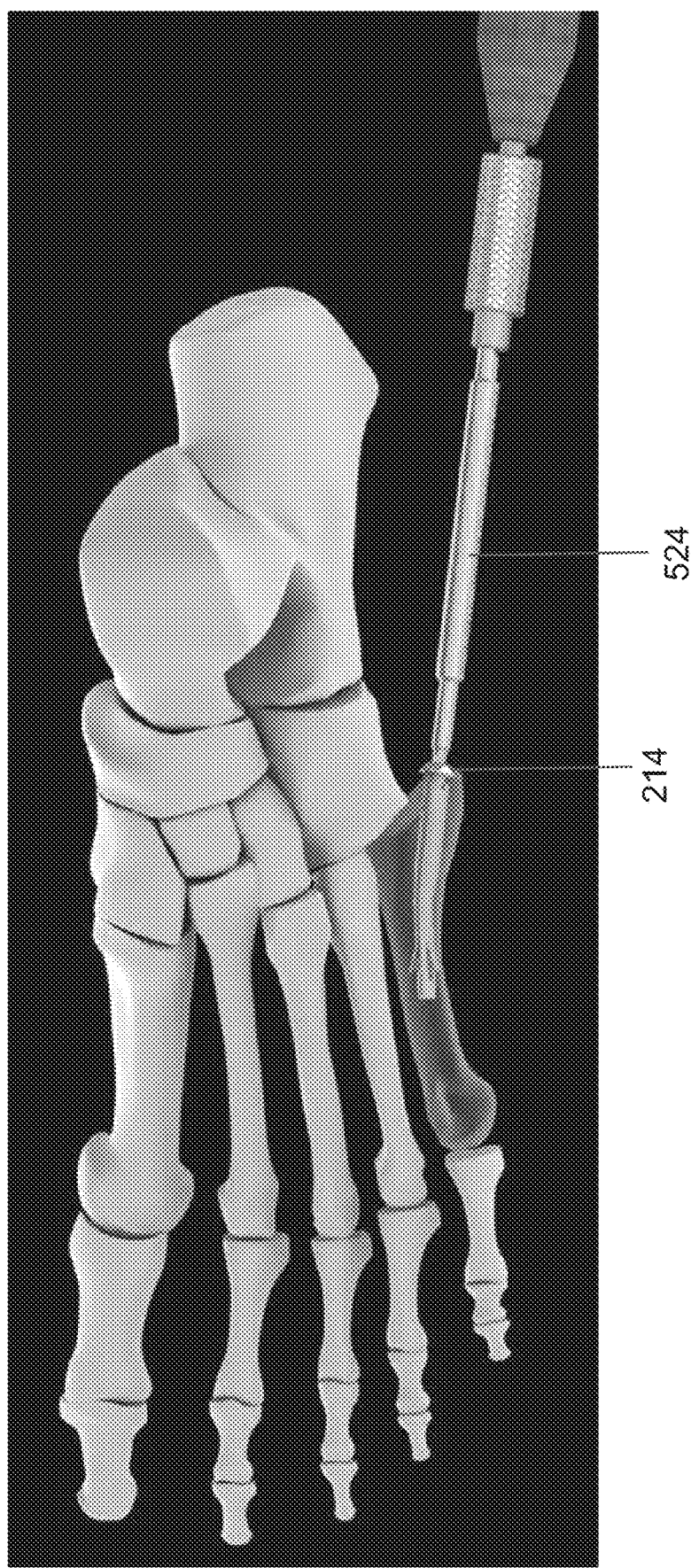
FIG. 40 is a view of a method step of removing an end cap in a method to remove a repair system.

FIG. 40 shows a method step related to the removal of the end cap 202. The driver 524 can be coupled to the fastener 204 or the long fastener 404 disposed within the cap 214. The driver 524 can be inserted into the socket 212 of the fastener 404 or the long fastener 404 as shown in FIGS. 6 and 9. The driver 524 can be rotated. As the driver 524 is rotated, the thread 206 of the fastener 202 or the long fastener 402 disengages with the first threaded section 144 of the fixation device 100, see FIG. 6. The end caps described herein can be removed in a similar manner.

Figure 41:
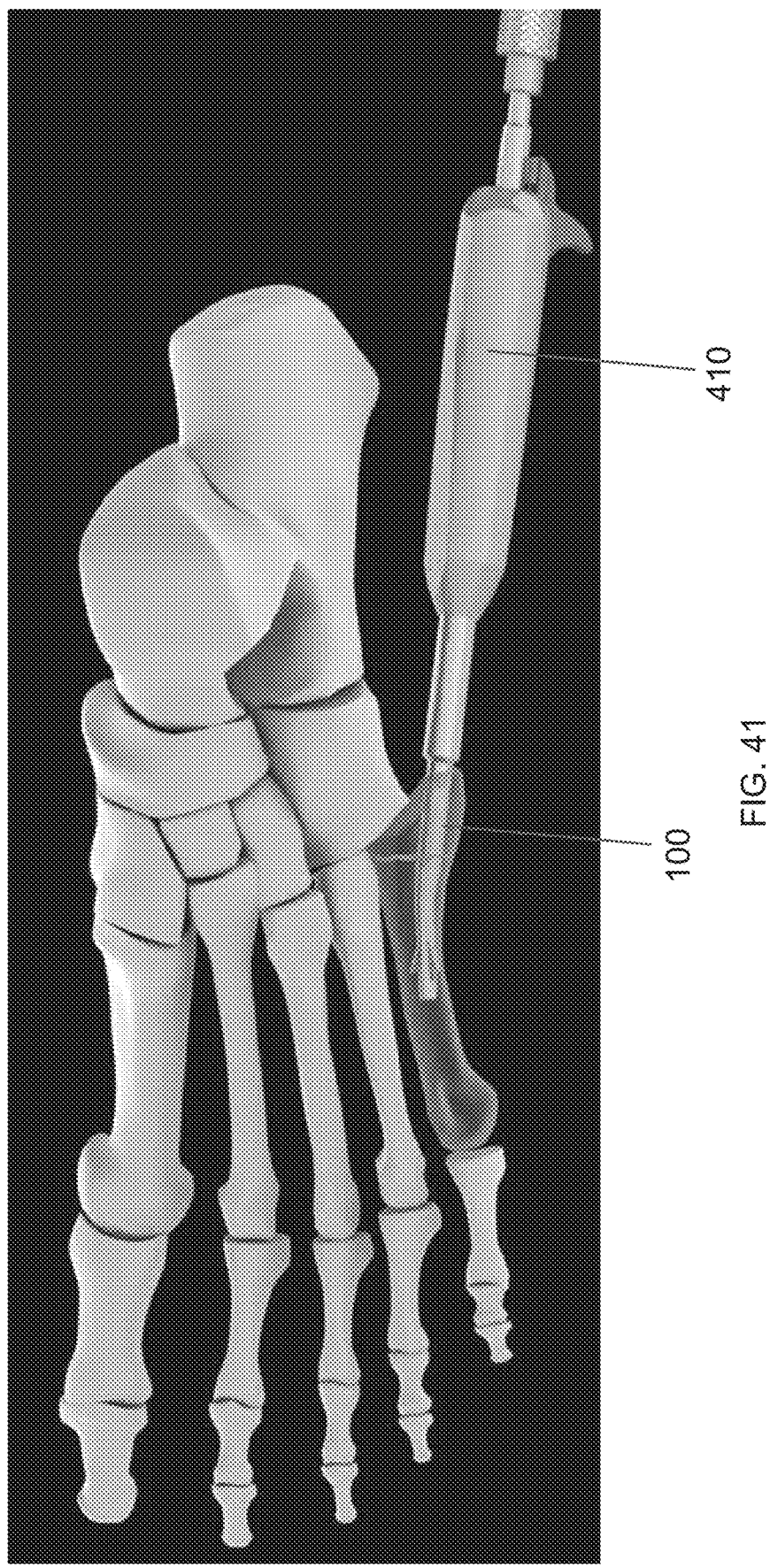
FIG. 41 illustrates a method step of attaching an insertion tool in a method to remove a repair system.

FIG. 41 shows a method step related to coupling the insertion tool 410. Referring back to FIGS. 6 and 17, the corresponding engagement member 416 of the insertion tool 410 can engage the engagement member 122 of the fixation device 100. The shaft 420 can be inserted into the lumen 414 of the elongate member 412. The thread 424 of the shaft 420 can engage the second threaded section 146 of the insertion tool 410.

Figure 42:
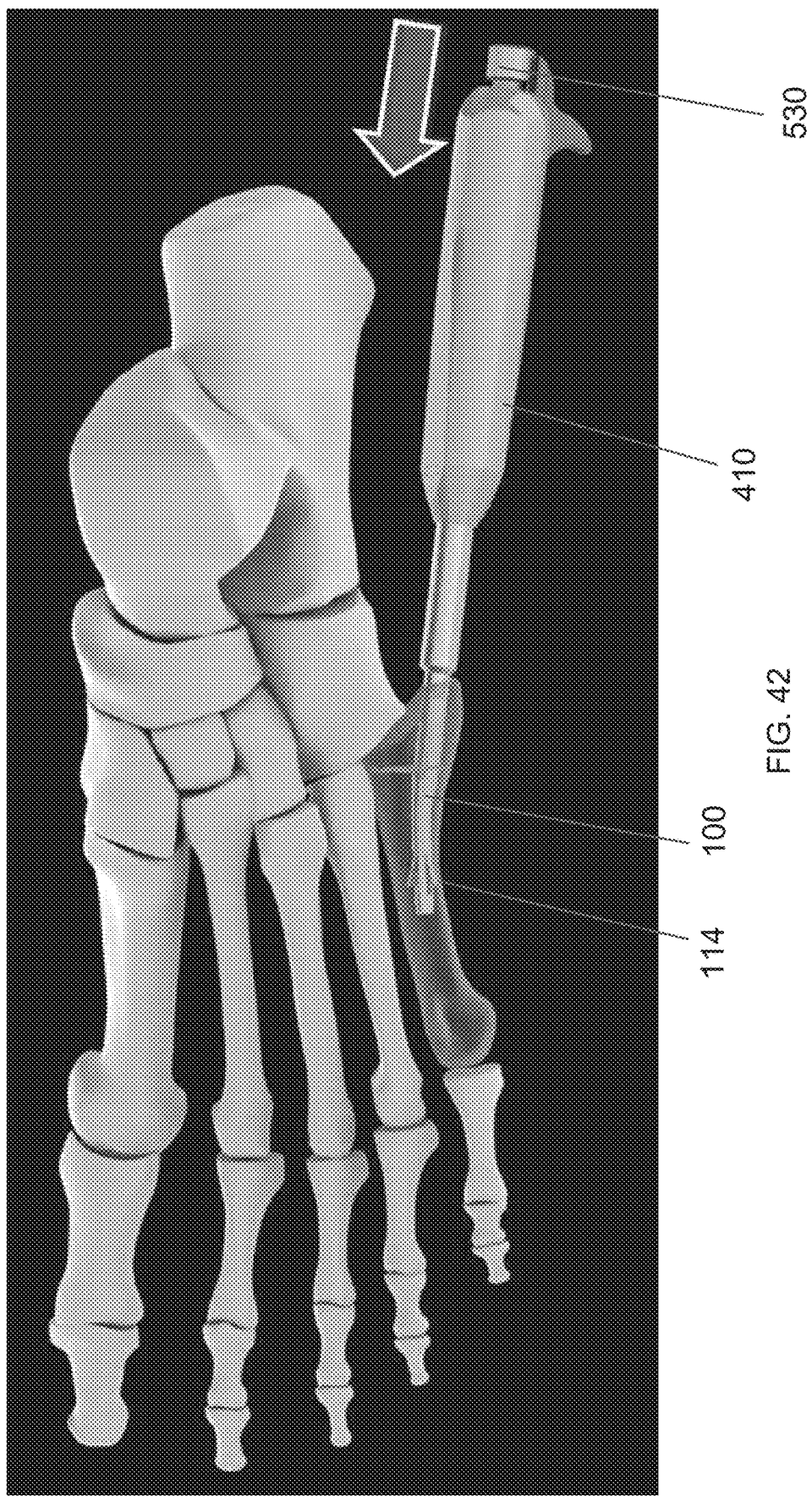
FIG. 42 illustrates a method step of inserting a shaft of an actuation driver in a method to remove a fixation device.
Figure 43:
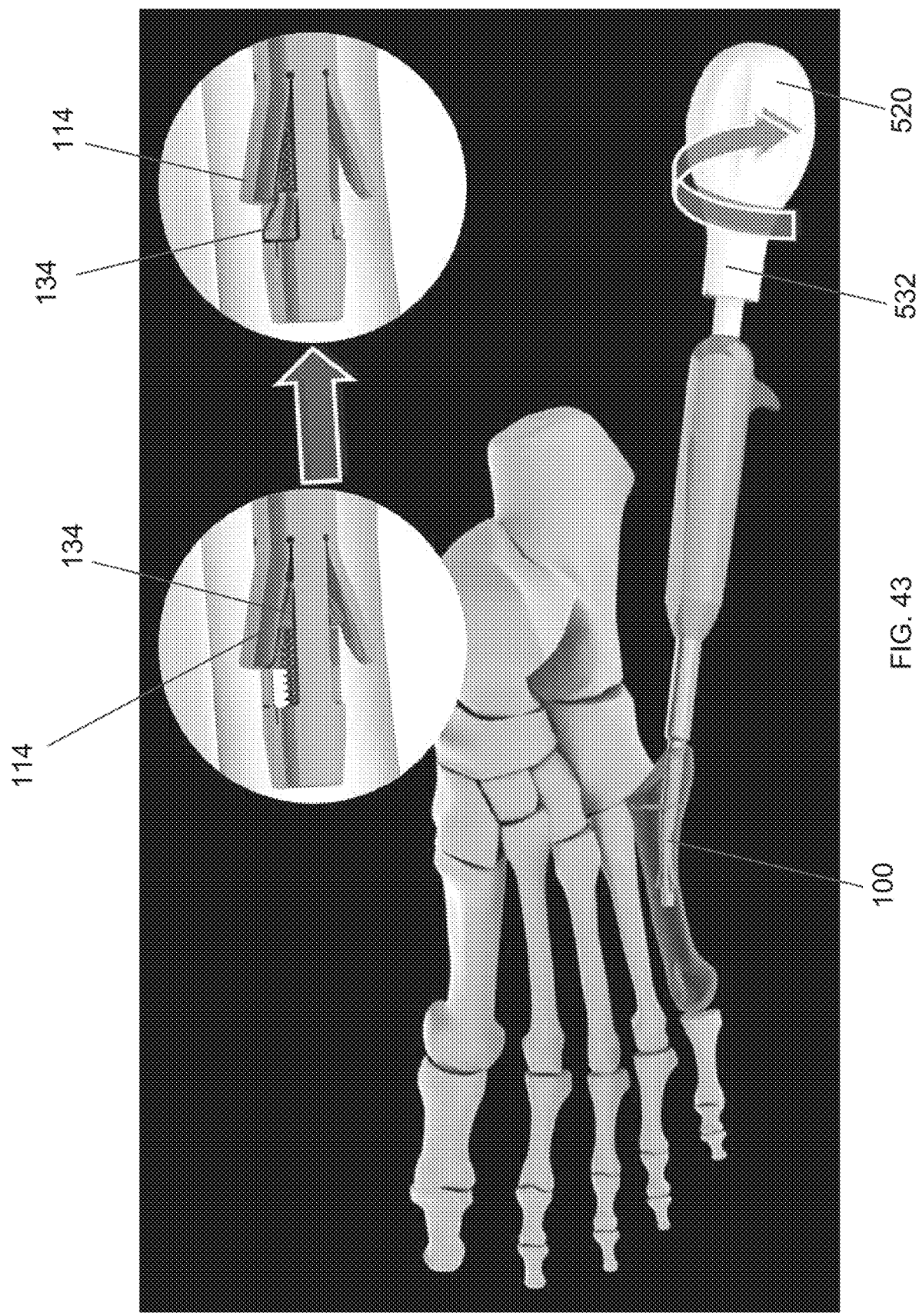
FIG. 43 illustrates a method step of collapsing one or more grippers in a method to remove a repair system.

FIGS. 42 and 43 show method steps related to collapsing the one or more grippers 114 of the fixation device 100. The shaft 530 of the actuation driver 520 can be inserted into the insertion tool 410. The handle 532 of the actuation driver 520 can be coupled to the shaft 530 of the actuation driver 520. Referring back to FIG. 5, the actuation driver 520 can engage the actuator 126 within the fixation device 100. The actuation driver 520 can be rotated to collapse the one or more grippers 114. The actuation driver 520 can be rotated clockwise to deploy the one or more grippers 114 and counterclockwise to collapse the grippers 114. In some methods, the actuator head 134 is translated toward the distal end 104 of the fixation device 100. The actuator head 134 can be translated such that the actuator head 134 no longer deflects the one or more grippers 114 outward. The one or more grippers 114 can collapse as the fixation device 100 is pulled from the fifth metatarsal. In some methods, fluoroscopy is used to verify that the one or more grippers 114 have been collapsed. One or more of the method steps described herein can be verified by fluoroscopy or other imaging techniques.

Figure 44:
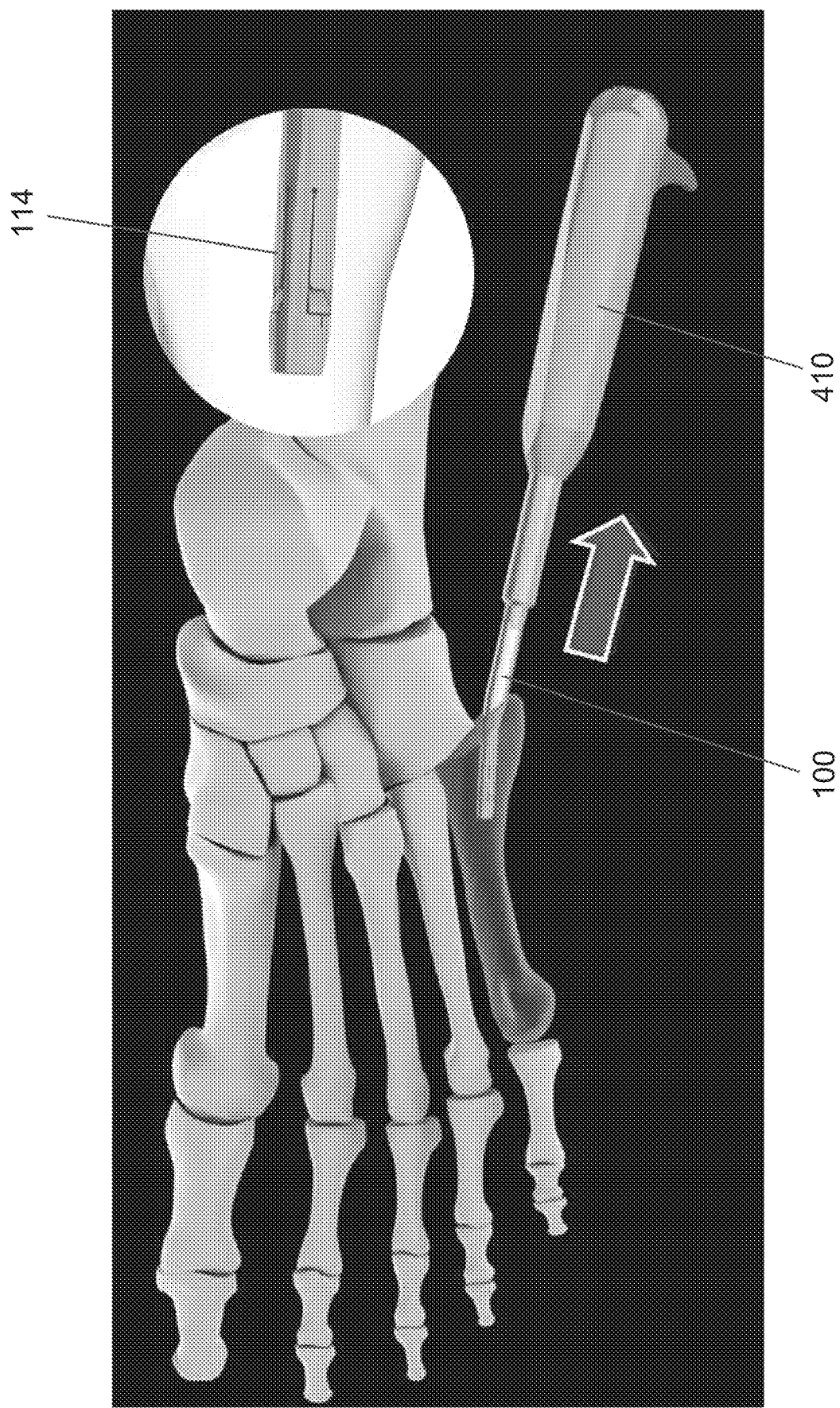
FIG. 44 illustrates a method step of pulling a fixation device in a method to remove a repair system.

FIG. 44 shows a method step related to removing the fixation device 100 from the fifth metatarsal. The grippers 114 can be collapsed as described herein. The insertion tool 410 can be pulled to remove the fixation device 100. The fixation device 100 can be removed after the fracture is healed. The fixation device 100 can be removed in a revision surgery. The fixation device 100 can be removed after the bone segments have fused.

It is contemplated that the fixation device, end caps, repair systems, tools, and methods may be used in many locations within the body. Where the proximal end of a device in the anatomical context is the end closest to the body midline and the distal end in the anatomical context is the end further from the body midline, for example, on the humerus, at the head of the humerus (located proximal, or nearest the midline of the body) or at the lateral or medial epicondyle (located distal, or furthest away from the midline); on the radius, at the head of the radius (proximal) or the radial styloid process (distal); on the ulna, at the head of the ulna (proximal) or the ulnar styloid process (distal); for the femur, at the greater trochanter (proximal) or the lateral epicondyle or medial epicondyle (distal); for the tibia, at the medial condyle (proximal) or the medial malleolus (distal); for the fibula, at the neck of the fibula (proximal) or the lateral malleoulus (distal); the ribs; the clavicle; the phalanges, the bones of the metacarpus; the bones of the carpus; the bones of themetatarsus; the bones of the tarsus; the sternum and other bones, the device may be adapted and configured with adequate internal dimension to accommodate mechanical fixation of the target bone and to fit within the anatomical constraints. As will be appreciated by those skilled in the art, access locations other than the ones described herein may also be suitable depending upon the location and nature of the fracture and the repair to be achieved. Additionally, the devices taught herein are not limited to use on the long bones listed above, but can also be used in other areas of the body as well, without departing from the scope of the invention. It is within the scope of the invention to adapt the device for use in flat bones as well as long bones.

While various embodiments of the present invention have been shown and described herein, it will be noted by those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention. It will be understood that the foregoing is only illustrative of the principles of the invention, and that various modifications, alterations, and combinations can be made by those skilled in the art without departing from the scope and spirit of the invention. Accordingly, it is not intended that the invention be limited, except as by the appended claims.

The invention claimed is:

1. A repair system, comprising:
   a fixation device comprising:
      an elongate body configured to be inserted within a fifth metatarsal, the elongate body comprising a threaded section;
      one or more grippers configured to be deflected outward to grip the sidewalls of a canal of the fifth metatarsal;
   an end cap comprising:
      a fastener comprising thread configured to engage the threaded section of the fixation device; and
      a cap, wherein the cap is configured to move relative to the fastener, and wherein a distal-most end of the cap is configured to directly abut an exterior surface of bone near the tuberosity of a fifth metatarsal,
      wherein a fastener head is captive within the cap, wherein a proximal end of the cap includes a lip forming an opening smaller than a maximum diameter of the head of the fastener, wherein the lip is proximal of a proximal-most end of the head of the fastener, and wherein an interior of the cap is tapered such that a distal end of the cap forms an opening smaller than the maximum diameter of the head of the fastener.

2. The repair system of claim 1, wherein the elongate body comprises a bend between 1 and 20 degrees, and wherein the bend is such that a proximal end of the fixation device deviates from a longitudinal axis of the fixation device while the remainder of the fixation device is arranged about the longitudinal axis.

3. The repair system of claim 1, wherein the end cap is configured for intraoperative compression.

4. The repair system of claim 1, wherein the cap is configured for polyaxial movement relative to the fastener.

5. The repair system of claim 1, wherein the cap is configured to rotate relative to the fastener.

6. The repair system of claim 1, wherein the cap comprises a tapered external surface.

7. The repair system of claim 1, wherein the cap comprises a cylindrical boss.

8. The repair system of claim 1, wherein the thread of the fastener is configured to extend distally from the cap when the fastener is disposed within the cap, and further comprising a projection extending distally from the cap.

9. The repair system of claim 1, wherein the cap comprises one or more grooves configured to self-tap into the fifth metatarsal.

10. The repair system of claim 1, wherein the thread of the fastener is configured to extend distally from the cap when the fastener is disposed within the cap, the cap further comprising one or more hooks extending proximally.

11. A method of using a repair system, comprising:
inserting a fixation device within a canal of a fifth metatarsal;
coupling an end cap to the fixation device by engaging a fastener of the end cap with a lumen of the fixation device;
adjusting the position of the end cap relative to the fixation device to apply intra-operative compression to one or more segments of the fifth metatarsal; and
limiting a depth of insertion of the fixation device based on the end cap, wherein limiting the depth of insertion of the fixation device comprises pulling and rotating a sleeve of an insertion tool to select the depth of insertion.

12. The method of claim 11, further comprising limiting a depth of a counter bore based on the end cap.

13. The method of claim 12, wherein limiting the depth of the counter bore comprises abutting a stop of a reamer with a portion of a drill guide.

14. The method of claim 11, wherein limiting the depth of insertion of the fixation device comprises abutting a sleeve of an insertion tool with the anatomy of a patient.

15. The method of claim 11, further comprising actuating a gripper to secure the fixation device within an intramedullary canal of the fifth metatarsal.

16. The method of claim 11, further comprising rotating a cap of the end cap relative to the fastener after coupling the end cap to the fixation device.

17. The method of claim 11, further comprising angling a cap of the end cap relative to the fastener after coupling the end cap to the fixation device.

* * * * *